(12) United States Patent
Akizawa et al.

(10) Patent No.: US 10,995,119 B2
(45) Date of Patent: May 4, 2021

(54) PEPTIDE EXHIBITING HYDROLYTIC ACTIVITY AND USE THEREOF

(71) Applicant: Okinawa Institute of Science and Technology School Corporation, Okinawa (JP)

(72) Inventors: Toshifumi Akizawa, Osaka (JP); Tadashi Yamamoto, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 155 days.

(21) Appl. No.: 16/067,764

(22) PCT Filed: Jan. 6, 2017

(86) PCT No.: PCT/JP2017/000341
§ 371 (c)(1),
(2) Date: Jul. 2, 2018

(87) PCT Pub. No.: WO2017/119511
PCT Pub. Date: Jul. 13, 2017

(65) Prior Publication Data
US 2019/0023741 A1 Jan. 24, 2019

Related U.S. Application Data

(60) Provisional application No. 62/275,599, filed on Jan. 6, 2016.

(30) Foreign Application Priority Data

Mar. 30, 2016 (JP) .................. 2016-068496

(51) Int. Cl.
*C07K 7/08* (2006.01)
*C07K 14/47* (2006.01)
*C12N 9/50* (2006.01)

(52) U.S. Cl.
CPC .............. *C07K 7/08* (2013.01); *C07K 14/47* (2013.01); *C12N 9/50* (2013.01)

(58) Field of Classification Search
None
See application file for complete search history.

(56) References Cited

U.S. PATENT DOCUMENTS 6,753,413 B1 * 6/2004 Ching ................ C07K 14/4703
530/352

FOREIGN PATENT DOCUMENTS

| EP | 1 548 108 | 6/2005 |
| JP | 2004-313101 | 11/2004 |
| WO | WO 2016/042411 | * 3/2016 |

OTHER PUBLICATIONS

Rouault et al., J Biol Chem. Aug. 28, 1998;273(35):22563-9 (Year: 1998).*
Torkova et al. (Int. J. Mol. Sci. 2015, 16, 25353-25376) (Year: 2015).*
Chan et al. (J. Am. Chem.Soc. 2012, 134, 2589-2598) (Year: 2012).*
Kung et al. (Chem. Commun., 2013, 49, 6888) (Year: 2013).*
Rouault et al., "Interaction of BTG1 and p53-regulated BTG2 Gene Products with mCaf1, the Murine Homolog of a Component of the Yeast CCR4 Transcriptional Regulatory Complex", The Journal of Biological Chemistry, 1998, vol. 273, No. 35, pp. 22563-22569.
Yang et al., "Crystal structures of human BTG2 and mouse TIS21 involved in suppression of CAF1 deadenylase activity", Nucleic Acids Research, 2008, vol. 36, No. 21, pp. 6872-6881.
Hatakawa et al., "A Fragment peptide derived from Box A domain of ANA Protein Cleaves Amyloid β Protein", The 29th Symposium on Biomedical-Analytical Sciences [Online], Jul. 25, 2016, [Date of Search: Mar. 14, 2017], p. 19, Internet: URL:http://www.pharm.kyotou.ac.jp/seizai/bmas2016/doc/BMAS2016
プログラム.pdf **The subject matter presented in the aforementioned Symposium is that of the priority application for the current application.
Taniguchi et al., "Affinity of catalytic peptides to the β-amyloid peptides", The 29th Symposium on Biomedical Analytical Sciences [Online], Jul. 25, 2016, [Date of Search: Mar. 14, 2017], p. 20, Internet: URL:http://www.pharm.kyotou.ac.jp/seizai/bmas2016/doc/BMAS2016プログラム.pdf **The subject matter presented in the afore-mentioned Symposium is that of the priority application for the current application.
Extended European Search Report issued in corresponding European Patent Application No. 17736048.4, dated Jun. 24, 2019, 5 pages.

* cited by examiner

*Primary Examiner* — Sergio Coffa
(74) *Attorney, Agent, or Firm* — Hamre, Schumann, Mueller & Larson, P.C.

(57) ABSTRACT

The present invention provides a novel molecule that catalyzes a hydrolysis reaction and is different from enzyme proteins. The catalytic peptide according to the present invention is a catalytic peptide that catalyzes a hydrolysis reaction, including at least one peptide selected from the group consisting of the following peptides (A1) to (A4):

(A1) a peptide consisting of Box A and at least one of an upstream region and a downstream region therefrom in a Tob/BTG protein;
(A2) a peptide consisting of a partial region of the peptide (A1);
(A3) a peptide that consists of an amino acid sequence obtained by deletion, substitution, addition, and/or insertion of one or more amino acids in an amino acid sequence of the peptide (A1) or (A2) and has hydrolysis activity; and
(A4) a peptide consisting of an amino acid sequence with a sequence identity of at least 85% to the amino acid sequence of the peptide (A1) or (A2) and having hydrolysis activity.

7 Claims, 39 Drawing Sheets

Specification includes a Sequence Listing.

JAL + SOD1 2-38   100 mM Tris-HCl (pH6.5)
SOD1(2-38)            Fr.7
ATKAVCVLKGDGPVQGIINFEQKESNGPVKVWGSIKG JAL + SOD1 2-38   50 mM Tris-HCl (pH7.5)
SOD1(2-38)  Fr.5
ATKAVCVLKGDGPVQGIINFEQKESNGPVKVWGSIKG
       Fr.10              Fr.11

JAL + SOD1 2-38   50 mM Tris-HCl (pH 6.5)

ATKAVCVLKGDGPVQGIINFEQKESNGP     CVLKGDGPVQGIINFEQKESNGPVKVWGSI
KAVCVLKGDGPVQGIINFEQKES     ATKAVCVLKGDGPVQGIINFEQK

KAVCVLKGDGPVQGIINFEQKESNGPVKVWGSI
KAVCVLKGDGPVQGIINFEQKESNGPVKV

JAL + SOD1 2-12        JAL 7-22 + SOD1 2-12
      Fr.6                    Fr.5
ATKAVCVLKGD             ATKAVCVLKGD

FIG. 5

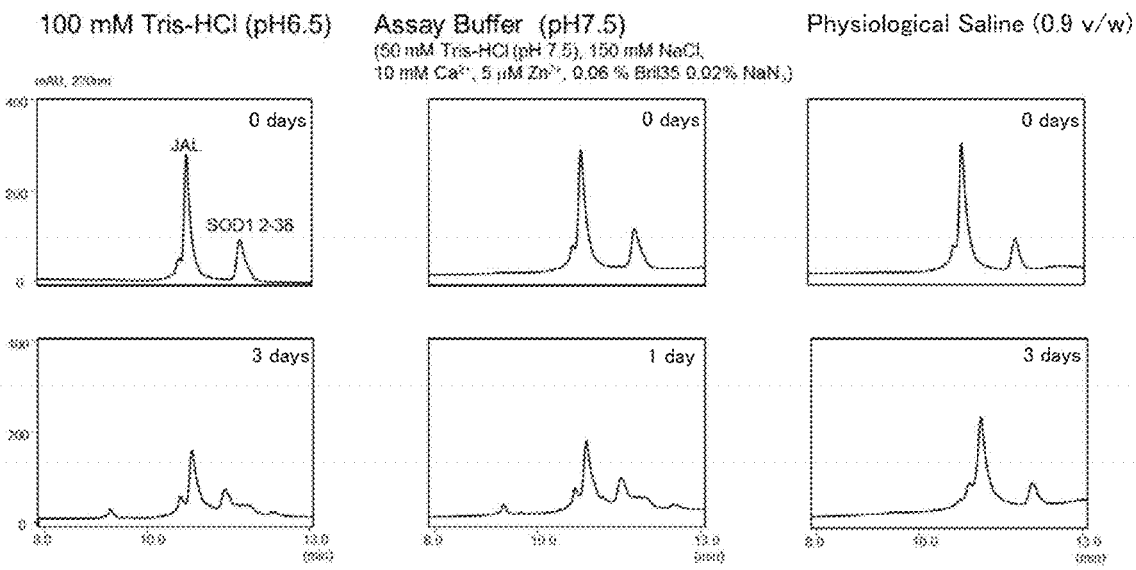

FIG. 6

| BTG/Tob member | Aβ1-20 | ¹DAEFRHDSGYEVHHQKLVFF²⁰ | | | | | | | |
|---|---|---|---|---|---|---|---|---|---|
| Tob 1 7-22 C19M | 1-19 | 1-18 | | | | | | | |
| Tob 1 7-22 | 1-19 | | | | | | | | |
| Tob 2 7-22 | | 1-18 | | | | | | | |
| BTG 1 7-22 | 1-19 | 1-18 | | | | | | | |
| BTG 2 7-22 | | 1-18 | 1-17 | 1-15 | | | 8-20 | | |
| BTG 3 7-22 | | 1-18 | 1-17 | | | | 8-20 | | |
| BTG 4 7-22 | 1-19 | 1-18 | | | 1-12 | | | | |
| Blank | 1-19 | 1-18 | | 1-15 | | | | | |

HSA

| BTG/Tob member | Aβ1-20 | ¹DAEFRHDSGYEVHHQKLVFF²⁰ | | | | | | | |
|---|---|---|---|---|---|---|---|---|---|
| Tob 1 7-22 | 1-19 | 1-18 | | 1-15 | | 1-11 | | 6-15 | 2-9 |
| Tob 2 7-22 | | 1-18 | | | 1-13 | | | | 10-16 |
| BTG 1 7-22 | | 1-18 | 1-17 | | | | 1-5 | | 12-18 |
| BTG 2 7-22 | | 1-18 | 1-17 | | | | | | 12-18 |
| BTG 3 7-22 | | 1-18 | 1-17 | | | | 8-20 | | |
| BTG 4 7-22 | | 1-18 | 1-17 | | 1-12 | | | | 12-18 14-18 |
| Blank | | 1-18 | 1-17 | 1-15 | | | 1-5 | | 12-18 |

| BTG/Tob member | Aβ11-29 | ¹¹EVHHQKLVFFAEDVGSNKG²⁹ | | | | | | |
|---|---|---|---|---|---|---|---|---|
| Tob 1 7-22 C19M | | | | | | | | |
| Tob 1 7-22 | | | 11-17 | 11-20 | 15-22 | | 20-29 | |
| Tob 2 7-22 | 11-18 | | | | | 19-29 | | |
| BTG 1 7-22 | | | | | | | 20-29 | |
| BTG 2 7-22 | 11-18 | 11-17 | | | | | | |
| BTG 3 7-22 | 11-18 | 11-17 | | | | | 20-29 | |
| BTG 4 7-22 | | | | | | | 20-29 | |
| Blank | 11-18 | | | | | 19-29 | 20-29 | |

HSA

| BTG/Tob member | Aβ11-29 | ¹¹EVHHQKLVFFAEDVGSNKG²⁹ | | | | | | |
|---|---|---|---|---|---|---|---|---|
| Tob 1 7-22 C19M | | 15-22 | | | | | | |
| Tob 1 7-22 | | | 19-29 | 20-29 | 20-28 | | | |
| Tob 2 7-22 | 11-18 | | | 20-29 | | | 14-22 | 17-24 |
| BTG 1 7-22 | 11-18 | | | 20-29 | | 12-23 | | |
| BTG 2 7-22 | 11-18 | | | | | | | |
| BTG 3 7-22 | 11-18 | 11-17 | | 20-29 | | | | |
| BTG 4 7-22 | 11-18 | | | | | 21-29 | | |
| Blank | 11-18 | | 19-29 | 20-29 | | | | |

FIG. 13

```
HSA
BTG/Tob member          PrP175-189   175FVHDCVNITIKQHTV189
Tob 1 7-22
Tob 2 7-22                                         184-189
BTG 1 7-22                                         184-189
BTG 2 7-22
BTG 3 7-22                                 183-189 184-189
BTG 4 7-22              178-185    178-186

HSA + Cu2+
BTG/Tob member          PrP175-189   175FVHDCVNITIKQHTV189
Tob 1 7-22 not added
Tob 2 7-22        175-179 + 177-185
BTG 1 7-22 not added
BTG 2 7-22 not added
BTG 3 7-22                                 186-189 175-178
BTG 4 7-22 not added
```

FIG. 14

| Tob 1 ( JAL ) | Structural Formula | Number of aa |
|---|---|---|
| 1-22 | KYEGHWYPEKPYKGSGFRCIHI | 22 |
| 7-22 C19M | YPEKPYKGSGFRMIHI | 16 |
| 7-22 E9A C19M | YPAKPYKGSGFRMIHI | 16 |
| 7-22 P8W E9A C19M | YWAKPYKGSGFRMIHI | 16 |
| 7-22 Y7A C19M I22A | APEKPYKGSGFRMIHA | 16 |
| 7-22 Y7A K10A C19M I22A | APEAPYKGSGFRMIHA | 16 |
| 9-20 C19M | EKPYKGSGFRMI | 12 |
| 12-22 C19M I22A | YKGSGFRMIHA | 11 |
| 12-20 C19M | YKGSGFRMI | 9 |
| 12-20 Y12A C19M | AKGSGFRMI | 9 |
| 12-18 | YKGSGFR | 7 |
| 12-18 S15A | YKGAGFR | 7 |
| 13-17 | KGSGF | 5 |
| 14-22 | GSGFRCIHI | 9 |
| 2-18 | YEGHWYPEKPYKGSGFR | 17 |
| 13-19 | KGSGFRM | 7 |
| 14-18 | GSGFR | 5 |
| 14-18 R18H | GSGFH | 5 |
| 14-18 F17X | GSGXR | 5 |

FIG. 15

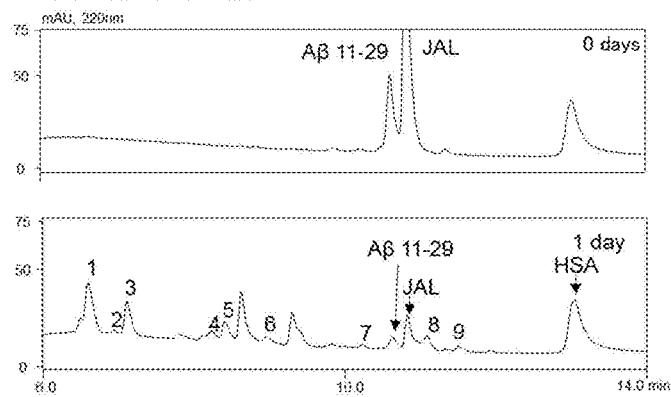
Aβ: ¹¹EVHHQKLVFFAEDVGSNKG²⁹
1: ²³DVGSNKG²⁹
2: ²²EDVGSNKG²⁹
3: ²¹AEDVGSNKG²⁹
4: ¹⁴HQKL¹⁷
5: ¹¹EVHHQKL¹⁷
6: ¹¹EVHHQKLV¹⁸
7: ¹⁹FFAE²²
8: ¹⁸VFFA²¹
9: ¹⁴HQK¹⁶
FIG. 21
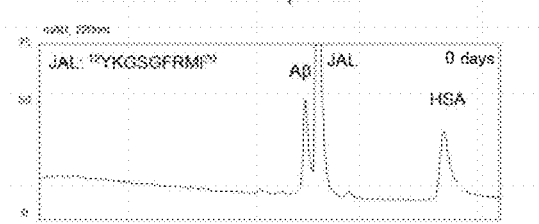
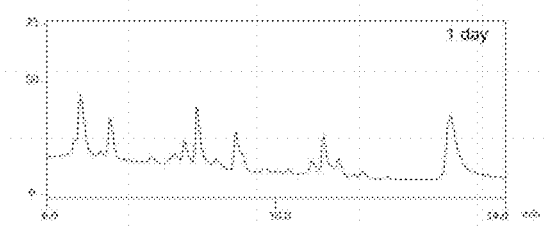
¹²YKGSGFRMI²⁰
FIG. 22

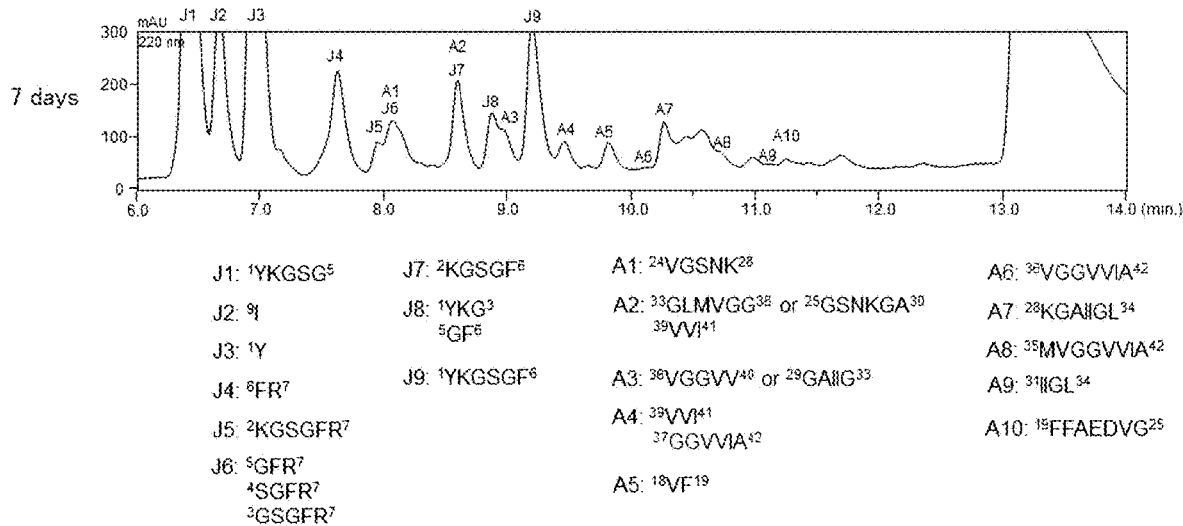
FIG. 33
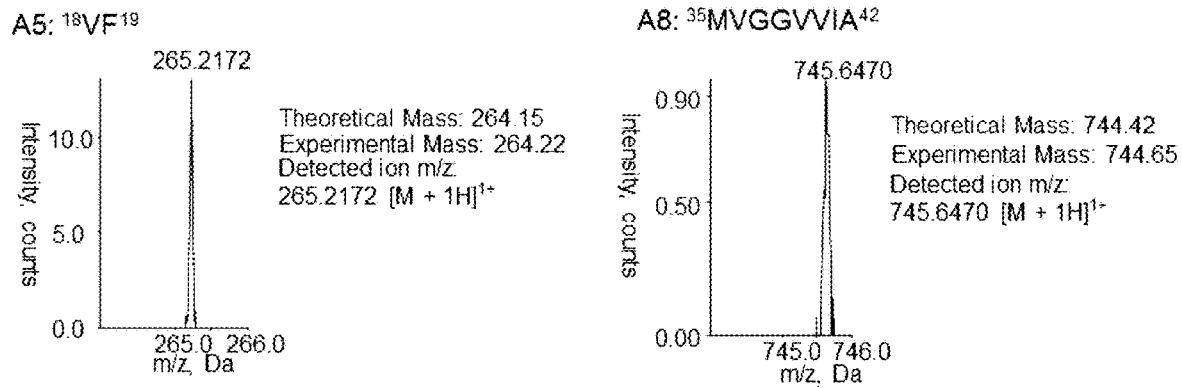
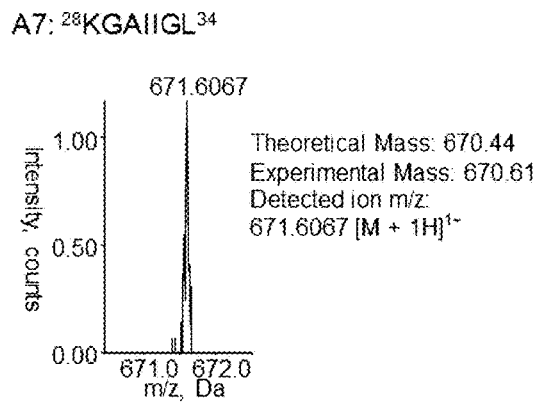
FIG. 34

1 day
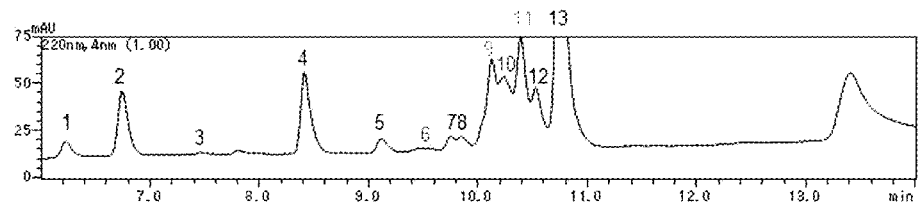
1: YKGSG (MW: 510.2494)
2: Y (MW: 181.0716)
3: FR (MW: 321.1802)
4: YKGSGFR (MW: 813.4215)
5: MI (MW: 262.1364)
6: Tau MBD 10-18 (MW: 910.4792)
7: JAL-TA9 + OH (MW: 1073.5431)
8: YKGSGFRM (MW: 944.4738)
9: Tau MBD 1-22 (MW: 2276.2696)
Tau MBD 1-30 (MW: 3136.7690)
10: Tau MBD 4-21 (MW: 2036.1222)
11: Tau MBD 1-28 (MW: 2921.6415)
12: KGSGFRMI (MW: 894.4776)
13: JAL-TA9 (MW: 1057.5507)
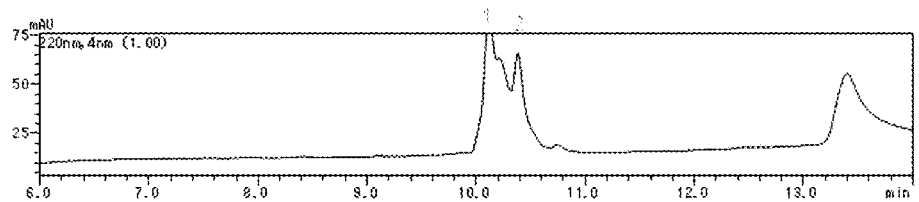
1: Tau MBD 1-30 (MW: 3136.7888)
   Tau MBD 1-22 (MW: 3136.7888)
2: Tau MBD 1-28 (MW: 2921.6687)
FIG. 44

5 days

1: YKGSG (MW: 510.2494)
2: Y (MW: 181.0771)
3: FR (MW: 321.1891)
4: KGSGFR (MW: 650.3556)
   Tau MBD 2-7 (MW: 704.2906)
5: SGFR (MW: 465.2504)
   GSGFR (MW: 522.2750)
6: YKSGFR (MW: 813.4443)
   KGSGF (MW: 494.2573)
7: Tau MBD 20-28 (MW: 985.6024)
   MI (MW: 262.1458)

8: Tau MBD 10-18 (MW: 910.5123)
9: KGSGFRM (MW: 781.4150)
   FRM (MW: 452.7794)
10: JAL-TA9+OH (MW: 1073.5719)
11: Tau MBD 13-21 (MW: 998.4814)
12: Tau MBD 1-22 (MW: 2276.3072)
13: Tau MBD 4-21 (MW: 2036.1549)
    Tau MBD 1-28 (MW: 2921.6700)
14: KGSGFRMI (MW: 894.5112)
    Tau MBD 5-11 (MW: 763.4022)

15: JAL-TA9 (MW: 1057.5768)
16: SGFRMI (MW: 709.3802)
    GSGFRMI (MW: 766.4022)
    GFRMI (MW: 622.3362)

1: Tau MBD 1-22 (MW: 2276.3108)
2: Tau MBD 1-30 (MW: 3138.6428)
3: Tau MBD 1-28 (MW: 3138.6428)

Tau MBD 1-30

6 days

Aβ binding site-AA-JAL-TA9 + Aβ 11-29

Aβ: $^{11}$EVHHQKLVFFAEDVGSNKG$^{29}$

2: $^{22}$EDVGSNKG$^{29}$
3: $^{21}$AEDVGSNKG$^{29}$
6: $^{20}$FAEDVGSNKG$^{29}$
10: $^{19}$FFAEDVGSNKG$^{29}$
15: $^{18}$LVF$^{20}$
$^{17}$VFFA$^{19}$ 7 days

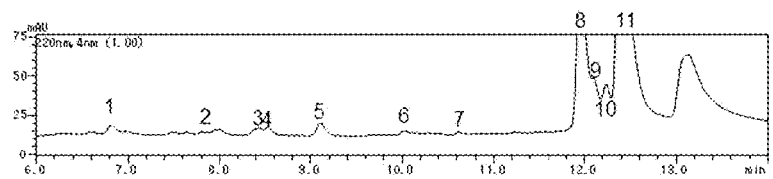

Aβ binding AA JAL-TA9 + Aβ42

1: $^{12}$Y
2: $^{24}$SGFRMI$^{29}$
3: $^{23}$GSGFRMI$^{29}$
4: $^{8}$SGYEVHHQ$^{15}$
5: $^{28}$MI$^{29}$
6: $^{18}$KAAYKGSGFRMI$^{29}$

7: $^{21}$YKGSGFRMI$^{29}$
8: $^{1}$FVIFLDVKHFSPEDLTVKAAYKGSGFR$^{27}$
   $^{24}$VGSNKGAIIGLMVG$^{37}$
9: $^{1}$DAEFRHDSGYEVHHQKLVFFAEDVGSNKGAIIGLMVG$^{37}$
   $^{11}$EVHHQKLVFFAEDVGSNKGAIIGLMVGGVVIA$^{42}$
10: $^{1}$FVIFLDVKHFSPEDLTVKAA$^{20}$
11: $^{1}$FVIFLDVKHFSPEDLTVKAAYKGSGFRMI$^{29}$ $^{1}$DAEFRHDSGYEVHHQKLVFFAEDVGSNKGAIIGLMVGGVVIA$^{42}$
↑   ↑   ↑   ↑   ↑

FIG. 50

7 days

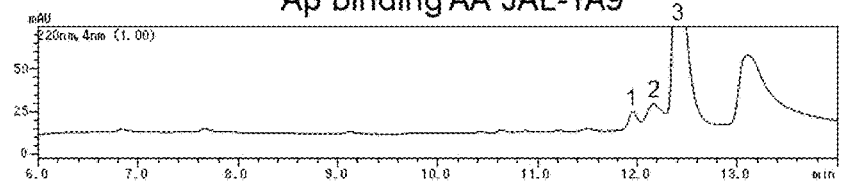

Aβ binding AA JAL-TA9

1: $^{1}$FVIFLDVKHFSPEDLTVKAAYKGSGFR$^{27}$
   $^{1}$FVIFLDVKHFSPEDLTVKAAYKGSGF$^{26}$
2: $^{1}$FVIFLDVKHFSPEDLTVKAA$^{20}$
3: $^{1}$FVIFLDVKHFSPEDLTVKAAYKGSGFRMI$^{29}$ 7 days

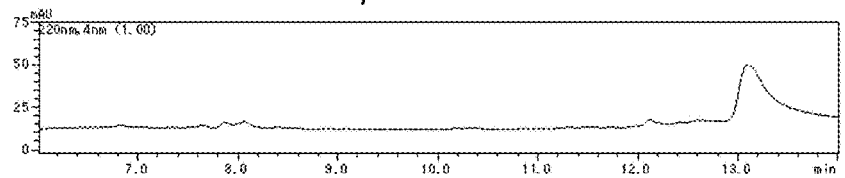

| | | I | II | II | III | III | IV | V | V | V | VI | VI |
|---|---|---|---|---|---|---|---|---|---|---|---|---|
| Catalytide | 1mM ANA-TA9 | 40 | 20 | 20 | 20 | 20 | 20 | - | - | - | - | - |
| | 1mM ANA-YA4 | - | - | - | - | - | - | 20 | 20 | 20 | - | - |
| | 1mM ANA-SA5 | - | - | - | - | - | - | - | - | - | 20 | 20 |
| Substrate | 1mM Aβ1-20 or Aβ11-29 | - | - | - | 5 | - | - | 5 | - | 5 | - |
| | 1mM Aβ28-42 (2.5% DMSO) | - | - | - | - | 5 | - | - | 5 | - | 5 |
| | 5mM Aβ42 (2.5% DMSO) | - | - | - | - | - | 1 | - | - | - | - | - |
| Inhibitor | cOmplete | - | 20 | - | - | - | - | - | - | - | - | - |
| | AEBSF | - | - | 20 | - | - | - | - | - | - | - | - |
| Buffer | PBS | 20 | 10 | 10 | 10 | 10 | 10 | 10 | 10 | 10 | 10 | 10 |
| | 10% DMSO | 10 | 5 | 5 | 5 | - | - | 5 | 5 | - | 5 | - |
| | 0.5% HSA | 10 | 5 | 5 | 5 | 5 | 5 | 5 | 5 | 5 | 5 | 5 |
| | MilliQ | 120 | 40 | 40 | 55 | 60 | 64 | 60 | 55 | 60 | 55 | 60 |
| Total (μL) | | 200 | 100 | 100 | 100 | 100 | 100 | 100 | 100 | 100 | 100 | 100 |

1: $^6YR^7$  2: $^7RM^8, ^6Y$  3: $^1SKGQAYR^7$
4: $^1SKGQAY^6$  5: $^6YRM^8$  6: $^6YRMI^9$

1: ¹⁷YR¹⁸
2: ¹⁷Y
3: ¹⁴HQKL¹⁷
4:
5: ¹⁴HQKLV¹⁸
6: ¹⁷YRM¹⁹
7: ¹DAEFRHDSGYEVH¹⁴
8: ¹⁹MI²⁰
9: ¹⁷YRMI²⁰
10: ¹⁴HQKLVF¹⁹
11: ¹DAEFRHDSGYEVHHQKLVFF²⁰
12: ¹⁴HQKLVFF²⁰
13: ¹⁵QKLVFF²⁰

↓↓ ↓↓↓
¹DAEFRHDSGYEVHHQKLVFF²⁰

1: ¹¹EVH¹³ or ¹⁹FFA²¹
2:
3: ¹¹EVHHQK¹⁶
4: ¹⁷YR¹⁸
5: ¹⁷Y
   ²¹AEDVGSNKG²⁹
6: ¹⁴HQKL¹⁷
7: ¹¹EVHHQKL¹⁷
8: ²⁰FAEDVGSNKG²⁹

9: ¹⁴HQKLV¹⁸
10: ¹⁷YRM¹⁹
11: ¹⁹MI²⁰
    ²²EDVG²⁵
12:
13: ¹⁹FFAEDVGSNKG²⁹
14: ¹⁷YRMI²⁰
15: ¹⁸VFFAEDVGSNKG²⁹

16: ¹⁴HQKLVF¹⁹
17: ¹⁴HQKLVFFAEDVGSNKG²⁹
18: ¹⁹FF²⁰
    ¹⁶KLVF¹⁹ or ²²EDVGS²⁶
19: ¹⁸VFFA²¹
20: ¹⁴HQKLVFF²⁰
21: ¹⁴HQK¹⁶
22: ¹⁵QKLVFF²⁰

↓↓↓↓↑↑↓↓↓↓     ↓
¹¹EVHHQKLVFFAEDVGSNKG²⁹

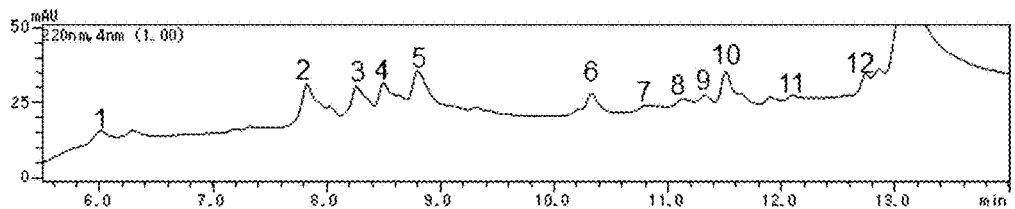
- P1: VHHQK
- P2: F
- P3: DAEFR
- P4: HQKLV
- P5: DAEFRHDSGYEVH
- P6: HQKLVF
- P7: FF
- P8: Aβ1-20
- P9: LVF
- P10: VFF, HQKLVFF
- P11: KLVFF
- P12: LVFF
FIG. 63
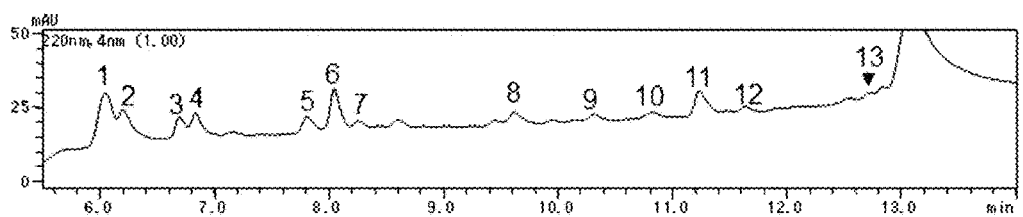
- P1: EVHHQ
- P2: DVGSNKG
- P3: EDVGSNKG
- P4: AEDVGSNKG
- P5: HQKL
- P6: EVHHQKL
- P7: FAEDVGSNKG
- P8: FFAEDVGSNKG
- P9: FFA
- P10: KLVF
- P11: VFFA
- P12: VFF
- P13: LVFF
FIG. 64

JAL-TA9 + A-crystallin
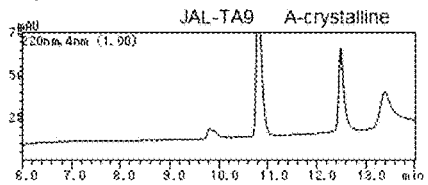
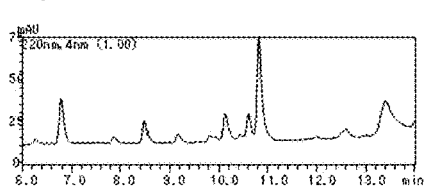
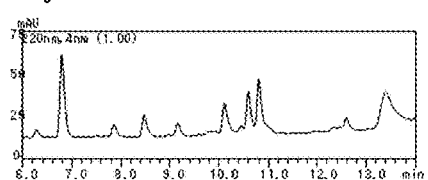
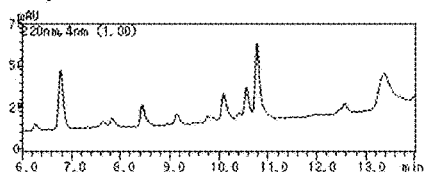
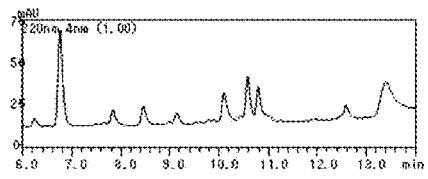
FIG. 65
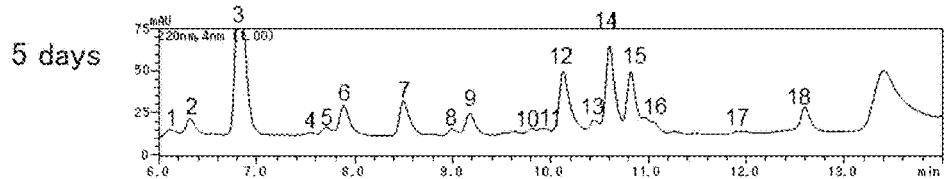
1: DVKH (MW: 497.2650)
2: YKGSG (MW: 510.2482)
3: Y (MW: 181.0733)
4: FR (MW: 321.1876)
5: Unidentified (MW: 1860.1758)
6: KGSGFR (MW: 650.3564)
7: YKGSGFR (MW: 813.4215)
8: SPEDLTVK (MW: 887.4658)
9: MI (MW: 262.1350)
10: HFSPEDLT (MW: 944.4702)
11: VKHFSPEDLTVK (MW: 1398.7593)
12: DVKHFSPEDLTVK (MW: 1513.7880)
13: FSPEDLTVK (MW: 1034.5274)
14: KGSGFRMI (MW: 894.4806)
15: JAL-TA9 (MW: 1057.5483)
16: GSGFRMI (MW: 766.3806)
17: FVIFLDVKH (MW: 1116.6411)
18: A-crystallin (MW: 1116.6411)
$^1$FVIFLDVKHFSPEDLTVK$^{18}$
FIG. 66

P1: GYEVHHQKL (MW 984.4074)

P2: unknown (MW 187.0619)

P3: WID (MW: 432.2016)

P4: DAEFRHDSGYEVHHQKLVF (MW 2313.1375)

P5: Ab1-20 (MW 24610.2005)

P6: FRHDSGY (MW 917.5208)

P7: WIDPFEVSYQI (MW: 1395.6744)

P8: WIDPF (MW: 676.3258)

P9: Tob1 BoxB 8-20 (MW: 1581.7478)

P1: unknown (MW 187.0613)

P2: EVSYQIGE (MW: 923.4299)

P3: WID (MW: 432.2016)

P4: Ab11-29 (MW: 2140.1104)

P5: EVHHQKLVFF (MW: 1282.7019)

P6: WIDPFEVSYQI (MW: 1395.6744)

P7: WIDPF (MW: 676.3258)

P8: Tob1 BoxB 8-20 (MW: 1581.7478)

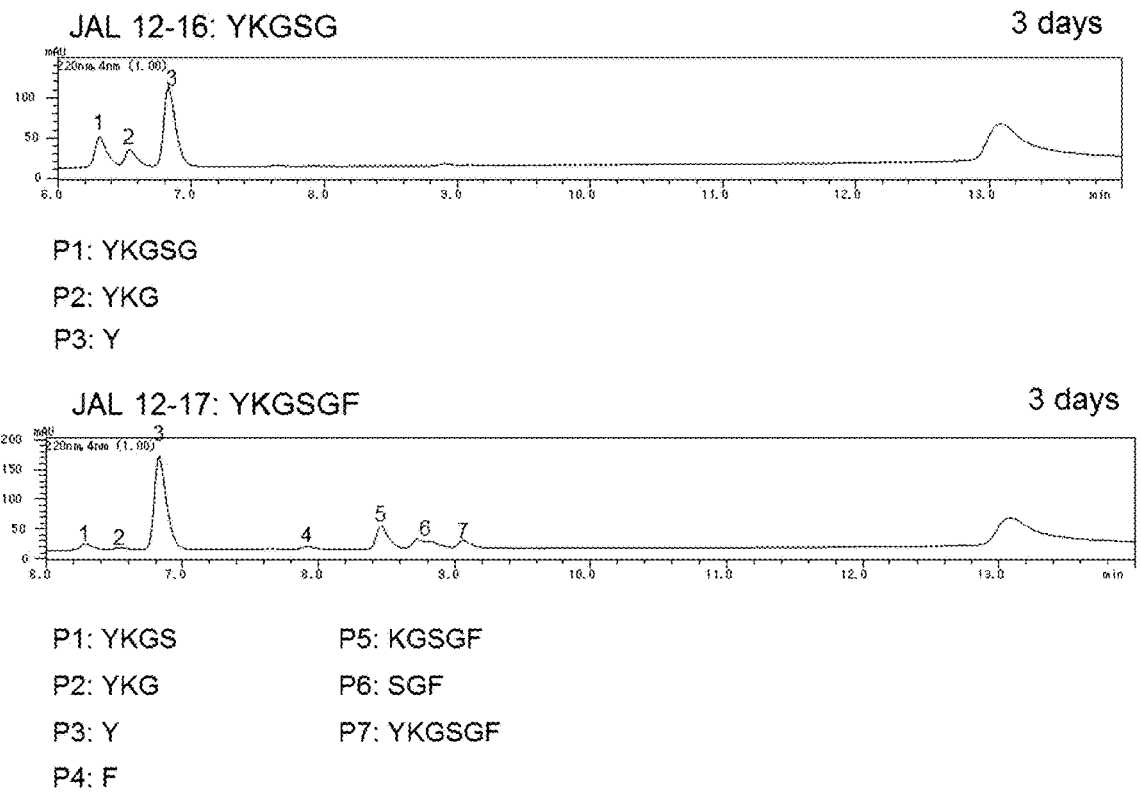
FIG. 71
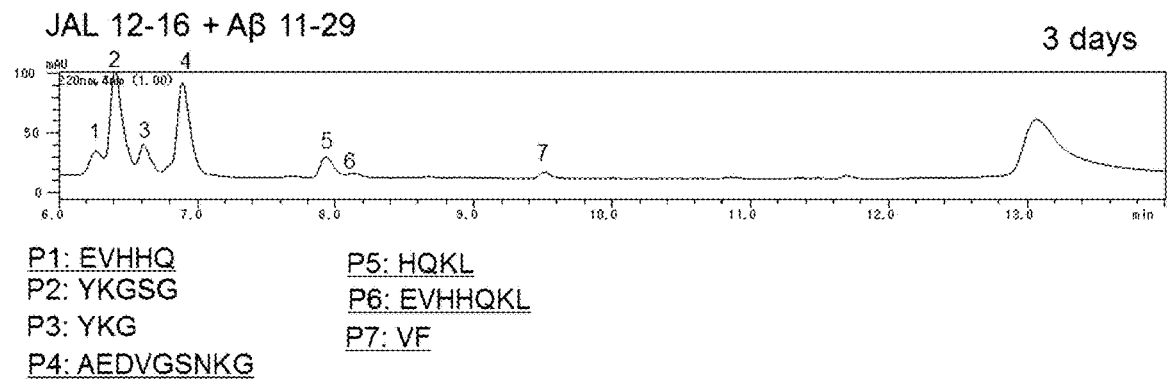
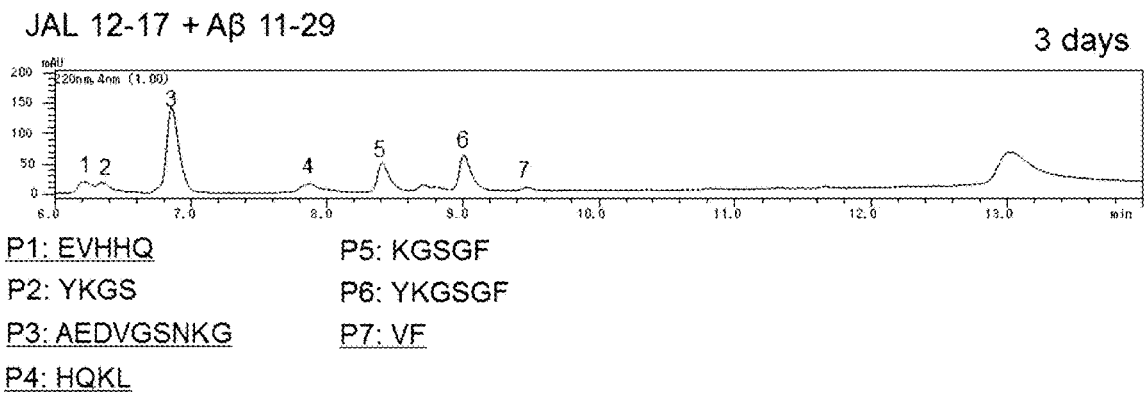
FIG. 72

PEPTIDE EXHIBITING HYDROLYTIC ACTIVITY AND USE THEREOF

This application claims priority from U.S. Provisional Patent Application No. 62/275,599 filed on Jan. 6, 2016 and Japanese Patent Application No. 2016-068496 filed on Mar. 30, 2016. The entire disclosure of these patent applications is incorporated herein by reference.

TECHNICAL FIELD

The present invention relates to a novel peptide exhibiting hydrolysis activity and use thereof.

BACKGROUND ART

In a biochemical approach to degrade a protein, an enzyme protein that catalyzes a hydrolysis reaction is used generally. However, it is known that the stability of an enzyme protein is affected easily by, for example, conditions such as humidity, temperature, and acidity, so that the enzyme protein is denatured easily. On this account, there is a demand for a novel molecule that catalyzes a reaction in a similar manner to an enzyme protein.

SUMMARY OF INVENTION

Technical Problem

With the foregoing in mind, it is an object of the present invention to provide a novel molecule that catalyzes a hydrolysis reaction and is different from an enzyme protein.

Solution to Problem

The present invention provides a catalytic peptide that catalyzes a hydrolysis reaction, including: at least one peptide selected from the group consisting of the following peptides (A1) to (C4):

(A1) a peptide consisting of Box A and at least one of an upstream region and a downstream region therefrom in a Tob/BTG protein;
(A2) a peptide consisting of a partial region of the peptide (A1);
(A3) a peptide that consists of an amino acid sequence obtained by deletion, substitution, addition, and/or insertion of one or more amino acids in an amino acid sequence of the peptide (A1) or (A2) and has hydrolysis activity;
(A4) a peptide consisting of an amino acid sequence with a sequence identity of at least 85% to the amino acid sequence of the peptide (A1) or (A2) and having hydrolysis activity;
(B1) a peptide consisting of Box B in the Tob/BTG protein;
(B2) a peptide consisting of a partial region of the peptide (B1);
(B3) a peptide that consists of an amino acid sequence obtained by deletion, substitution, addition, and/or insertion of one or more amino acids in an amino acid sequence of the peptide (B1) or (B2) and has hydrolysis activity;
(B4) a peptide consisting of an amino acid sequence with a sequence identity of at least 85% to the amino acid sequence of the peptide (B1) or (B2) and having hydrolysis activity;
(C1) a peptide consisting of a C-terminal region or an intermediate region in the Tob/BTG protein;
(C2) a peptide consisting of a partial region of the peptide (C1);
(C3) a peptide that consists of an amino acid sequence obtained by deletion, substitution, addition, and/or insertion of one or more amino acids in an amino acid sequence of the peptide (C1) or (C2) and has hydrolysis activity; and
(C4) a peptide consisting of an amino acid sequence with a sequence identity of at least 85% to the amino acid sequence of the peptide (C1) or (C2) and having hydrolysis activity.

The present invention also provides a catalytic peptide reagent containing a catalytic molecule, wherein the catalytic molecule is the catalytic peptide according to the present invention.

The present invention also provides a method for degrading a protein or a peptide, including the step of: treating a substrate with the catalytic peptide according to the present invention, wherein the substrate is a protein or a peptide.

Advantageous Effects of Invention

The catalytic peptide of the present invention can catalyze a hydrolysis reaction. Unlike enzyme proteins, the catalytic peptide of the present invention has a low molecular weight. Thus, the catalytic peptide of the present invention is applicable to a hydrolysis reaction as a novel catalytic molecule different from the proteins.

BRIEF DESCRIPTION OF DRAWINGS

FIG. 5 shows the sequences of fragments obtained through degradation by the catalytic peptide.
FIG. 6 shows chromatograms showing the influence of buffer solutions on the hydrolysis activity of the catalytic peptide.
FIG. 13 shows the sequences of fragments obtained through degradation by catalytic peptides.
FIG. 14 shows fragments obtained through degradation by the catalytic peptides.
FIG. 15 is a table showing whether various catalytic peptides have hydrolysis activity.

FIG. 21 shows chromatograms showing the hydrolysis activity of a catalytic peptide, and the amino acid sequences of fragments obtained by degradation.

FIG. 22 shows chromatograms showing inhibition of autodigestion of the catalytic peptide by various protease inhibitors.

FIG. 33 shows a chromatogram showing the hydrolysis activity of the catalytic peptide against Aβ.

FIG. 34 shows chromatograms showing the hydrolysis activity of the catalytic peptide against Aβ.

FIG. 44 shows chromatograms showing the hydrolysis activity of the catalytic peptide against Tau.

FIG. 50 shows a chromatogram showing the hydrolysis activity of the catalytic peptide against Aβ.

FIG. 51 shows chromatograms showing the hydrolysis activity of the catalytic peptide against Aβ.

FIG. 63 shows a chromatogram showing the hydrolysis activity of the catalytic peptide against Aβ.

FIG. 64 shows a chromatogram showing the hydrolysis activity of the catalytic peptide against Aβ.

FIG. 65 shows chromatograms showing the hydrolysis activity of a catalytic peptide against crystallin.

FIG. 66 shows a chromatogram showing the hydrolysis activity of a catalytic peptide against crystallin.

FIG. 71 shows chromatograms showing autodigestion of the catalytic peptides.

FIG. 72 shows chromatograms showing the hydrolysis activity of the catalytic peptides against Aβ.

DESCRIPTION OF EMBODIMENTS

<Catalytic Peptide>

Figure 1:
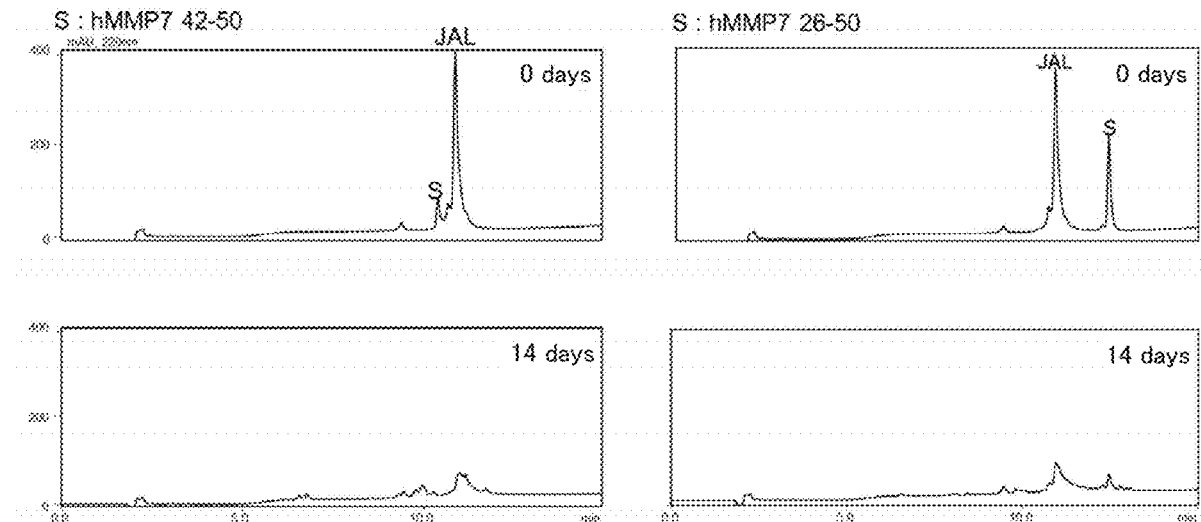
FIG. 1 shows chromatograms showing the hydrolysis activity of a catalytic peptide.

As described above, the catalytic peptide of the present invention is a peptide that catalyzes hydrolysis reaction and is characterized in that it includes at least one peptide selected from the group consisting of the above-described peptides (A1) to (C4).

The inventors of the present invention found out through diligent research that a peptide present in a region whose function is unknown in a Tob/BTG protein has hydrolysis activity catalyzing a hydrolysis reaction. The catalytic peptide of the present invention is a small molecule with a short strand, so that, for example, it has higher stability against water, temperatures, acids, etc. than enzyme proteins and thus is less liable to be denatured. Accordingly, the catalytic peptide of the present invention can be handled more easily than enzyme proteins, serves as an alternative to an enzyme protein, and is applicable to various uses.

The length of the catalytic peptide of the present invention is as follows: the lower limit of the number of amino acid residues is, for example, 5, 7, or 9, the upper limit thereof is, for example, 22, 18, or 17, and the range thereof is, for example, from 5 to 22, from 5 to 18, or from 5 to 17.

As the catalytic peptide of the present invention, first, the peptides (A1) to (A4) will be described.

The peptide (A1) is a peptide consisting of Box A and at least one of an upstream region and a downstream region therefrom in a Tob/BTG protein. The peptide (A1) may be, for example: a peptide consisting of Box A and the upstream region therefrom; a peptide consisting of Box A and the downstream region therefrom; or a peptide consisting of the upstream region, Box A, and the downstream region.

In the peptide (A1), the amino acid sequence of Box A is not particularly limited, and may be the amino acid sequence of SEQ ID NO: 1, for example. In SEQ ID NO: 1, for example, $Xaa_1$ is Y, F, or H, $Xaa_2$ is P or S, $Xaa_3$ is E or D, $Xaa_4$ is K or C, $Xaa_5$ is Y, L, C, or S, $Xaa_6$ is S or Q, $Xaa_7$ is G or A, $Xaa_8$ is F or Y, $Xaa_9$ is V or I, $Xaa_{10}$ is H or R, and $Xaa_{11}$ is I or V.

Box A:

SEQ ID NO: 1

HW[Xaa$_1$][Xaa$_2$][Xaa$_3$][Xaa$_4$]P[Xaa$_5$]KG[Xaa$_6$][Xaa$_7$][Xaa$_8$]

RC[Xaa$_9$][Xaa$_{10}$][Xaa$_{11}$]

Specific examples of Box A represented by SEQ ID NO: 1 include the following sequences.

TABLE 1

| Box A | Sequence | SEQ ID NO: |
|---|---|---|
| TOB1 | HWYPEKPYKGSGFRCIHI | 3 |
| TOB2 | HWYPEKPLKGSGFRCVHI | 44 |
| BTG1 | HWFPEKPCKGSGYRCIRI | 45 |
| BTG2 | HWFPEKPSKGSGYRCIRI | 46 |
| BTG3 | HWYPEKPSKGQAYRCIRV | 47 |
| BTG4 | HWHSDCPSKGQAFRCIRI | 48 |

In the peptide (A1), the length of the upstream region is as follows: the lower limit of the number of amino acid residues is, for example, 1 or 2, the upper limit thereof is, for example, 10, 8, 6, or 4, and the range thereof is, for example, from 1 to 10, from 1 to 8, from 1 to 6, or from 1 to 4. Also, in the peptide (A1), the length of the downstream region is as follows: the lower limit of the number of amino acid residues is, for example, 1 or 2, the upper limit thereof is, for example, 10, 8, 6, or 4, and the range thereof is, for example, from 1 to 10, from 1 to 8, from 1 to 6, or from 1 to 4.

The length of the peptide (A1) is as follows: the lower limit of the number of amino acid residues is, for example, 18 or 20, the upper limit thereof is, for example, 30, 26, or 22, and the range thereof is, for example, from 18 to 30, from 18 to 26, or from 18 to 22.

Specifically, the peptide (A1) may be a peptide JAL consisting of an amino acid sequence of SEQ ID NO: 2, for example. In the sequence of JAL, the underlined part corresponds to Box A represented by SEQ ID NO: 3. In SEQ ID NO: 2, the underlined sequence may be substituted by the sequence of any one of SEQ ID NOs: 44 to 48, for example.

JAL (Tob1):

SEQ ID NO: 2

KYEG<u>HWYPEKPYKGSGFRCIHI</u>

The peptide (A2) is a peptide consisting of a partial region of the peptide (A1). The length of the peptide (A2) is as follows: the lower limit of the number of amino acid residues is, for example, 5, 7, or 9, the upper limit thereof is, for example, 18, 17, or 16, and the range thereof is, for example, from 5 to 18, from 5 to 17, or from 5 to 16.

Specifically, the peptide (A2) may be Box A consisting of the peptide of SEQ ID NO: 1, for example.

Other specific examples of the peptide (A2) include peptides consisting of at least one amino acid sequence selected from the group consisting of SEQ ID NOs: 3 to 14. SEQ ID NO: 3 is Box A. SEQ ID NOs: 4 and 10 to 14 are peptides consisting of partial regions of JAL (Tob1) represented by SEQ ID NO: 2, which is the peptide (A1). Among them, SEQ ID NOs: 4 and 11 to 14 are peptides consisting of partial regions of Box A (TOB1) represented by SEQ ID NO: 3. SEQ ID NOs: 5 to 9 are peptides consisting of partial regions of Box A represented by SEQ ID NO: 1 or 3.

TABLE 2

| BoxA (TOB1) | HWYPEKPYKGSGFRCIHI | SEQ ID NO: 3 |
|---|---|---|
| JAL7-22: | YPEKPYKGSGFRCIHI | SEQ ID NO: 4 |
| Tob2 7-22: | YPEKPLKGSGFRCVHI | SEQ ID NO: 5 |
| BTG1 7-22: | FPEKPCKGSGYRCIRI | SEQ ID NO: 6 |
| BTG2 7-22: | FPEKPSKGSGYRCIRI | SEQ ID NO: 7 |
| BTG3 7-22: | YPEKPSKGQAYRCIRV | SEQ ID NO: 8 |
| BTG4 7-22: | HSDCPSKGQAFRCIRI | SEQ ID NO: 9 |
| JAL2-18: | YEGHWYPEKPYKGSGER | SEQ ID NO: 10 |
| JAL12-18: | YKGSGFR | SEQ ID NO: 11 |
| JAL13-17: | KGSGF | SEQ ID NO: 12 |
| JAL14-18: | GSGFR | SEQ ID NO: 13 |
| JAL14-22: | GSGERCIHI | SEQ ID NO: 14 |

The peptide (A3) is a peptide that consists of an amino acid sequence obtained by deletion, substitution, addition, and/or insertion of one or more amino acids in the amino acid sequence of the peptide (A1) or (A2) and has hydrolysis activity. In the peptide (A3), the number of the deleted, substituted, added, and/or inserted amino acid residues is not particularly limited, and is, for example, 1 to 5, 1 to 3, 1, or 2.

Specific examples of the peptide (A3) include peptides consisting of amino acid sequences of SEQ ID NOs: 15 to 26 and SEQ ID NOs: 50 and 53.

TABLE 3

| | | |
|---|---|---|
| JAL13-19 C19M: | KGSGFRM | SEQ ID NO: 15 |
| JAL1-22 C19M: | KYEGHWYPEKPYKGSGFRMIHI | SEQ ID NO: 16 |
| JAL7-22 C19M: | YPEKPYKGSGFRMIHI | SEQ ID NO: 17 |
| JAL7-22 E9A C19M: | YPAKPYKGSGFRMIHI | SEQ ID NO: 18 |
| JAL7-22 P8W E9A C19M: | YWAKPYKGSGFRMIHI | SEQ ID NO: 19 |
| JAL7-22 Y7A C19M I22A: | APEKPYKGSGFRMIHA | SEQ ID NO: 20 |
| JAL7-22 Y7A K10A C19M I22A: | APEAPYKGSGFRMIHA | SEQ ID NO: 21 |
| JAL9-20 C19M: | EKPYKGSGFRMI | SEQ ID NO: 22 |
| JAL12-22 C19M I22A: | YKGSGFRMIHA | SEQ ID NO: 23 |
| JAL12-20 C19M: | YKGSGFRMI | SEQ ID NO: 24 |
| JAL12-20 Y12A C19M: | AKGSGFRMI | SEQ ID NO: 25 |
| JAL12-18 S15A: | YKGAGFR | SEQ ID NO: 26 |
| JAL-TA9: | PYKGSGFRMI | SEQ ID NO: 50 |
| ANA-TA9: | SKGQAYRMI | SEQ ID NO: 53 |
| ANA-SA4: | YRMI | SEQ ID NO: 54 |
| ANA-SA5: | SKGQA | SEQ ID NO: 55 |

Specific examples of the peptide (A3) further include peptides consisting of amino acid sequences of SEQ ID NOs: 27 to 31. In SEQ ID NO: 27, Xaa is W, L, V, N, or D. In SEQ ID NO: 28, Xaa is K, V, T, Y, or M. In SEQ ID NO: 29, Xaa is T, E, P, W, or K. In SEQ ID NO: 30, Xaa is H, V, W, Y, R, L, P, M, E, A, D, Q, N, K, or G. In SEQ ID NO: 31, Xaa is T, Q, V, K, or E.

TABLE 4

| | | |
|---|---|---|
| JAL14-18 14sub: | XaaSGFR | SEQ ID NO: 27 |
| JAL14-18 15sub: | GXaaGFR | SEQ ID NO: 28 |
| JAL14-18 16sub: | GSXaaFR | SEQ ID NO: 29 |
| JAL14-18 17sub: | GSGXaaR | SEQ ID NO: 30 |
| JAL14-18 18sub: | GSGFXaa | SEQ ID NO: 31 |

The peptide (A4) is a peptide consisting of an amino acid sequence with a sequence identity of at least 85% to the amino acid sequence of the peptide (A1) or (A2) and having hydrolysis activity. The sequence identity may be, for example, at least 90%, at least 95%, at least 96%, at least 97%, at least 98%, or at least 99%. The term "sequence identity" refers to the degree of identity between sequences to be compared with each other when they are aligned appropriately, and represents the occurrence ratio (%) of perfect match of amino acids between these sequences, for example. In the determination of the sequence identity, for example, the presence of a gap(s) in the sequences and the properties of the amino acids are taken into consideration. The alignment can be achieved by utilizing a freely-selected algorithm, for example. Specifically, it is possible to use homology search software such as Basic Local Alignment Search Tool (BLAST), BLAST-2, FASTA, Smith-Waterman, ALIGN, and Megasalin. The sequence identity can be calculated using a known homology search program such as those described above, for example. As a specific example, the sequence identity can be calculated with a homology algorithm BLAST (http://www.ncbi.nlm.nih.gov/BLAST/) provided by the National Center for Biotechnology Information (NCBI) using default parameters, for example. Regarding the sequence identity, the same applies hereinafter.

Next, as the catalytic peptide of the present invention, the peptides (B1) to (B4) will be described.

The peptide (B1) is a peptide consisting of Box B in a Tob/BTG protein.

In the peptide (B1), the amino acid sequence of Box B is not particularly limited, and may be the amino acid sequence of SEQ ID NO: 32, for example. In SEQ ID NO: 32, $Xaa_1$ is V or L, $Xaa_2$ is Q, E, S, or K, $Xaa_3$ is D or E, $Xaa_4$ is L or M, $Xaa_5$ is S or T, $Xaa_6$ is V, L, or I, $Xaa_7$ is V or I, $Xaa_8$ is F, Y, or C, $Xaa_9$ is E or R, $Xaa_{10}$ is S or C, $Xaa_{11}$ is Y or C, $Xaa_{12}$ is Q or R, and $Xaa_{13}$ is I or Y, for example.

Box B:

SEQ ID NO: 32

[Xaa₁]P[Xaa₂][Xaa₃][Xaa₄][Xaa₅][Xaa₆]W[Xaa₇]DP[Xaa₈]

[Xaa₉]V[Xaa₁₀][Xaa₁₁][Xaa₁₂][Xaa₁₃]GE

Specific examples of Box B of SEQ ID NO: 32 as the peptide (B1) include peptides consisting of amino acid sequences of SEQ ID NOs: 33 to 35.

TABLE 5

| BoxB | Sequence | SEQ ID NO |
|---|---|---|
| BTG1 | LPSELTLWVDPYEVSYRIGE | 33 |
| TOB1 | LPQDLSVWIDPFEVSYQIGE | 34 |
| BTG 3 | LPKELTLWVDPCRVCCRYGE | 35 |

The peptide (B2) is a peptide consisting of a partial region of the peptide (B1). The length of the peptide (B2) is as follows: the lower limit of the number of amino acid residues is, for example, 5, 7, or 9, the upper limit thereof is, for example, 19, 18, or 17, and the range thereof is, for example, from 5 to 19, from 5 to 18, or from 5 to 17.

Specific examples of the peptide (B2) include peptides consisting of amino acid sequences of SEQ ID NOs: 36 to 38.

TABLE 6

| BOX B BTG 1 8-20: | WVDPYEVSYRIGE | SEQ ID NO: 36 |
|---|---|---|
| BOX B Tob 1 8-20: | WIDPFEVSYQIGE | SEQ ID NO: 37 |
| BOX B BTG 3 8-20: | WVDPCRVCCRYGE | SEQ ID NO: 38 |

The peptide (B3) is a peptide that consists of an amino acid sequence obtained by deletion, substitution, addition, and/or insertion of one or more amino acids in the amino acid sequence of the peptide (B1) or (B2) and has hydrolysis activity. In the peptide (B3), the number of the deleted, substituted, added, and/or inserted amino acid residues is not particularly limited, and is, for example, 1 to 5, 1 to 3, 1, or 2.

The peptide (B4) is a peptide consisting of an amino acid sequence with a sequence identity of at least 85% to the amino acid sequence of the peptide (B1) or (B2) and having hydrolysis activity. The sequence identity may be, for example, at least 90%, at least 95%, at least 96%, at least 97%, at least 98%, or at least 99%.

Next, as the catalytic peptide of the present invention, the peptides (C1) to (C4) will be described.

The peptide (C1) is a peptide consisting of a C-terminal region or an intermediate region in a Tob/BTG protein.

Specific examples of the peptide (C1) include peptides consisting of amino acid sequences of SEQ ID NOs: 39 to 41.

TABLE 7

| Tob 1 198-221: | SNKVARTSPINLGLNVNDLLKQKA | SEQ ID NO: 39 |
|---|---|---|
| Tob 1 221-236: | AISSSMHSLYGLGLGS | SEQ ID NO: 40 |
| BTG 3 239-252: | DRNHWINPHMLAPH | SEQ ID NO: 41 |

The peptide (C2) is a peptide consisting of a partial region of the peptide (C1). The length of the peptide (C2) is as follows: the lower limit of the number of amino acid residues is, for example, 5, 7, or 9, the upper limit thereof is, for example, 23, 15, or 13, and the range thereof is, for example, from 5 to 23, from 5 to 15, or from 5 to 13.

The peptide (C3) is a peptide that consists of an amino acid sequence obtained by deletion, substitution, addition, and/or insertion of one or more amino acids in the amino acid sequence of the peptide (C1) or (C2) and has hydrolysis activity. In the peptide (C3), the number of the deleted, substituted, added, and/or inserted amino acid residues is not particularly limited, and is, for example, 1 to 5, 1 to 3, 1, or 2.

Specific examples of the peptide (C3) include peptides consisting of amino acid sequences of SEQ ID NOs: 42 and 43.

TABLE 8

| BTG 3 239-252 P246A: | DRNHWINAHMLAPH | SEQ ID NO: 42 |
|---|---|---|
| BTG 3 239-252 P246A P251A: | DRNHWINAHMLAAH | SEQ ID NO: 43 |

The peptide (C4) is a peptide consisting of an amino acid sequence with a sequence identity of at least 85% to the amino acid sequence of the peptide (C1) or (C2) and having hydrolysis activity. The sequence identity may be, for example, at least 90%, at least 95%, at least 96%, at least 97%, at least 98%, or at least 99%.

The catalytic peptide of the present invention can hydrolyze a protein or a peptide as a substrate, for example. The substrate is not particularly limited, and may be, for example, a amyloid beta (Aβ) protein or a fragment peptide thereof, a prion protein or a fragment peptide thereof, human matrix metalloprotease 7 (hMMP7) or a fragment peptide thereof, superoxide dismutase 1 (SOD1) or a fragment peptide thereof, a Tau protein such as Tau MBD or a fragment peptide thereof, or a crystalline such as αA-crystallin or a fragment peptide thereof.

The catalytic peptide of the present invention also can be used to hydrolyze an aggregated protein or a fragment peptide thereof, for example. It has been reported that the amyloid beta protein, the prion protein, and SOD1 cause Alzheimer's disease, Creutzfeldt-Jakob disease (CJD), and amyotrophic lateral sclerosis (ALS), respectively, when they aggregate. However, no enzyme proteins that can degrade these aggregated proteins have been reported yet. In contrast, the catalytic peptide of the present invention also can degrade the amyloid beta protein, prion protein, and further SOD1 even when they are in the aggregated state, for example. Thus, it can be said that the catalytic peptide of the present invention also is useful as a therapeutic agent for diseases caused by aggregated proteins, such as Alzheimer's disease, Creutzfeldt-Jakob disease (CJD), and further, neurological diseases such as amyotrophic lateral sclerosis (ALS), for example.

The catalytic peptide of the present invention further may have autodigestive properties, for example. In this case, when the catalytic peptide of the present invention is administered to a living organism as the above-described therapeutic agent (pharmaceutical preparation), the catalytic peptide is degraded gradually while exhibiting a catalytic function, for example, so that it is excellent in safety.

<Catalytic Peptide Reagent>

As described above, the catalytic peptide reagent of the present invention is a catalytic peptide reagent containing a catalytic molecule, wherein the catalytic molecule is the catalytic peptide of the present invention. The catalytic peptide reagent of the present invention is characterized in that it contains the catalytic peptide of the present invention as the catalytic molecule, and other configurations are by no means limited.

The catalytic peptide reagent of the present invention may further contain a molecule that is different from the catalytic peptide, and the molecule may be linked to the catalytic peptide, for example. The molecule may be, for example, a binding molecule that binds to a target to be degraded. The binding substance may be a protein or a peptide, for example. Specific examples of the binding substance include a ligand. The catalytic peptide reagent of the present invention preferably is configured so that, for example, the binding molecule that binds to the target is linked to the catalytic peptide. With this configuration, for example, the catalytic peptide reagent of the present invention is caused to bind to the target with the binding molecule, and the target can be degraded by the catalytic peptide contained in the catalytic peptide reagent.

<Degradation Method>

As described above, the degradation method of the present invention is a method for degrading a protein or a peptide, including the step of: treating a substrate with the catalytic peptide of the present invention, wherein the substrate is a protein or a peptide. The degradation method of the present invention is characterized in that it uses the catalytic peptide, and other steps, conditions, etc. are by no means limited. The substrate may be the above-described target, for example.

The conditions for the above-described treatment step are not particularly limited. The reaction temperature is, for example, room temperature to 37° C., and the reaction pH is, for example, 6.5 to 8. In the treatment step, the treatment may be performed in the presence of albumin, for example. The substrate is not particularly limited, and the above description regarding the substrate also applies to the substrate in the degradation method of the present invention.

EXAMPLES

Example 1

(1) Examination of Hydrolysis Activity

The present example examined whether a synthetic peptide JAL has hydrolysis activity against synthetic peptides derived from the prodomain of human matrix metalloprotease 7 (hMMP7).

The following JAL was used as a hydrolytic peptide, and hMMP7 42-50 or hMMP7 26-50 was used as a substrate.

```
JAL (Tob1):
KYEGHWYPEKPYKGSGFRCIHI hMMP7 42-50:
FYLYDSETK hMMP7 26-50:
GMSELQWEQAQDYLKRFYLYDSETK
```

First, to a buffer solution (Tris-HCl, pH 6.5, final concentration: 100 mmol/l), JAL (final concentration: 0.2 mmol/l) and the fragment peptide of hMMP7 (final concentration 0.05 mmol/l) were added. This reaction solution was incubated at 37° C. for 14 days or for 16 days. Thereafter, the reaction solution was subjected to HPLC, and the peaks of JAL and the fragment peptide of hMMP7 were examined. HPLC was performed under the following conditions.

Column: SHISEIDO CAPCELL PAK C18 MGII (4.6 mm ID×150 mm)
Temperature: 40° C.
Wavelength: 220 nm
Concentration gradient: 0.1% TFA-containing 0%-70% $CH_3CN$, 15 min
Detector: Photodiode-array Then, in HPLC, aliquots of the peaks were collected (each 20 μl), and fragment identification was performed by mass spectrometry (ABI QSTAR Elite system) (referred to as "MS" hereinafter). MS was performed by a flow injection method under the following conditions.

MS: Positive ion mode
Ion spray voltage: 3500 to 5500 V
Ion source temperature: 140° C. to 400° C.
Solvent: 0.1% HCOOH-containing 70% $CH_3CN$ In experiments to be described below, the measurement of hydrolysis activity was performed under the same conditions as in the above, unless otherwise stated.

Figure 2:
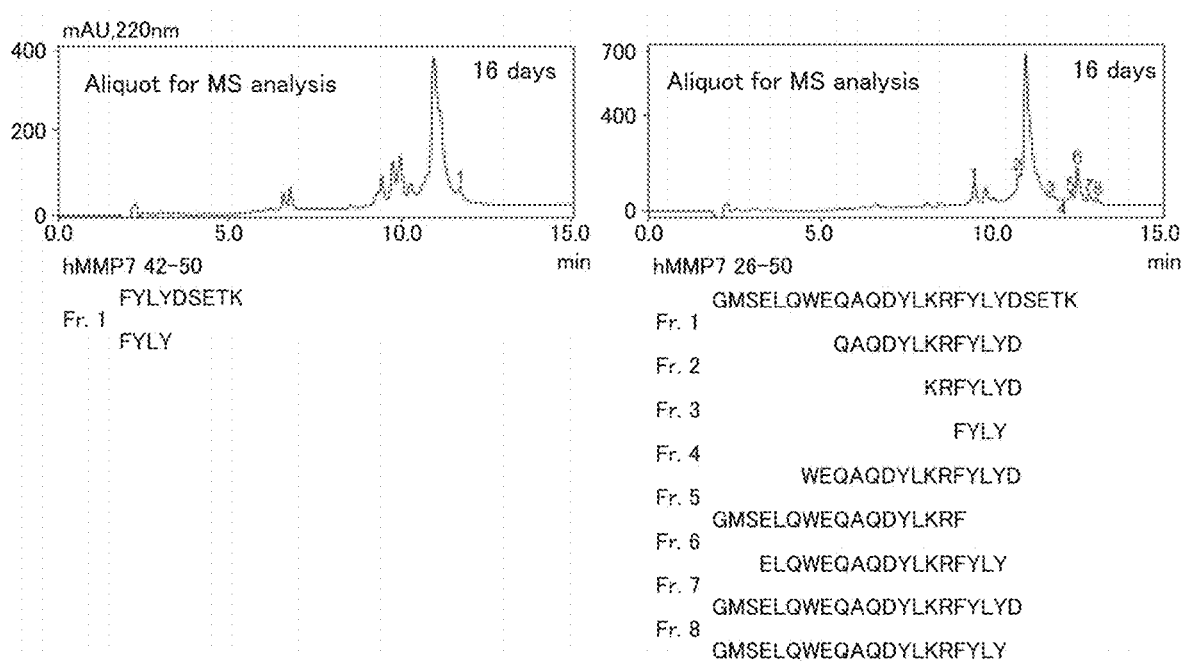
FIG. 2 shows chromatograms showing the hydrolysis activity of the catalytic peptide, and the sequences of fragments obtained by degradation.

The results obtained are shown in FIGS. 1 and 2. FIG. 1 shows the results of HPLC obtained after a lapse of 0 days and 14 days from the start of the reaction. As can be seen in FIG. 1, the peaks of hMMP7 42-50 and hMMP7 26-50 decreased, which demonstrates that JAL has activity against hMMP7 42-50 and hMMP7 26-50. Further, from the fact that the peak of JAL itself also decreased, it is considered that autodigestion of JAL occurred. FIG. 2 shows the results of the fragment identification by MS obtained after a lapse of 16 days from the start of the reaction, and also shows the sequences of fragments obtained by degradation. As can be seen in FIG. 2, the substrates were cleaved at a plurality of sites.

(2) Consideration of Optimal pH

Figure 3:
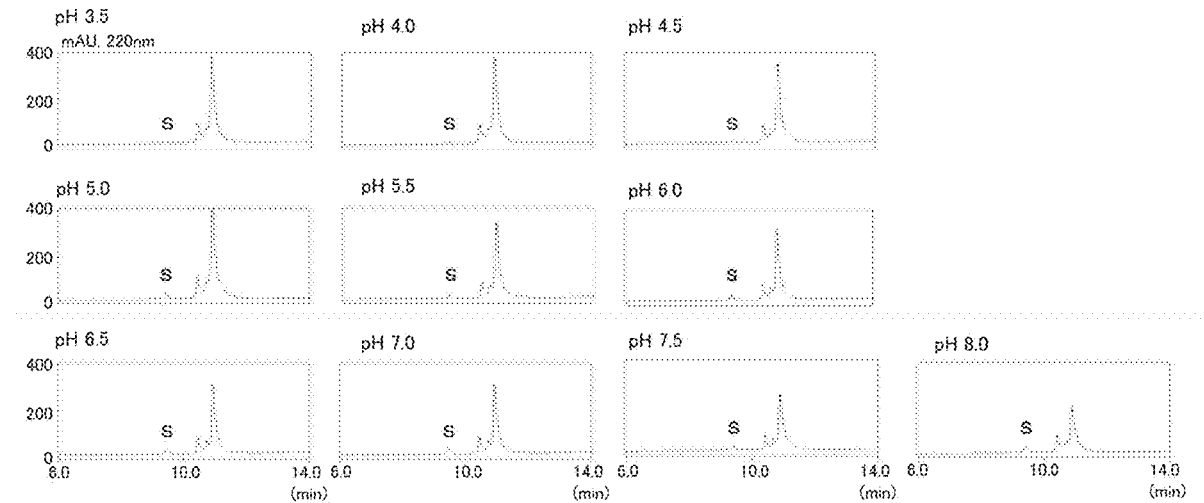
FIG. 3 shows chromatograms showing the influence of pH on the hydrolysis activity of the catalytic peptide.

The present experiment was conducted to consider an optimal pH for activity of a hydrolytic peptide using JAL as the hydrolytic peptide and hMMP7 1-42 as a substrate. The measurement of activity was performed in the same manner as in the above item (1), except that the pH of the reaction solution was adjusted so as to vary within the pH range from 3.5 to 8.0 in increments of 0.5 and the reaction solution was incubated for 5 days. The pH of the reaction solution was adjusted using an acetate buffer solution in the pH range from 3.5 to 6.0 and using a Tris-HCl buffer solution in the pH range from 6.5 to 8.0. In either case, the final concentration was set to 150 mmol/l. As a result, it was found that JAL exhibited activity in the pH range from 3.5 to 6.0 (FIG. 3). In the pH range from 6.5 to 8.0, the results obtained were the same as that obtained after a lapse of 0 days from the start of the reaction.

```
hMMP7 1-42:
                                        (SEQ ID NO: 49)
MRLTVLCAVCLLPGSLALPLPQEAGGMSELQWEQAQDYLKRF
```

Example 2

(1) Examination of Hydrolysis Activity

The present example examined whether JAL has hydrolysis activity against fragment peptides derived from superoxide dismutase 1 (SOD1).

The measurement of hydrolysis activity was performed in the same manner as in the item (1) in Example 1, except that: the above-described JAL was used as the hydrolytic peptide; SOD1 2-38, SOD1 12-38, SOD1 53-70, SOD1 115-154 or SOD1 2-12 shown below was used as the substrate; the pH of a reaction solution was set to 6.5 or 7.5; and the incubation time of the reaction was set to 0 days, 3 days, or 4 days.

```
SOD1 2-38:
ATKAVCVLKGDGPVQGIINFEQKESNGPVKVWGSIKG

SOD 12-38:
DGPVQGIINFEQKESNGPVKVWGSIKG

SOD1 53-70:
DNTAGCTSAGPHFNPLSR

SOD 115-154:
GRTLVVHEKADDLGKGGNEESTKTGNAGSRLACGVIGIAQ

SOD1 2-12:
ATKAVCVLKGD
```

Figure 4:
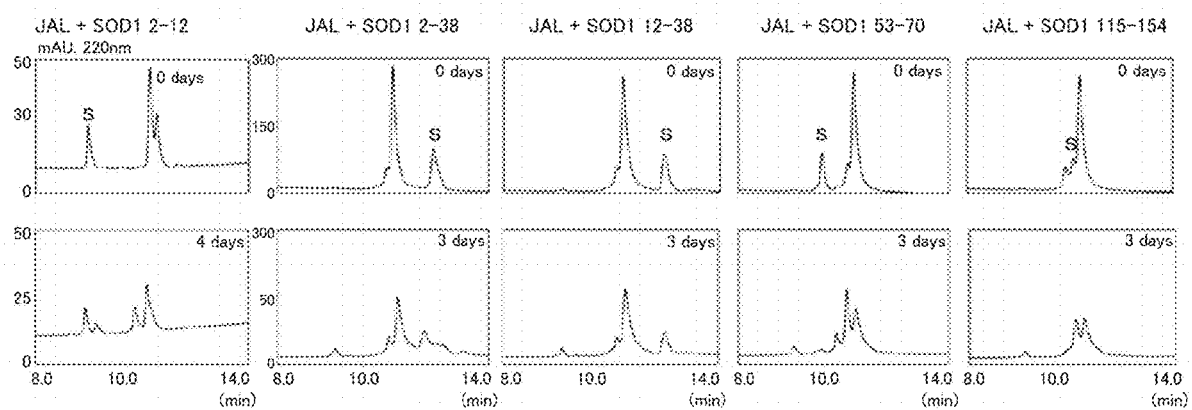
FIG. 4 shows chromatograms showing the hydrolysis activity of the catalytic peptide against SOD1.

The results obtained are shown in FIGS. 4 and 5. FIG. 4 shows the result of the HPLC after a lapse of 0 days, 3 days, or 4 days from the start of the reaction. As can be seen in FIG. 4, it was found that JAL has activity against SOD1 2-38, SOD1 12-38, SOD1 53-70, and SOD1 2-12. In particular, JAL exhibited strong activity against SOD1 53-70 and SOD1 2-38. In contrast, JAL did not exhibit activity against SOD1 115-154. FIG. 5 shows the results of fragment identification by MS. As can be seen in FIG. 5, in SOD1 2-38 and SOD1 2-12, a plurality of sites indicated with arrows were cleaved by JAL. Further, in peptide fragments derived from SOD1 2-38, S—S bonds formed between Cys residues were observed.

(2) Consideration of Buffer Solution (Reaction Solution)

The present experiment was conducted to consider which buffer solution is suitable as a reaction solution, using JAL as a hydrolytic peptide and SOD1 2-38 as a substrate. The measurement was performed in the same manner as in the above item (1), except that, as a buffer solution, a Tris buffer solution (Tris-HCl, pH 6.5, final concentration: 100 mmol/l) or an assay buffer solution (50 mmol/l Tris-HCl, pH 7.5, 150 mmol/l NaCl, 10 mmol/l $Ca^{2+}$, 5 µmol/l $Zn^{2-}$, 0.06% Briji35, and 0.02% $NaN_3$) was used, and the incubation time was set to 0 days, 1 day, or 3 days. As a control, physiological saline (0.9 w/v %) was used instead of the buffer solution. As a result, in the case where the assay buffer solution was used, cleavage by JAL was observed earlier as compared with the case where the Tris buffer solution was used (FIG. 6). In the case where the physiological saline was used, JAL did not exhibit activity. Accordingly, it is considered that the use of a buffer solution is necessary to allow JAL to exhibit hydrolysis activity. Also, it is considered that physiological saline is suitable for storage of JAL before use, for example.

(3) Consideration of Concentration

Figure 7:
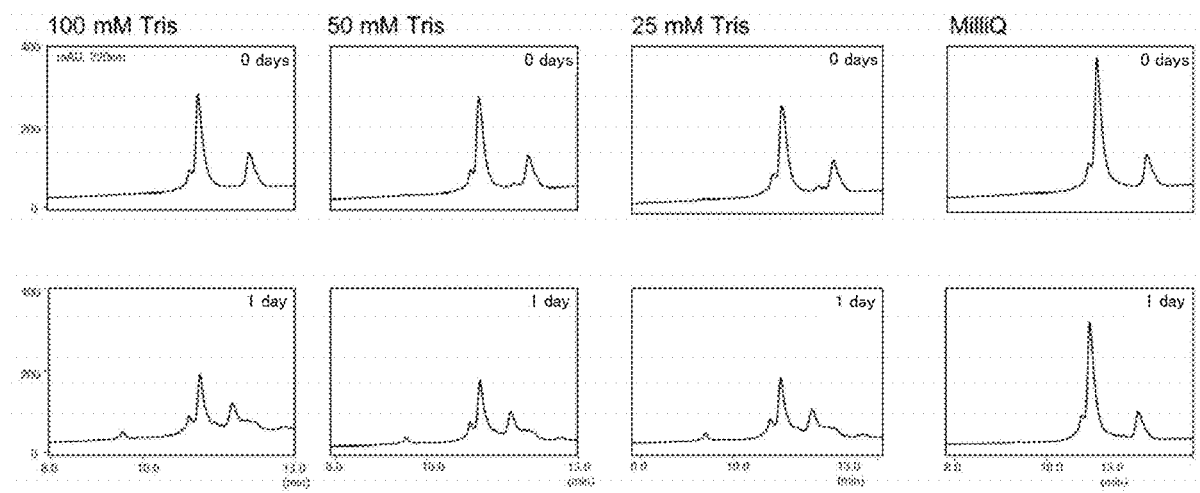
FIG. 7 shows chromatograms showing the influence of the concentration of a buffer solution on the hydrolysis activity of the catalytic peptide.

Subsequently, the measurement was performed in the same manner as in the above item (2), except that the concentration of the Tris buffer solution was set to various values and the incubation time was set to 0 days, 1 day, or 4 days. As a result, JAL did not exhibit activity when only Milli-Q water was used (0 mmol/l), whereas, when the Tris buffer solution was used, JAL exhibited activity regardless of the concentration of the Tris buffer solution (FIG. 7).

(4) Consideration of Optimal pH

Figure 8:
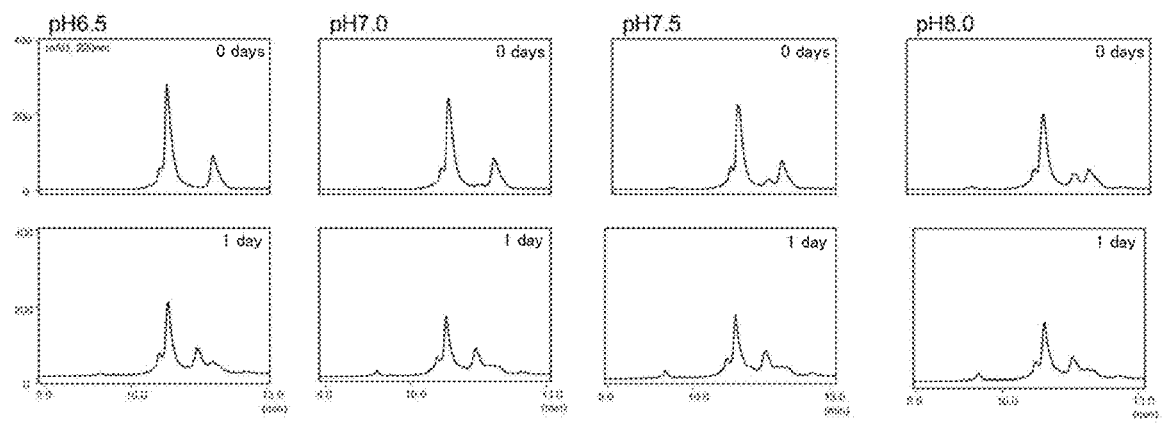
FIG. 8 shows chromatograms showing the optimal pH for the catalytic peptide.

Next, an experiment was conducted to consider an optimal pH for activity using JAL as the hydrolytic peptide and SOD1 2-38 as a substrate. The measurement was performed in the same manner as in the above item (1), except that the pH of a reaction solution was adjusted so as to vary within the pH range from 6.5 to 8.0 in increments of 0.5 and the incubation time was set to 0 days or 1 day. As a result, JAL exhibited activity at all the pH values, and there was no difference in activity among these pH values (FIG. 8). From this result, it is considered that, when the hydrolytic peptide is used in the body, the activity of the hydrolytic peptide is not influenced by local pH variation.

(5) Examination of Metal Requirements

Figure 9:
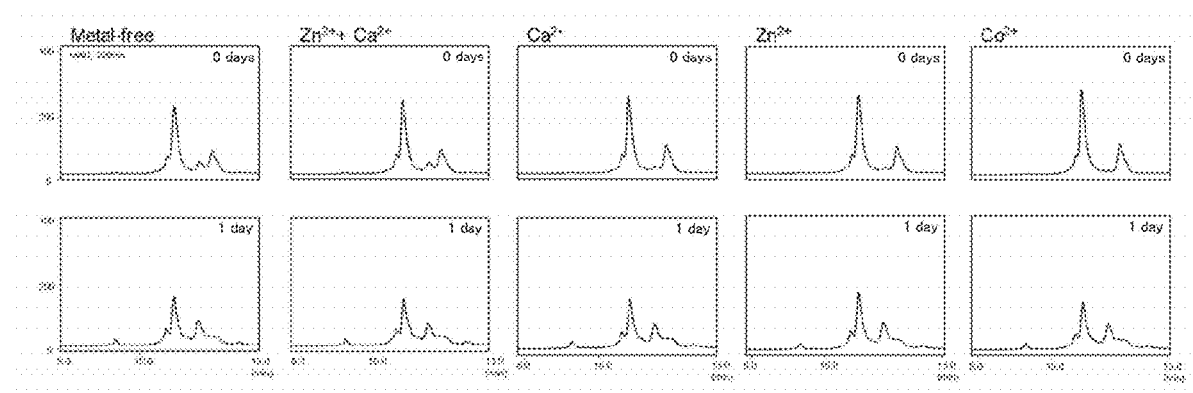
FIG. 9 shows chromatograms obtained in order to examine the influence of metals on the hydrolysis activity of the catalytic peptide.

Further, the metal requirement of a hydrolytic peptide for exhibiting activity was examined using JAL as the hydrolytic peptide and SOD1 2-38 as a substrate. Metal ions to be added to a reaction solution were $Zn^{2+}$, $Ca^{2+}$, $Co^{2+}$, or combinations thereof. The concentrations of the metal ions in the respective reaction solutions were as follows: 10 mmol/l for $Ca^{2+}$; and 5 µmol/l for the other metal ions. Then, the measurement was performed regarding the respective reaction solutions in the same manner as in the above item (1), except that the reaction solutions with or without the metal ions were provided and the incubation time was set to 0 days or 1 day. As a result, JAL exhibited activity regardless of the presence or absence of the metals, and there was no difference due to the presence or absence of the metal ions ($Zn^{2-}$, $Co^{2+}$, $Ca^{2+}$) (FIG. 9).

Example 3

The present example examined whether mutants of JAL have hydrolysis activity.

(1) Activity Against SOD1 2-38 and SOD1 2-12

Figure 10:
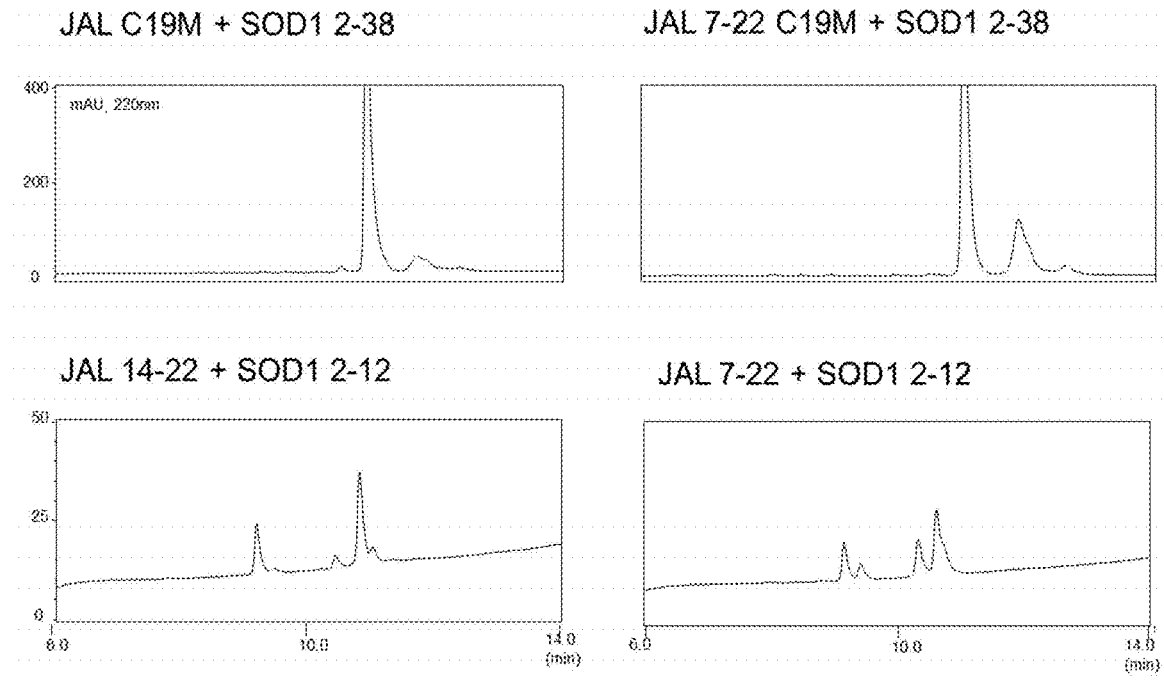
FIG. 10 shows chromatograms showing the hydrolysis activity of catalytic peptides.

The measurement of hydrolysis activity was performed in the same manner as in the item (1) in Example 1, except that each of the following mutants of JAL, namely, JAL 7-22, JAL 14-22, JAL 1-22 C19M, and JAL 7-22 C19M, was used as the hydrolytic peptide and the SOD1 2-38 or SOD1 2-12 was used as the substrate. In JAL 1-22 C19M and JAL 7-22 C19M, Cys residues contained in JAL form S—S bonds during a reaction, and this makes fragment analysis difficult. On this account, JAL 1-22 and JAL 7-22 were modified so as to substitute Cys residues by Met. As a result, JAL 7-22, JAL 1-22 C19M, and JAL 7-22 C19M exhibited hydrolysis activity (FIG. 10).

```
JAL 7-22:
YPEKPYKGSGFRCIHI

JAL 14-22:
GSGFRCIHI

JAL 1-22 C19M:
KYEGHWYPEKPYKGSGFRMIHI

JAL 7-22 C19M:
YPEKPYKGSGFRMIHI
```

(2) Activity Against Aβ1-20

Figure 11:
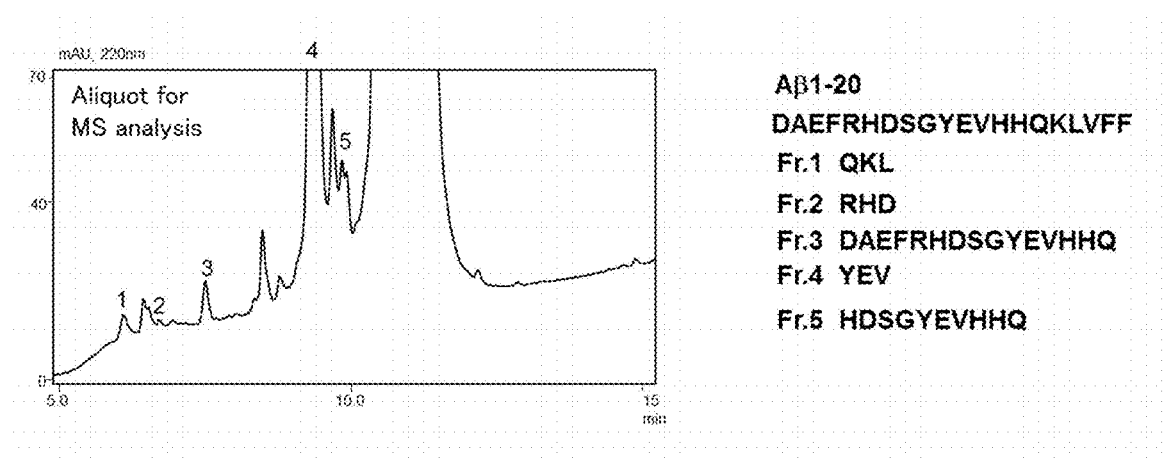
FIG. 11 shows a chromatogram showing the hydrolysis activity of a catalytic peptide, and the sequences of fragments obtained by degradation.

The measurement of activity was performed in the same manner as in the above item (1), except that JAL was used as the hydrolytic peptide and Aβ1-20 shown below was used as the substrate. As a result, it was found that JAL has activity against Aβ1-20 (FIG. 11).

```
Aβ1-20: sequence
DAEFRHDSGYEVHHQKLVFF
```

(3) Consideration of Buffer Solution (Reaction Solution)

Figure 12:
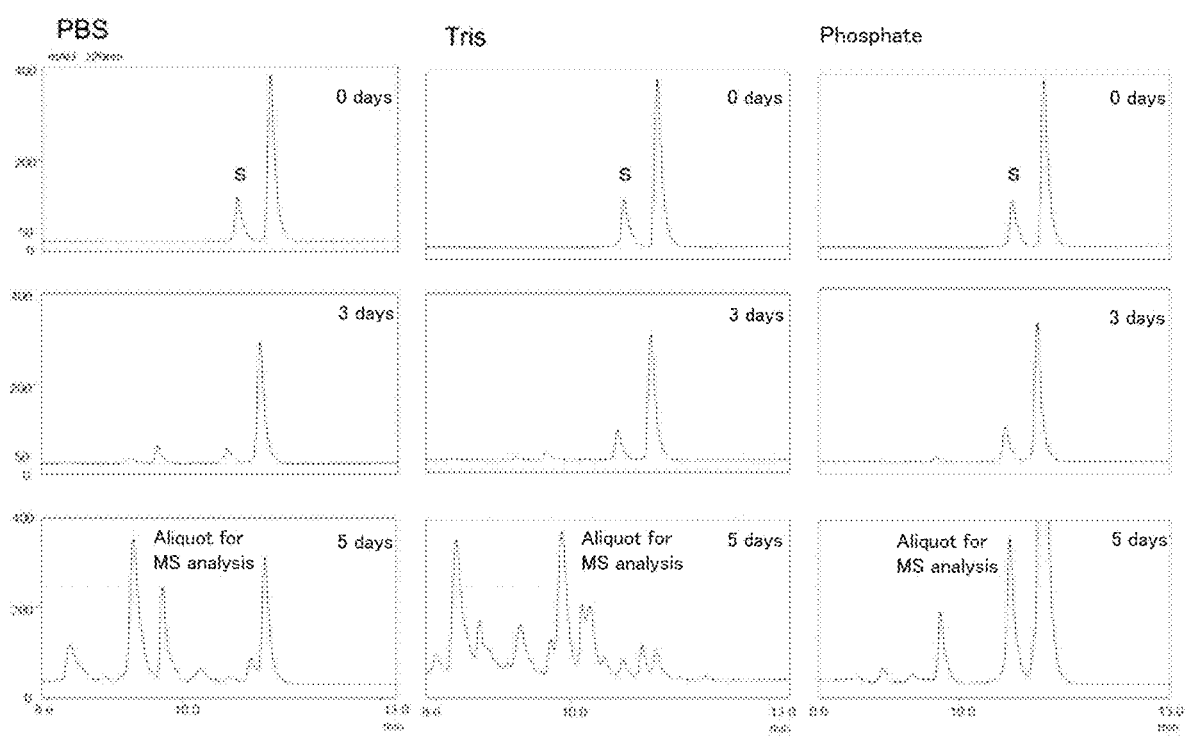
FIG. 12 shows chromatograms obtained in order to examine the influence of buffer solutions on the hydrolysis activity of the catalytic peptide.

The present experiment was conducted to consider which buffer solution is suitable, using JAL as a hydrolytic peptide and Aβ1-20 as a substrate. The measurement was performed in the same manner as in the above item (2), except that PBS, a Tris buffer solution, or a phosphate buffer solution was used as the buffer solution and the incubation time was set to 0 days, 3 days, or 5 days. As a result, JAL exhibited activity in PBS (pH 7.4) and the Tris buffer solution (50 mmol/l, pH 7.5) (FIG. 12). On the other hand, JAL did not exhibit activity in the phosphate buffer solution. This demonstrates that, by using PBS or a Tris buffer solution as a buffer solution, the activity of JAL is exhibited sufficiently. In experiments to be described below, the measurement was performed using PBS, which is suitable for administration to the body.

(4) Examination of Activity of Tob/BTG

The measurement of activity was performed in the same manner as in the above item (1), except that JAL (Tob1) 7-22 CM, JAL (Tob1) 7-22, Tob2 7-22, BTG1 7-22, BTG2 7-22, BTG3 7-22, or BTG4 7-22 was used as the hydrolytic peptide and Aβ1-20 or Aβ11-29 was used as the substrate. Further, any change in activity caused by addition of human serum albumin (HSA, Wako Pure Chemical Industries, Ltd., final concentration 0.025%) also was measured.

```
JAL (Tob1) 7-22CM:
YPEKPYKGSGFRMIHI

Tob2 7-22:
YPEKPLKGSGFRCVHI

BTG1 7-22:
FPEKPCKGSGYRCIRI

BTG2 7-22:
FPEKPSKGSGYRCIRI

BTG3 7-22:
YPEKPSKGQAYRCIRV

BTG4 7-22:
HSDCPSKGQAFRCIRI
```

The results obtained are shown in FIG. 13. In FIG. 13, 1-19, 1-18, etc. indicate regions of fragments obtained by degradation. Each of the mutants exhibited activity against Aβ1-20 and Aβ11-29. Further, comparison of the chromatograms revealed that the activity was enhanced by adding HSA.

(5) Activity Against Fragment Peptides Derived from Human Prion Protein (PrP)

Next, the activity of each of the peptides was measured using PrP 175-189 shown below as a substrate. Further, in the measurement using Tob2 7-22 or BTG3 7-22 as the hydrolytic peptide, a change in activity caused by further adding $Cu^{2+}$ to HSA was measured. The measurement of hydrolysis activity was performed in the same manner as in the above item (1). As a result, Tob2, BTG1, BTG3, and BTG4 exhibited activity against PrP 175-189. Further, Tob2 7-22 and BTG3 7-22 exhibited activity after the addition of $Cu^{2+}$ (FIG. 14). In the reaction system containing $Cu^{2+}$, S—S bonds between fragment peptides derived from PrP 175-189 were observed.

```
PrP 175-189:
FVHDCVNITIKQHTV
```

(6) Activity Against Aβ Peptides

Next, the measurement of activity was performed in the same manner as in the above item (1), except that each of various mutants of JAL was used as the hydrolytic peptide and Aβ1-20 or the following Aβ11-29 was used as a substrate (FIG. 15). As a result, JAL (Tob1) 7-22 C19M, JAL (Tob1) 12-18, JAL (Tob1) 12-18 S15A, and JAL (Tob1) 14-18 exhibited activity against Aβ1-20. Further, JAL (Tob1) 7-22 Y7A C19M I22A, JAL (Tob1) 9-20 C19M, JAL (Tob1) 12-22 C19M I22A, JAL (Tob1) 12-20 C19M, and JAL (Tob1) 12-20 Y12A C19M exhibited activity against Aβ11-29.

```
Aβ11-29:
EVHHQKLVFFAEDVGSNKG
```

(7) Influence of Inhibitor on Autodigestion

Figure 16:
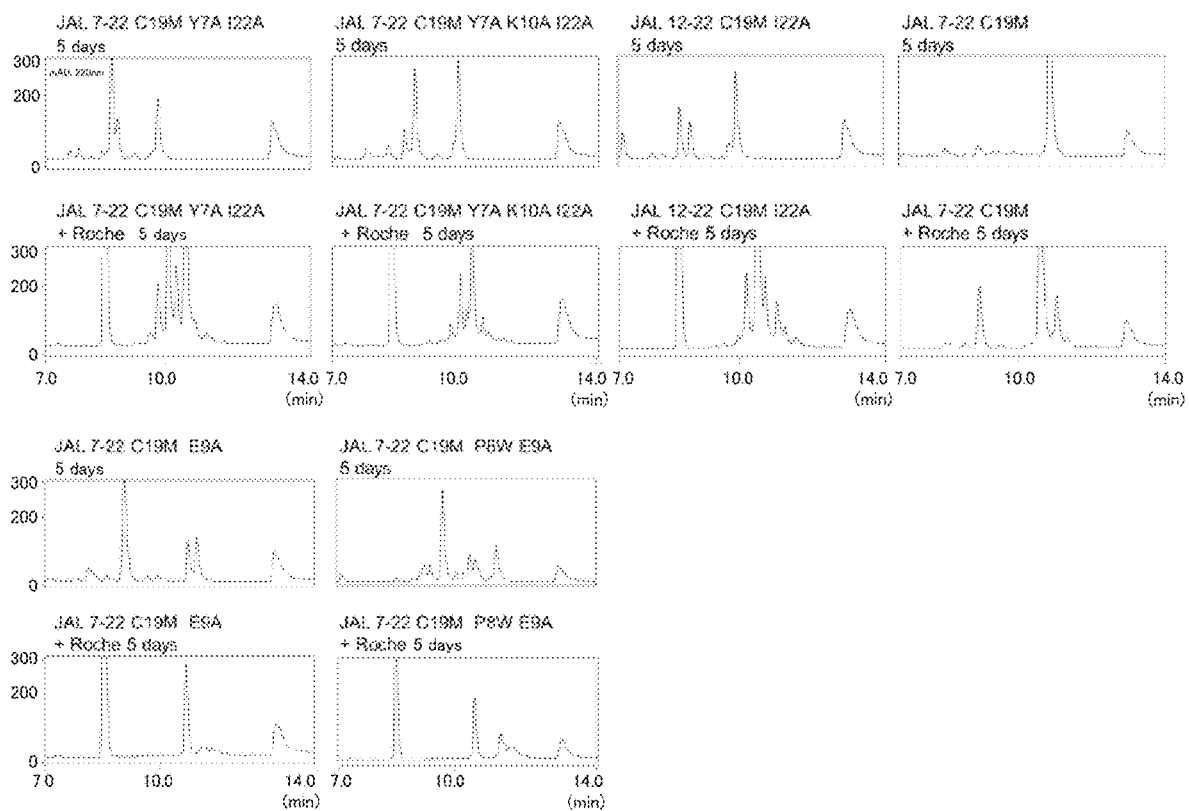
FIG. 16 shows chromatograms showing inhibition of autodigestion of catalytic peptides by a protease inhibitor.

Next, the mechanism of autodigestion was examined using various mutants of JAL as hydrolytic peptides. To a reaction solution containing each of the mutants of JAL, a protease inhibitor (trade name: Roche cOmplete, Roche) was added to cause a reaction. One tablet of the protease inhibitor was dissolved in 1 ml of Milli-Q water, and then, 50 μl of the resultant mixture was added to the reaction solution. The measurement of hydrolysis activity was performed in the same manner as in the above item (1). As a result, the autodigestion of all the peptides subjected to the measurement was inhibited (FIG. 16).

Example 4

The present example was conducted to consider reaction conditions suitable for the hydrolysis activity of JAL.

(1) Influence of Organic Solvent

Figure 17:
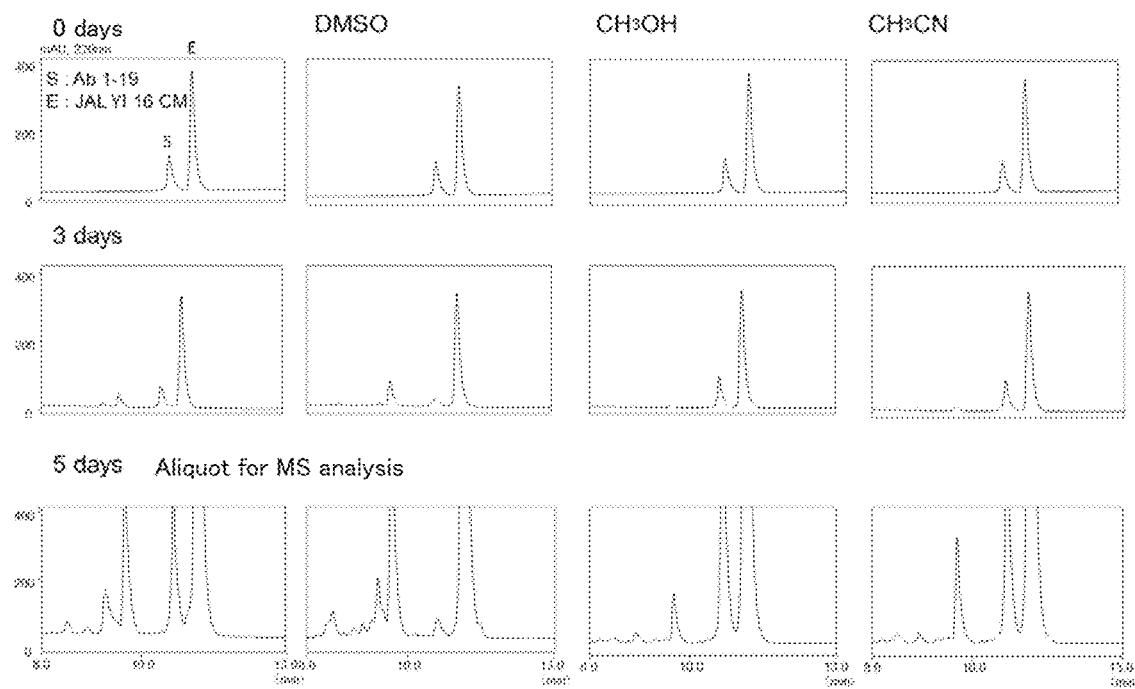
FIG. 17 shows chromatograms obtained in order to examine the influence of organic solvents on the hydrolysis activity of a catalytic peptide.

The influence of organic solvents was examined using JAL 1-22 C19M as a hydrolytic peptide and Aβ1-19 as a substrate. The measurement of activity was performed in the same manner as in the item (1) in Example 1, except that DMSO, $CH_3OH$, or $CH_3CN$ was added to a reaction solution at a final concentration of 10% and the incubation time was set to 0 days, 3 days, or 5 days. As a result, JAL 1-22 C19M exhibited activity when DMSO was added to the reaction solution (FIG. 17). On the other hand, JAL 1-22 C19M did not exhibit activity when $CH_3OH$ or $CH_3CN$ was added. These results demonstrate that, by dissolving a poorly-soluble peptide in DMSO, it is possible to use the poorly-soluble peptide with no influence to the hydrolysis activity of JAL. In experiments to be described below, a poorly-soluble peptide was used in the state of being dissolved in DMSO.

(2) Influence of Albumin

Figure 18:
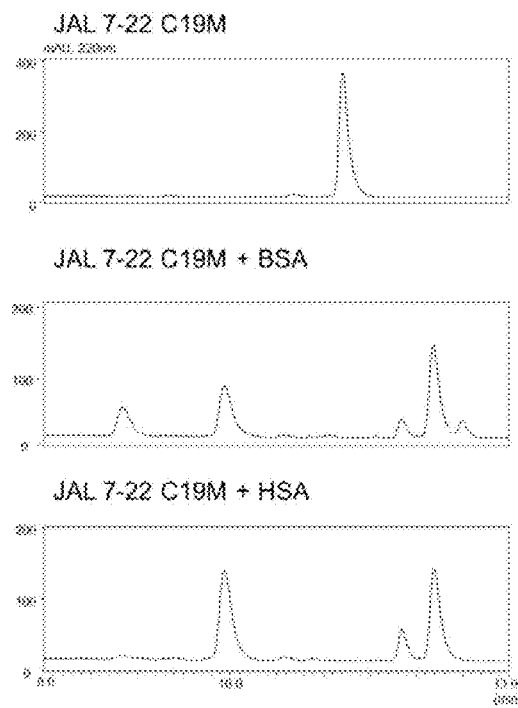
FIG. 18 shows chromatograms obtained in order to examine the influence of albumin on the hydrolysis activity of the catalytic peptide.

The measurement of activity was performed in the same manner as in the above item (1), except that JAL 7-22 C19M was used as the hydrolytic peptide, and bovine serum albumin (BSA, Wako Pure Chemical Industries, Ltd., final concentration: 0.025%) or HSA (Wako Pure Chemical Industries, Ltd., final concentration: 0.025%) as the substrate. As a result, cleavage by JAL was not observed when either HSA or BSA was used (FIG. 18). On the other hand, by adding either HSA or BSA to the reaction solution, autodigestion of JAL 7-22 C 19M was enhanced. From these results, it is considered that the activity of JAL 7-22 C19M was enhanced by adding HSA or BSA. Since serum albumin is present in the body, it is considered that the hydrolytic peptide is suitable for use in the body. In experiments to be described below, the hydrolysis activity of JAL was measured in a reaction solution containing HSA.

(3) Influence of Inhibitor on Autodigestion

The mechanism of autodigestion was examined using JAL 7-22 C19M as a hydrolytic peptide. The measurement of activity was performed in the same manner as in the above item (1), except that HSA was added to a reaction solution containing JAL 7-22 C19M, and a protease inhibitor (trade name: Roche cOmplete), E64, Aprotinin, AEBSF, EDTA (0.4 mmol/l) or Pepstatin A was further added thereto.

Figure 19:
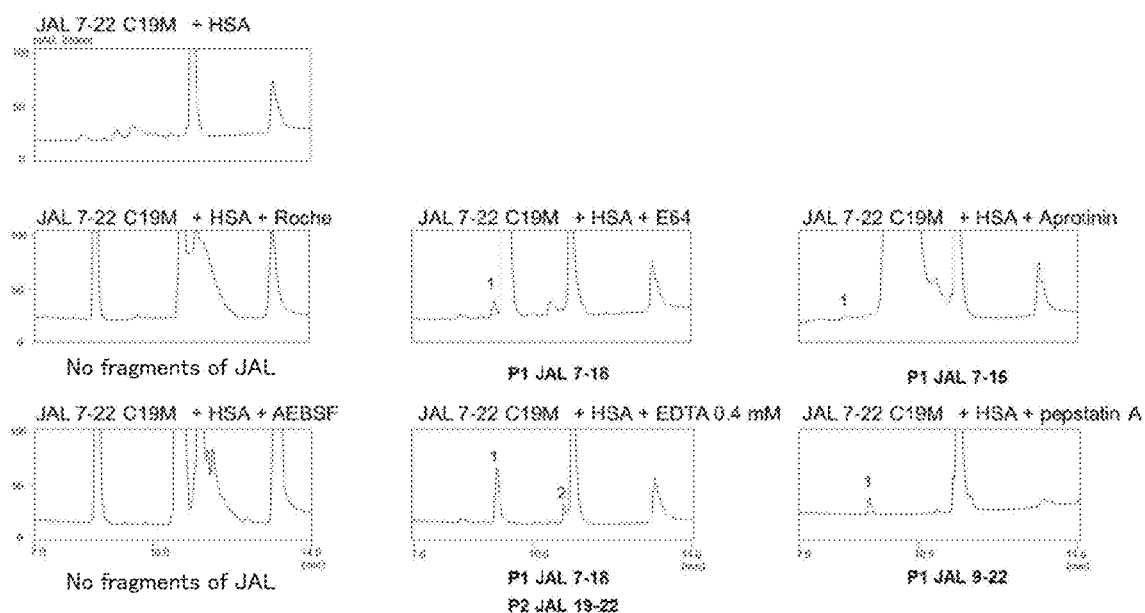
FIG. 19 shows chromatograms showing inhibition of autodigestion of the catalytic peptide by a protease inhibitor.

As a result, in the sample containing Roche cOmplete or AEB SF, fragments generated by autodigestion disappeared (FIG. 19).

(4) Consideration of Optimal Concentration

Figure 20:
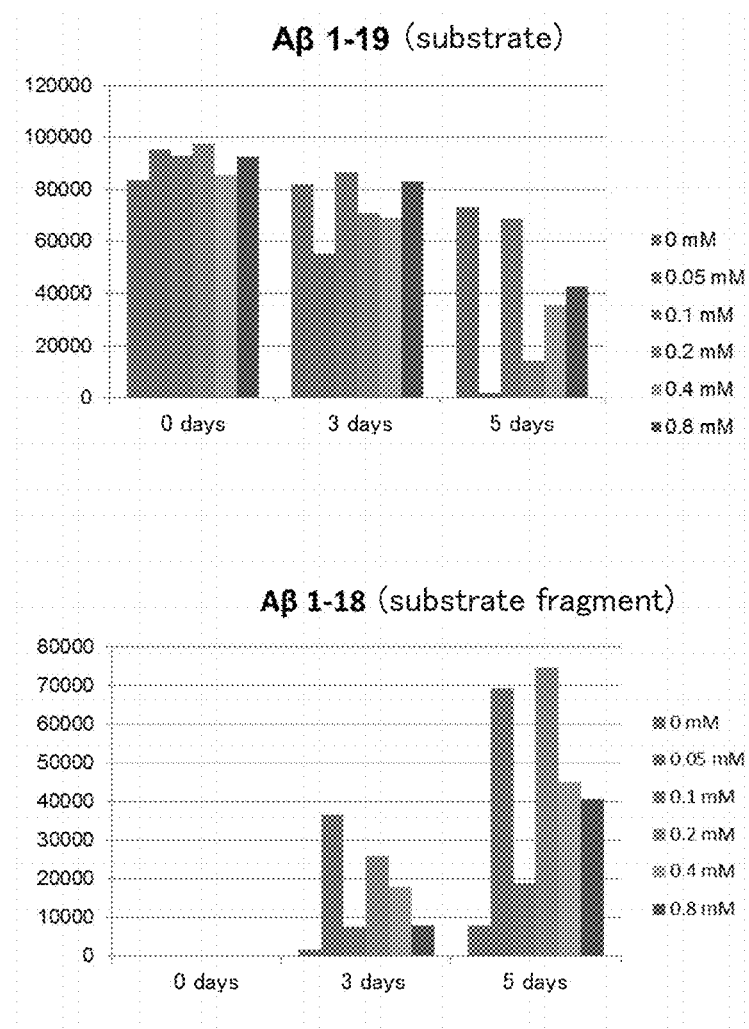
FIG. 20 shows graphs showing an optimal concentration of the catalytic peptide.

The present experiment was conducted to consider an optimal concentration of a hydrolytic peptide relative to a substrate, using JAL 7-22 C19M as the hydrolytic peptide and Aβ1-19 as the substrate. The measurement of activity was performed in the same manner as in the above item (1), except that the incubation time was set to 0 days, 3 days, or 5 days. The results obtained are shown in FIG. 20. In FIG. 20, the respective bars regarding each number of days indicate, from the left, the results obtained when the concentration of the hydrolytic peptide was 0, 0.05, 0.1, 0.2, 0.4, and 0.8 mmol/l (mM). As can be seen in FIG. 20, under the conditions where the ratio between the substrate (Aβ1-19) and the peptide was 1:1 (final peptide concentration: 0.05 mmol/l) and where the ratio between the same was 1:4 (final peptide concentration: 0.2 mmol/l), the substrate was decreased (the upper graph) and the digestion product (Aβ1-18) was increased (the lower graph). From these results, it was found that JAL 7-22 exhibits strong activity at these concentration ratios. Further, when the concentration of the peptide was high, the level of the activity of JAL 7-22 was lowered.

```
Aβ1-19:
DAEFRHDSGYEVHHQKLVF
```

(5) Activity Against Various Fragments of Aβ

The measurement of activity was performed in the same manner as in the above item (1), except that JAL 12-20 C19M was used as the hydrolytic peptide and Aβ11-29 was used as the substrate. As a result, JAL 12-20 C19M exhibited strong activity against Aβ11-29 (FIG. 21).

(6) Consideration of the Type of Protease

The mechanism of autodigestion was examined using JAL 12-20 C19M as a hydrolytic peptide and Aβ11-29 as a substrate. The measurement of activity was performed in the same manner as in the above item (1), except that a protease inhibitor (trade name: Roche cOmplete or AEBSF) was added to a reaction solution containing JAL 12-20 C19M and the incubation time was set to 0 days or 1 day. As a result, the autodigestion was inhibited by AEBSF, which is a serine protease inhibitor (FIG. 22). From this result, it is considered that JAL may be a serine protease-like peptide.

Example 5

The present example examined whether mutants of JAL have hydrolysis activity against Aβ.

(1) Examination of Activity Against Aβ

Figure 23:
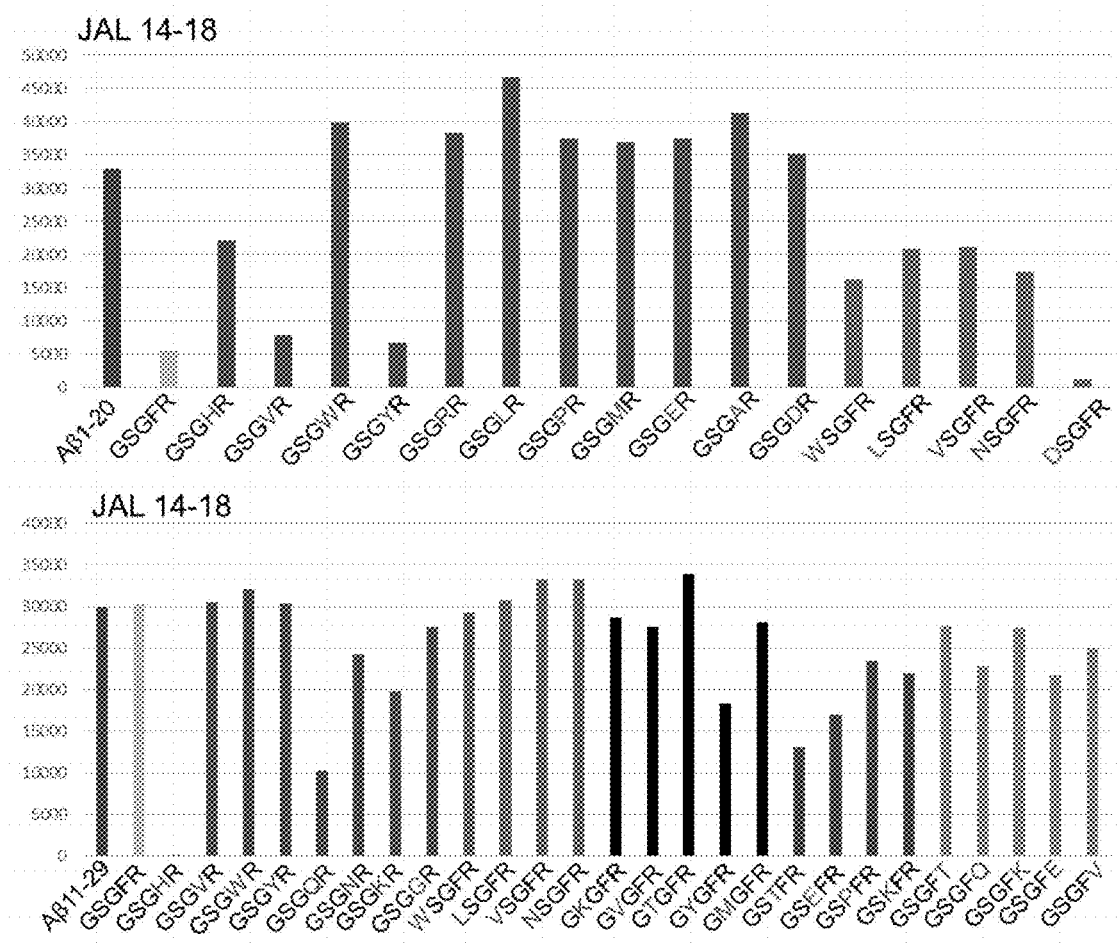
FIG. 23 shows graphs showing the hydrolysis activity of catalytic peptides.

It had been confirmed that JAL 14-18 (sequence: GSGFR) has activity similar to that of JAL (item (6) in Example 3). Thus, JAL 14-18 and mutants thereof were synthesized, and the measurement of activity was performed using them as hydrolytic peptides. As a substrate, Aβ1-20 (the upper graph) or Aβ11-29 (the lower graph) was used. The measurement of activity was performed in the same manner as in the item (1) in Example 1. As a result, GSGFR, GSGVR, GSGYR, and DSGFR exhibited strong activity against Aβ1-20, whereas GSGHR and GSGQR exhibited strong activity against Aβ11-29 (FIG. 23). From these results, it was found that the substrate specificity changes owing to the difference in a single amino acid residue.

(2) Examination of Activity Against Solid (Insoluble) Aβ1-42

Figure 24:
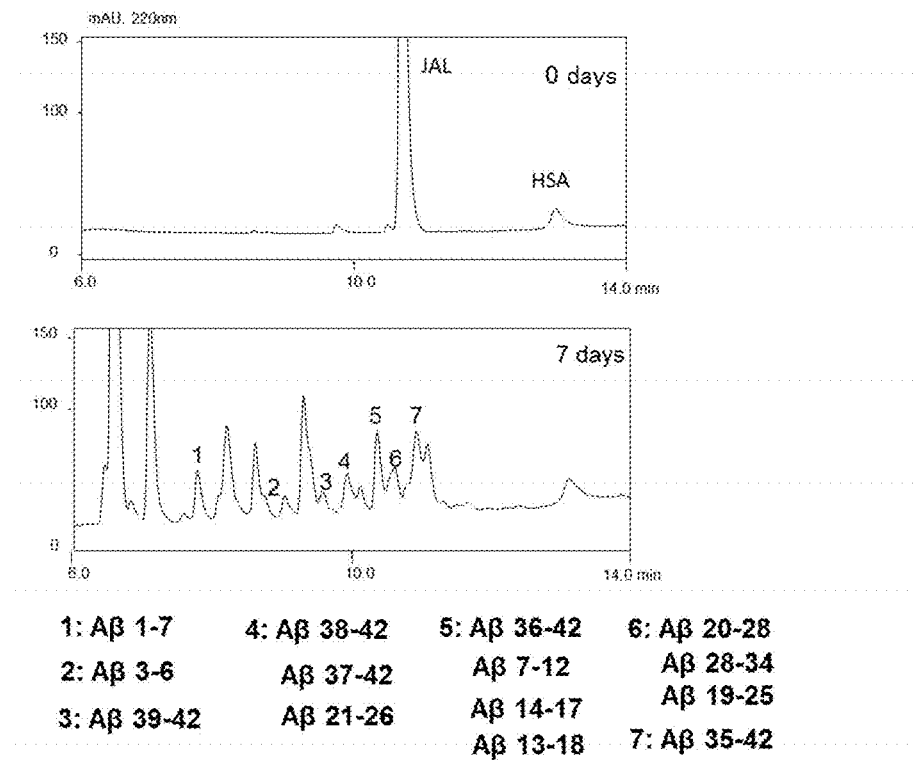
FIG. 24 shows chromatograms showing the hydrolysis activity of a catalytic peptide against solid Aβ1-42, and fragments obtained by degradation.

The measurement of activity was performed in the same manner as in the above item (1), except that JAL 12-20 C19M was used as the hydrolytic peptide, synthesized solid (insoluble) Aβ1-42 was used as the substrate, and the incubation time was set to 0 days or 7 days. As a result, Aβ1-42, which is an insoluble solid, was cleaved by JAL 12-20 C19M (FIG. 24). From this result, it is speculated that the hydrolytic peptide also can degrade Aβ1-42 present in vivo as an insoluble aggregate.

(3) Examination of Activity Against Soluble Aβ

Figure 25:
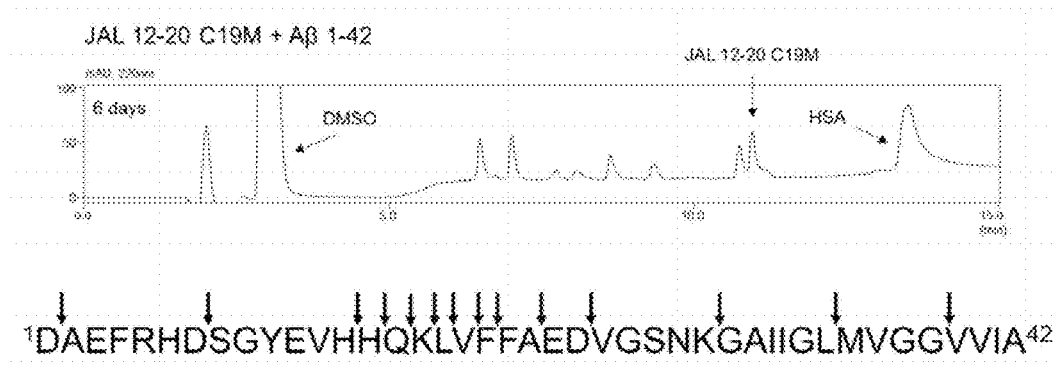
FIG. 25 shows a chromatogram showing the hydrolysis activity of the catalytic peptide against soluble Aβ1-42, and cleavage sites.

The measurement of activity was performed in the same manner as in the above item (1), except that JAL 12-20 C19M was used as the hydrolytic peptide and purchased Aβ1-42 (Peptide Institute Inc.) was used as the substrate. As a result, Aβ1-42 was cleaved by JAL 12-20 C19M (FIG. 25).

Example 6

(1) Autodigestion of Box B

Figure 26:
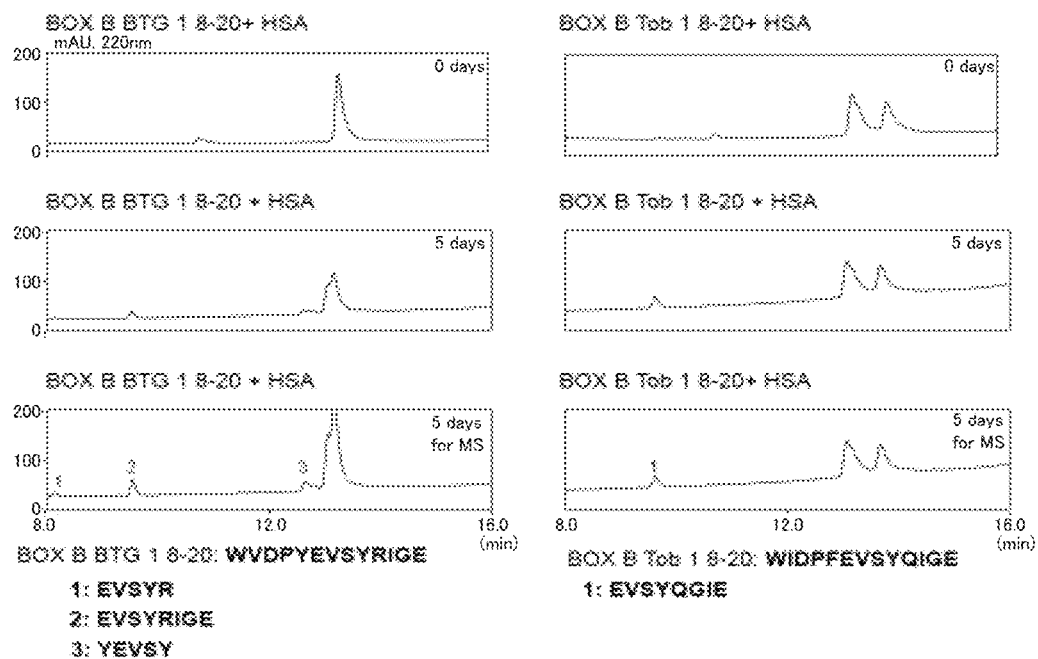
FIG. 26 shows chromatograms showing autodigestion of catalytic peptides and the amino acid sequences of fragments obtained by degradation.

Autodigestion in Box B was examined. The measurement of activity was performed in the same manner as in the item (1) in Example 1, except that Box B BTG1 8-20 or Box B Tob1 8-20 was used as the hydrolytic peptide, HSA was added, and the incubation time was set to 0 days or 5 days. As a result, fragments suggesting the occurrence of autodigestion were observed (FIG. 26).

(2) Autodigestion of Fragment Peptides Derived from Intermediate Region of Tob1

Figure 27:
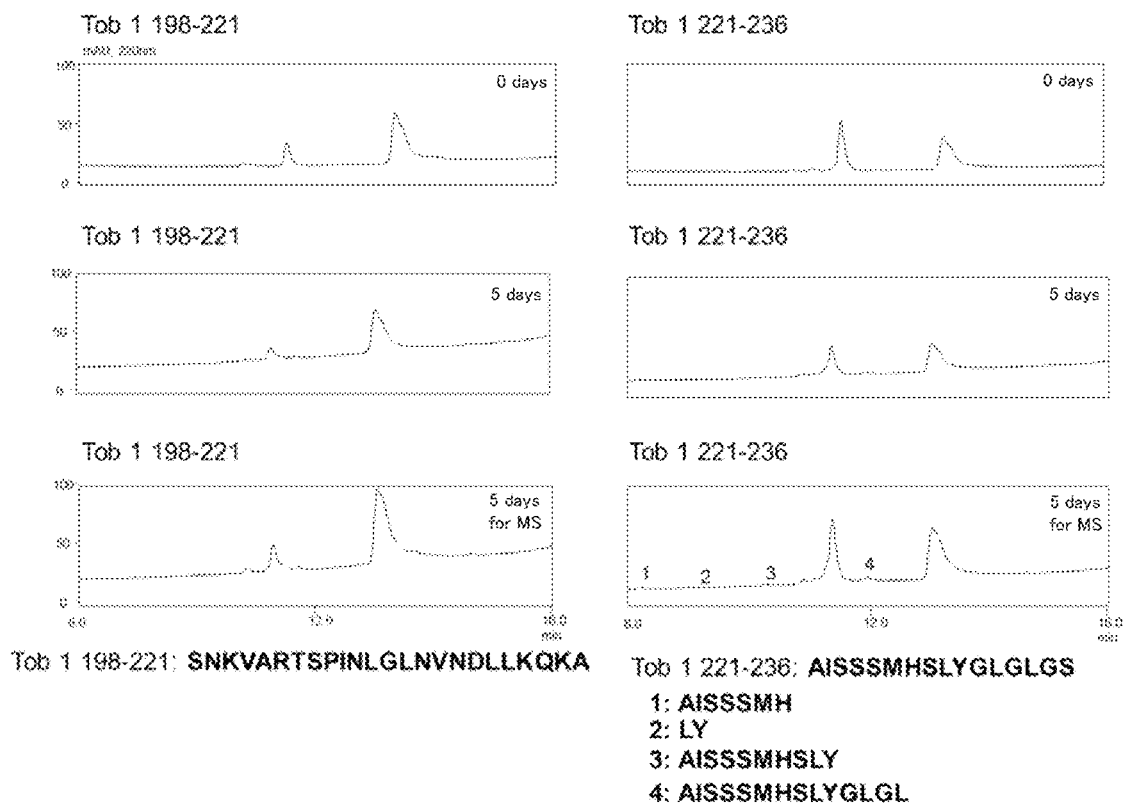
FIG. 27 shows chromatograms showing autodigestion of catalytic peptides and the amino acid sequences of fragments obtained by degradation.

The measurement of activity was performed in the same manner as in the above item (1), except that Tob1 198-221 or Tob1 221-236 was used as the hydrolytic peptide and the incubation time was set to 0 days and 5 days. As a result, fragments suggesting autodigestion of Tob1 221-236 were observed (FIG. 27).

(3) Examination of Activity Against Aβ

Figure 28:
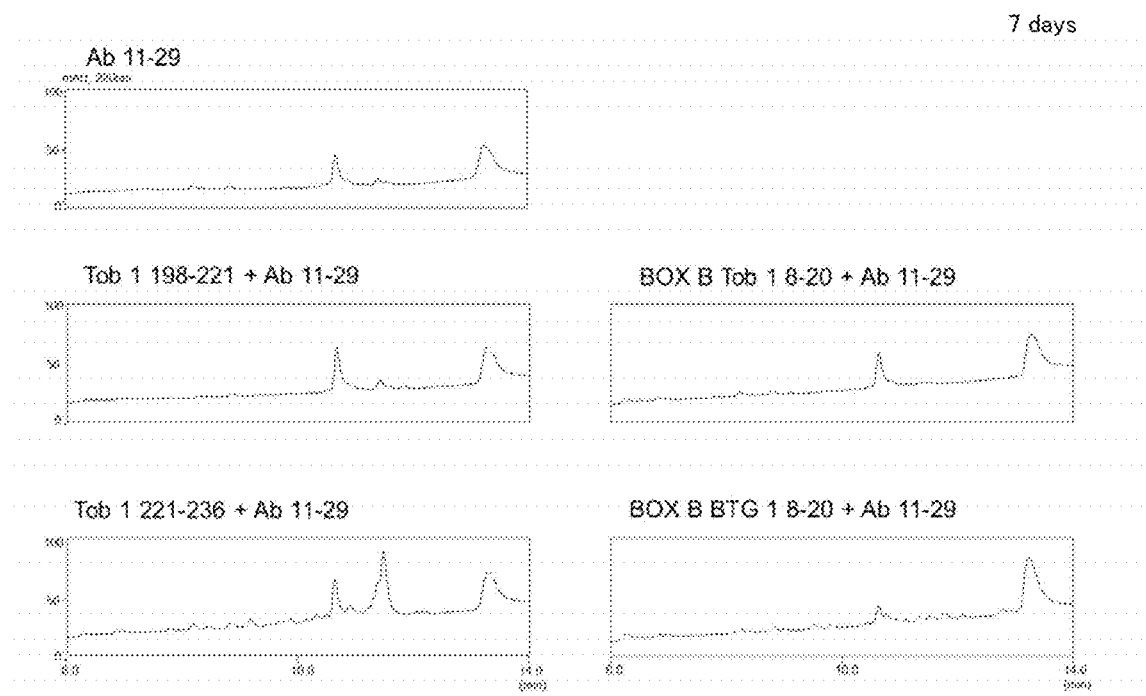
FIG. 28 shows chromatograms showing the hydrolysis activity of catalytic peptides against Aβ11-29.

The measurement of activity was performed in the same manner as in the above item (1), except that Tob1 198-221, Tob1 221-236, Box B Tob1 8-20, or Box B BTG1 8-20 was used as the hydrolytic peptide and Aβ11-29 was used as the substrate. As a result, Tob1 221-236 and Box B BTG1 8-20 exhibited activity (FIG. 28).

Example 7

Regarding a partial sequence JAL-TA9 of the above-described JAL mutant JAL 1-22 C19M, the present example examined various properties and also performed structural analysis.

```
JAL 1-22 C19M:
KYEGHWYPEKPYKGSGFRMIHI

JAL-TA9:
                                        (SEQ ID NO: 50)
PYKGSGFRMI
```

As substrates, Aβ42 in the form of soluble powder (authentic sample, Peptide Institute Inc.) and fragment peptides thereof, namely, Aβ1-20, Aβ11-29, and soluble Aβ28-42, were used. The measurement of activity was performed in the same manner as in the item (1) in Example 1, except that a reaction solution having the following reaction solution composition 1 was used, the reaction solution was incubated at 37° C. for a predetermined time, and 10 µl of the reaction solution then was applied to HPLC. In the case of MS analysis, the MS analysis was performed after applying 20 µl of the reaction solution to HPLC and collecting an aliquot of the peak.

Aβ1-42:
DAEFRHDSGYEVHHQKLVFFAEDVGSNKGAIIGLMVGGVVIA

Aβ1-20:
DAEFRHDSGYEVHHQKLVFF

Aβ11-29:
EVHHQKLVFFAEDVGSNKG

Aβ28-42:
KGAIIGLMVGGVVIA

TABLE 9

|  | Added amount | Final concentration |
|---|---|---|
| (Reaction Solution Composition 1) | | |
| 1 mmol/l JAL-TA9 | 20 µl | 0.2 mmol/l |
| 1 mmol/l substrate | 5 µl | 0.05 mmol/l |
| 10% DMSO | 0 µl or 5 µl | 0% or 0.5% |
| PBS | 10 µl | 0.05% |
| 0.05% HSA | 50 µl | |
| Ultrapure water | Balance | |
| Total | 100 µl | |
| (Reaction Solution Composition 2) | | |
| 5 mmol/l JAL-TA9 | 337 µl | 1 mmol/l |
| Substrate (solid) | 1.9 mg | 0.25 mmol/l |
| PBS | 168 µl | |
| 5% HSA | 42 µl | 0.125% |
| Ultrapure water | 1137 µl | |
| Total | 1684 µl | |

*DMSO was addded when Aβ1-20 and Aβ11-29 were used.

As a solid substrate, a crystal of Aβ42 was used. The measurement of activity was performed in the same manner as in the item (1) in Example 1, except that a reaction solution having the reaction solution composition 2 was used, the reaction solution was incubated at 37° C. for a predetermined time, and 10 µl of the reaction solution then was applied to HPLC. In the case of MS analysis, the MS analysis was performed after applying 100 µl of the reaction solution to HPLC and collecting an aliquot of the peak.

Figure 29:
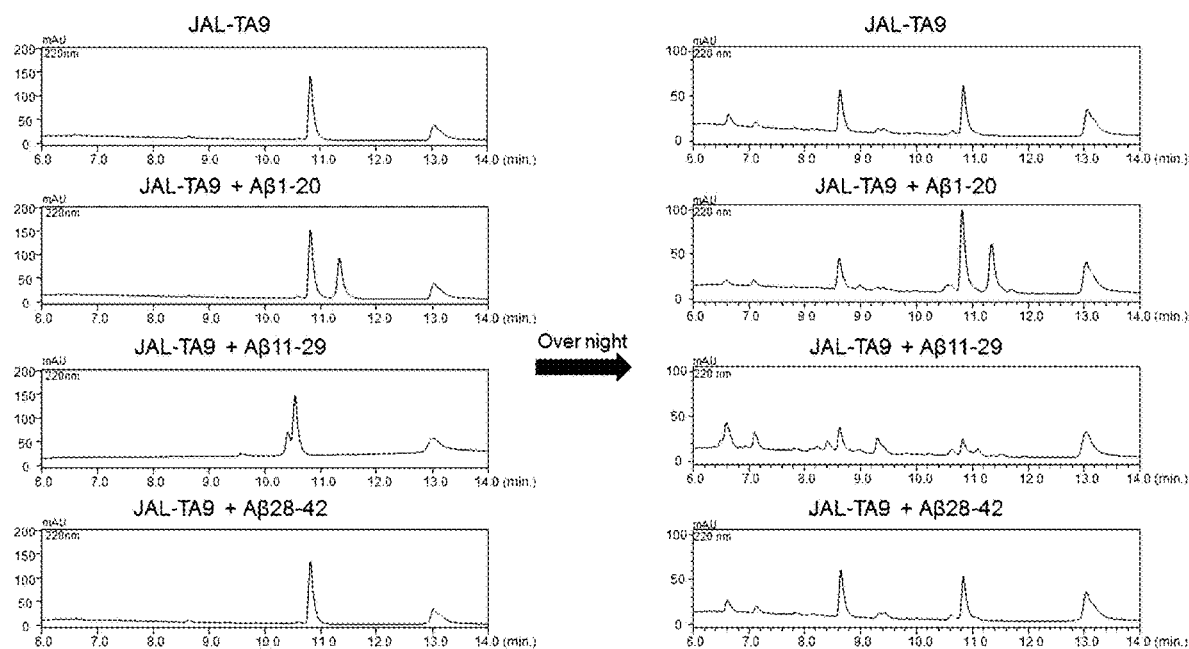
FIG. 29 shows chromatograms showing the hydrolysis activity of a catalytic peptide against Aβ.

(1) Aβ-Derived Fragments (Aβ-Fs)
(1-1) Activity of JAL-TA9 Against Aβ-Fs
The results obtained are shown in FIG. 29. FIG. 29 shows the results of the HPLC analysis of the reaction solution. The chromatograms on the left show the results obtained after the reaction for 0 hours, and the chromatograms on the right show the results obtained after allowing the reaction to proceed overnight. As can be seen in FIG. 29, JAL-TA9 degraded all the Aβ-Fs. This demonstrates that JAL-TA9 has activity against Aβ-Fs.

Figure 30:
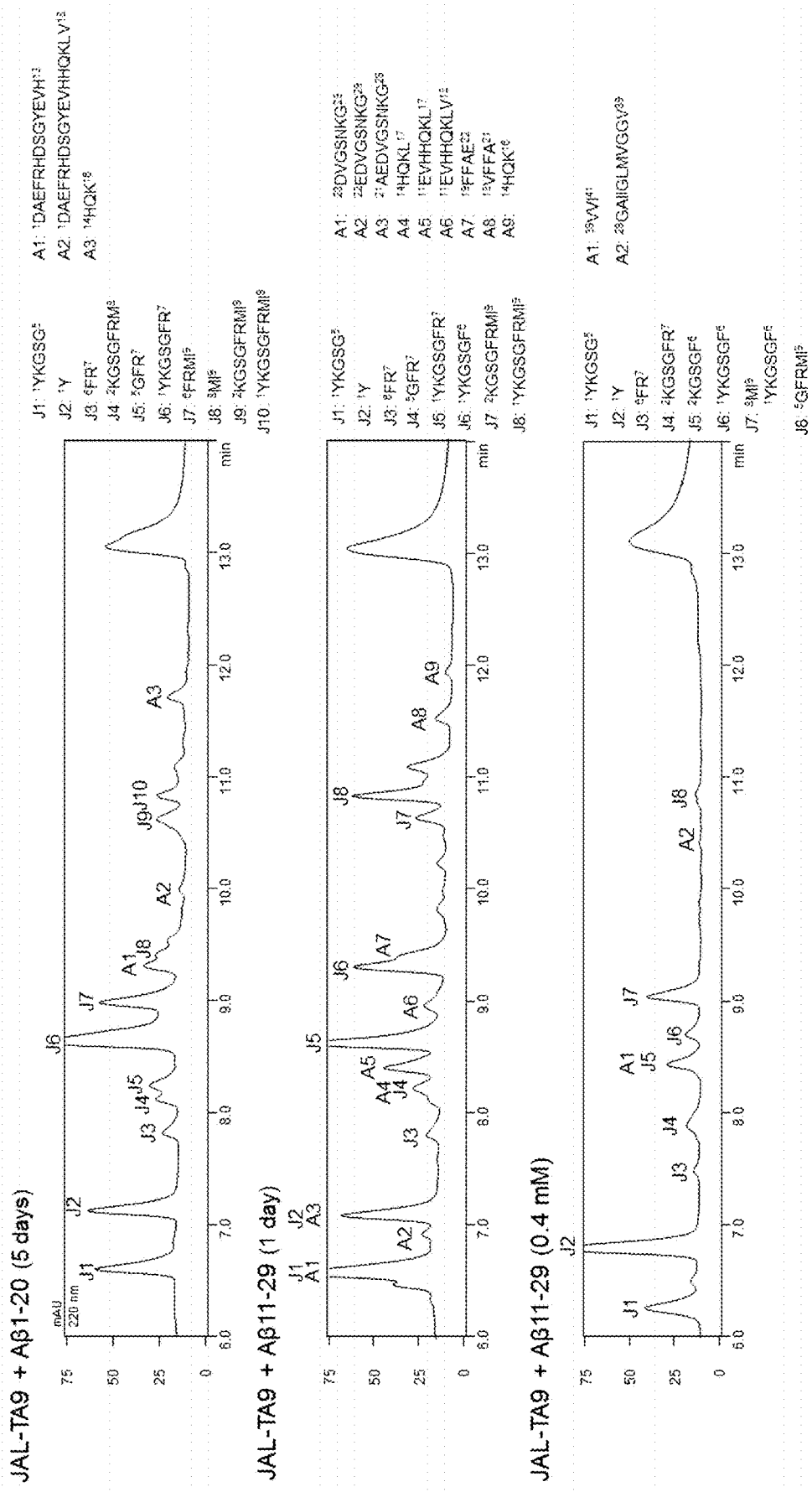
FIG. 30 shows chromatograms showing hydrolysis activity of the catalytic peptide against Aβ.

(1-2) Identification of Cleavage Sites in Aβ-Fs
The results obtained are shown in FIG. 30. FIG. 30 shows the results of fragment identification by MS after allowing the reaction to proceed for a predetermined time, and shows the sequences of fragments obtained by degradation. In FIG. 30, "J" indicates a fragment derived from JAL-TA9, and "A" indicates a fragment derived from an Aβ-F. As can be seen in FIG. 30, all the Aβ-Fs were cleaved at a plurality of sites. In particular, strong cleavage activity was exhibited against an intermediate region of Aβ that had been reported as being an aggregation nucleus.

Figure 31:
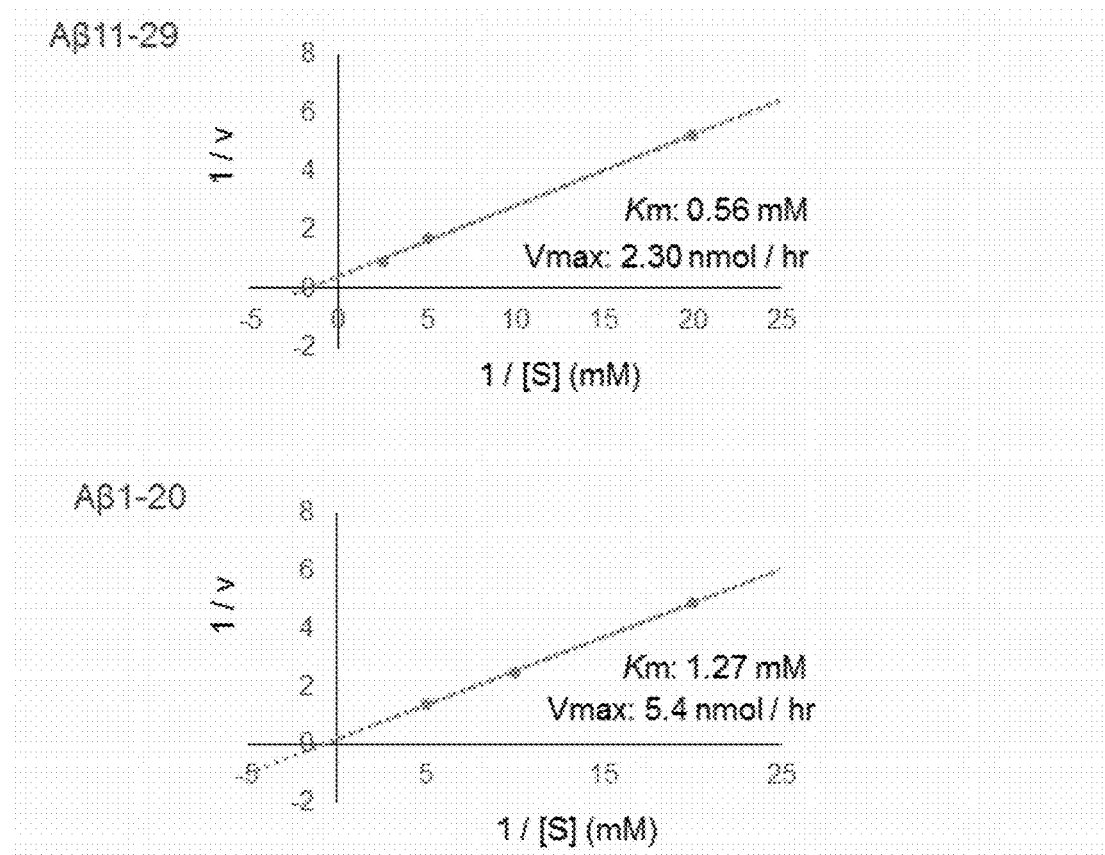
FIG. 31 shows graphs showing the relationship between the substrate concentration and the reaction rate.

(2) Reaction Rates for Aβ1-20 and Aβ11-29
HPLC was performed with the Aβ-F concentration in a reaction solution being set to 0.05, 0.2, or 0.4 mmol/l and a reaction time being set to 0 hours or 1 hour. Then, on the basis of the reduction rate of the peak of each Aβ-F, the Km value was determined. The results obtained are shown in FIG. 31. FIG. 31 shows graphs showing the relationship between the substrate concentration and the reaction rate. As a result, it was found that Aβ11-29 has higher affinity to JAL-TA9 than Aβ1-20.

Figure 32:
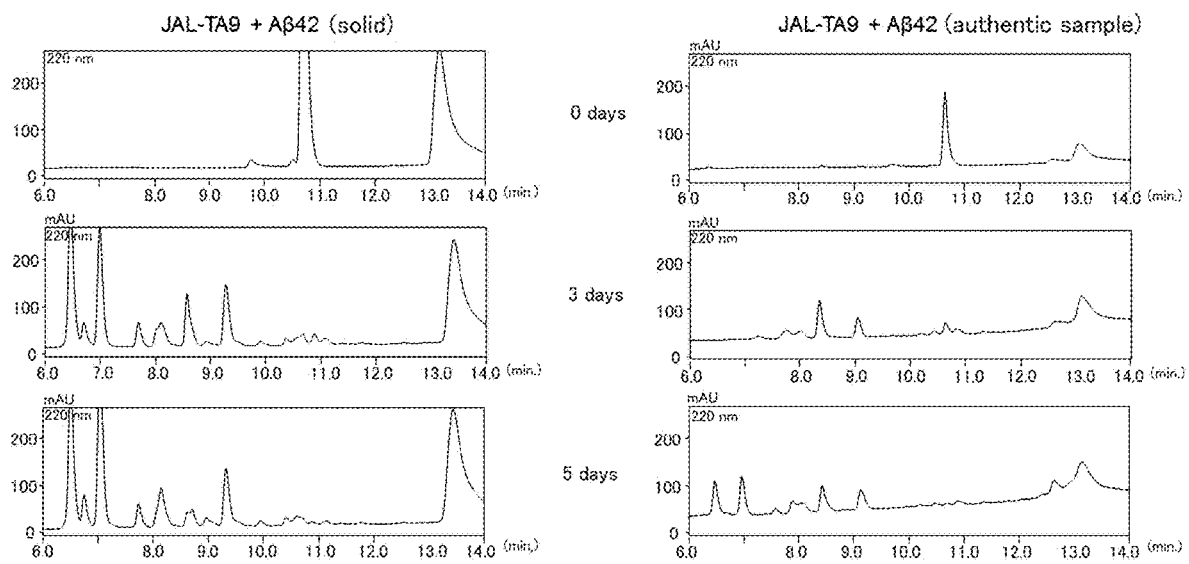
FIG. 32 shows chromatograms showing the hydrolysis activity of the catalytic peptide against Aβ.

(3) Aβ42
(3-1) Activity of JAL-TA9 Against Aβ42
As Aβ42, the above-described authentic sample and solid were used. The results obtained are shown in FIG. 32. FIG. 32 shows the results of HPLC analysis of the reaction solution. The chromatograms on the left show the results obtained when the solid Aβ42 was used, and the chromatograms on the right show the results obtained when the authentic sample Aβ42 was used. As can be seen in FIG. 32, JAL-TA9 degraded both types of Aβ42. This demonstrates that JAL-TA9 has activity against them.

Figure 35:
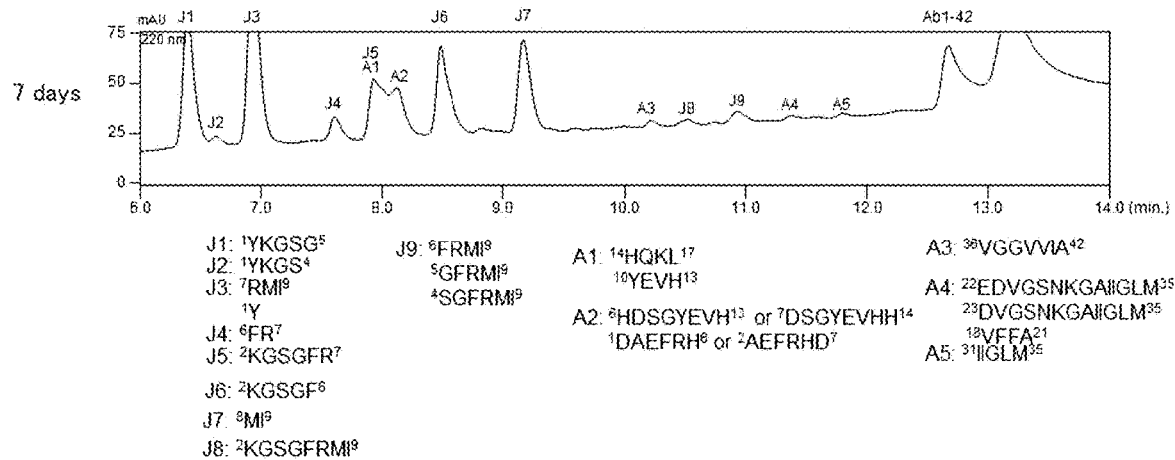
FIG. 35 shows a chromatogram showing the hydrolysis activity of the catalytic peptide against Aβ.
Figure 36:
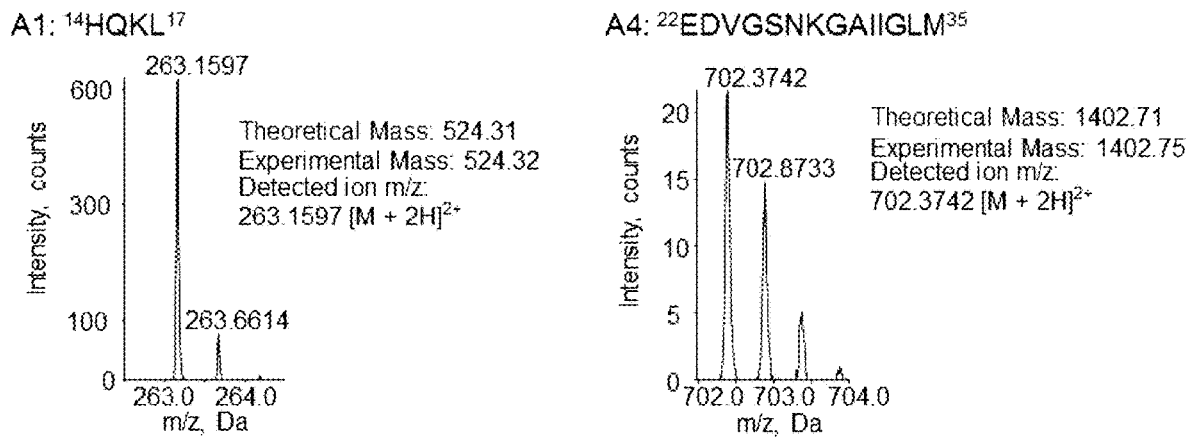
FIG. 36 shows chromatograms showing the hydrolysis activity of the catalytic peptide against Aβ.

(3-2) Identification of Cleavage Sites in Aβ42
The results obtained are shown in FIGS. 33 to 36. FIGS. 33 and 34 show the results obtained regarding the solid Aβ42, and FIGS. 35 and 36 show the results obtained regarding the soluble authentic sample Aβ42. In FIGS. 33 to 36, "J" indicates a fragment derived from JAL-TA9, and "A" indicates a fragment derived from Aβ42. FIG. 33 shows the results of fragment identification of the solid Aβ42 by MS after allowing the reaction to proceed for a predetermined time, and FIG. 34 shows the results of identification of fragments A5, A7, A8 by MS. FIG. 35 shows the results of fragment identification of the soluble authentic sample Aβ42 by MS after allowing the reaction to proceed for a predetermined time, and FIG. 36 shows the results of identification of fragments A1 and A4 by MS.

When the soluble authentic sample Aβ42 was used, a novel peak appears after the reaction for 3 days, and as can be seen in FIGS. 35 and 36, the soluble authentic sample Aβ42 was cleaved at a plurality of sites after the reaction for 7 days. The examination on the cleavage sites revealed that, in particular, regarding Aβ, strong cleavage activity was exhibited against an intermediate region of Aβ that had been reported as being an aggregation nucleus. Likewise, as can be seen in FIGS. 33 and 34, activity against the solid Aβ42 also was observed.

Figure 37:
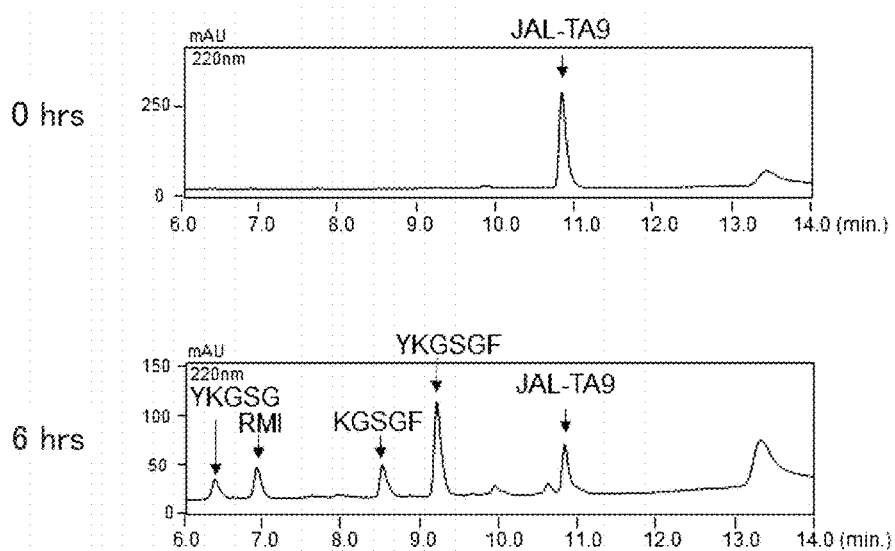
FIG. 37 shows chromatograms showing autodigestion of the catalytic peptide.

(4) Autodigestion of JAL-TA9
(4-1) Examination of Autodigestion
JAL-TA9 was reacted in the same manner except that a substrate was not added to examine the autodigestion of JAL-TA9. The results obtained are shown in FIG. 37. As can be seen in FIG. 37, autodigestion of JAL-TA9 was observed.

Figure 38:
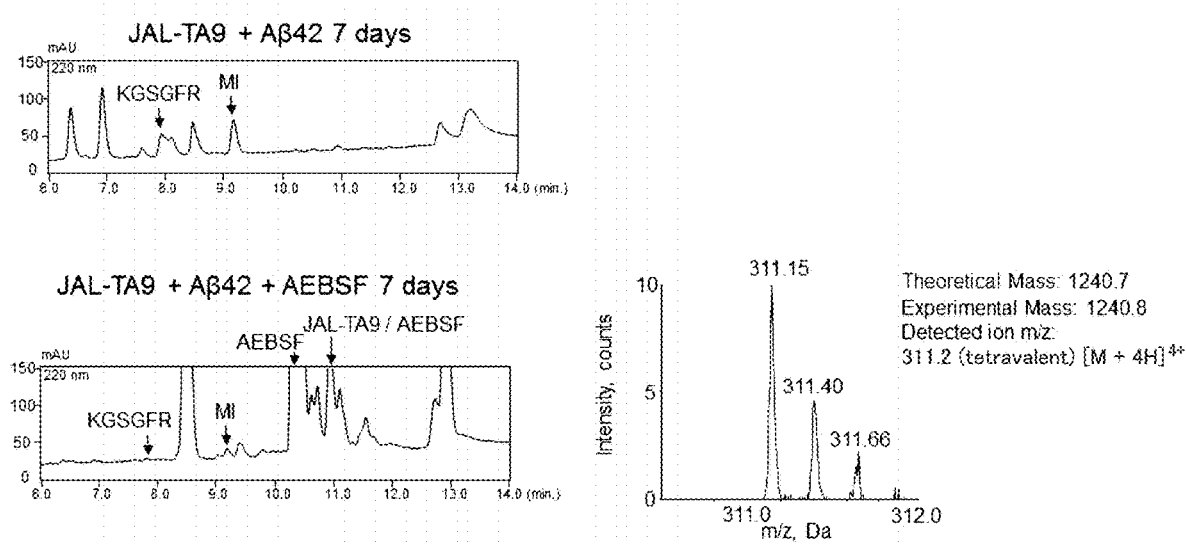
FIG. 38 shows chromatograms showing inhibition of autodigestion of the catalytic peptide by a protease inhibitor.

(4-2) Influence of Inhibitor on Autodigestion
The influence of an inhibitor on autodigestion of JAL-TA9 was examined. The measurement of activity was performed in the same manner, except that a protease inhibitor was added to the reaction solution at a final concentration of 0 mmol/l or 6 mmol/l. As the protease inhibitor, the serine protease inhibitor AEBSF, which inhibited the autodigestion of JAL 12-22 C19M in the item (6) in Example 4, was used. The results obtained are shown in FIG. 38. In FIG. 38, the graph on the right shows the result of MS analysis of the reaction solution containing the serine protease. As can be seen in FIG. 38, autodigestion was inhibited by adding AEBSF. From this result, it is considered that JAL-TA9 is a serine protease-like peptide.

Figure 39:
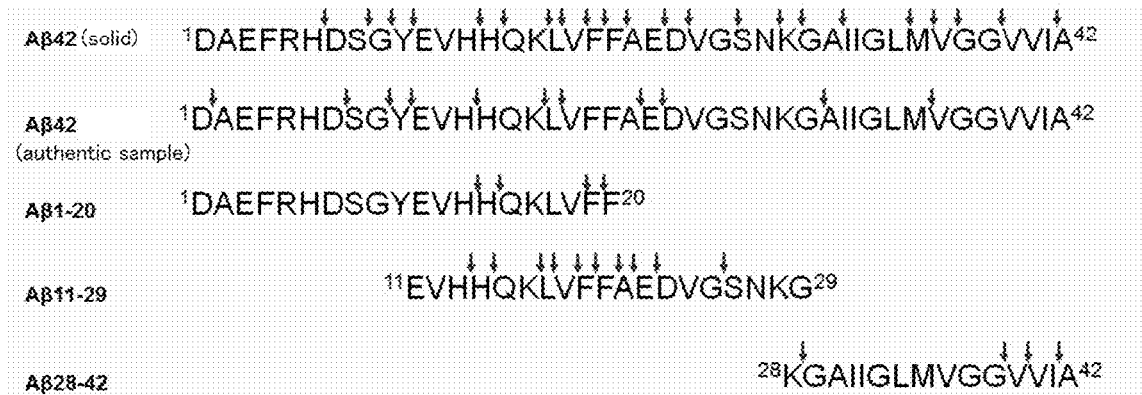
FIG. 39 shows cleavage sites in Aβ by the catalytic peptide.

On the basis of the results obtained in the above items (1) to (4), cleavage sites in Aβ42 and fragments derived from Aβ are shown in FIG. 39. As can be seen in FIG. 39, it was found that strong cleavage activity was exhibited against an intermediate region of Aβ42.

(5) Intermolecular Interaction of JAL-TA9 with Aβ42 and Aβ-F

Figure 40:
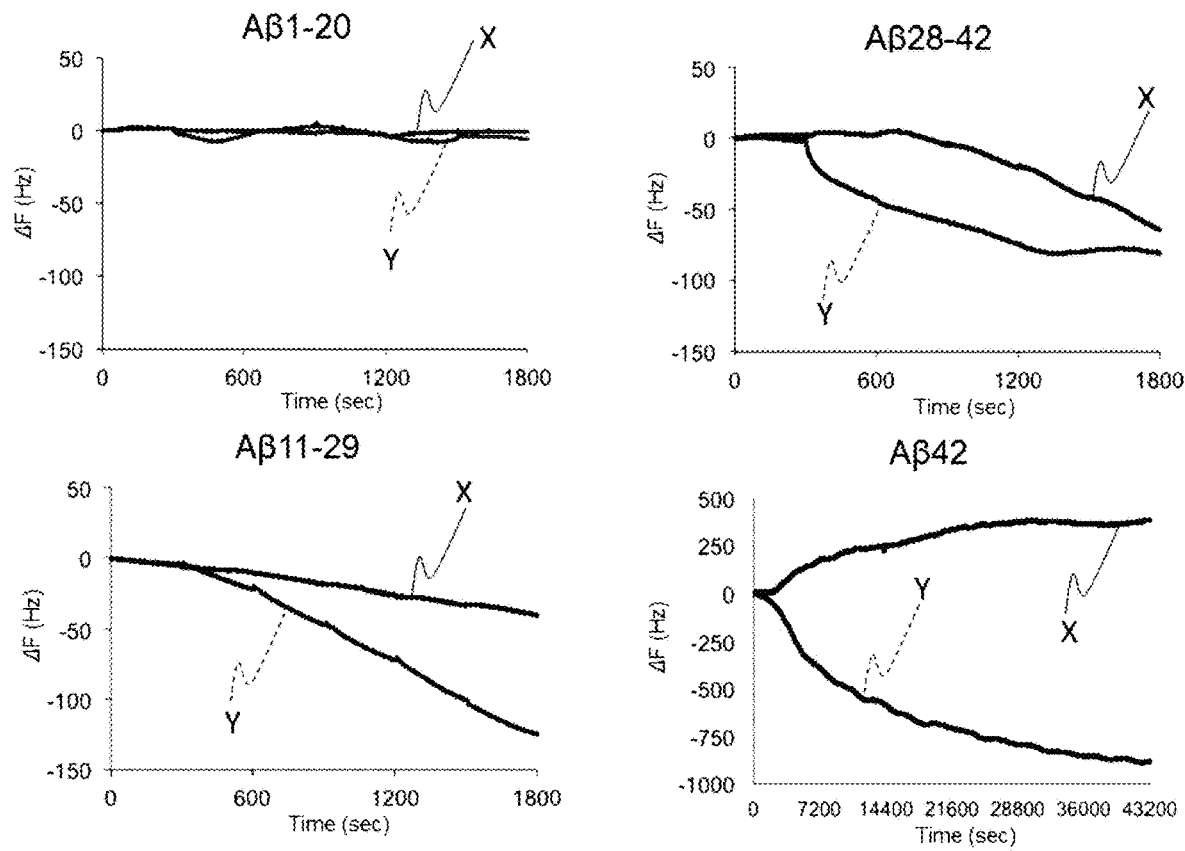
FIG. 40 shows graphs showing intermolecular interactions of the catalytic peptide with Aβ.

Intermolecular interactions of JAL-TA9 with Aβ42 and with Aβ-F were examined using an AFFINX QNµ (trade name, INITIUM, Inc.) in accordance with its protocol. The results obtained are shown in the graphs of FIG. 40. In FIG. 40, X indicates the result obtained when JAL-TA9 was not immobilized on a platinum electrode, and Y indicates the result obtained when JAL-TA9 was immobilized on the platinum electrode. As can be seen in FIG. 40, JAL-TA9 caused a strong interaction with each of Aβ11-29 and Aβ42, and there was a correlation between the interaction and the cleavage activity.

(6) Structural Analysis of JAL-TA9

Figure 41:
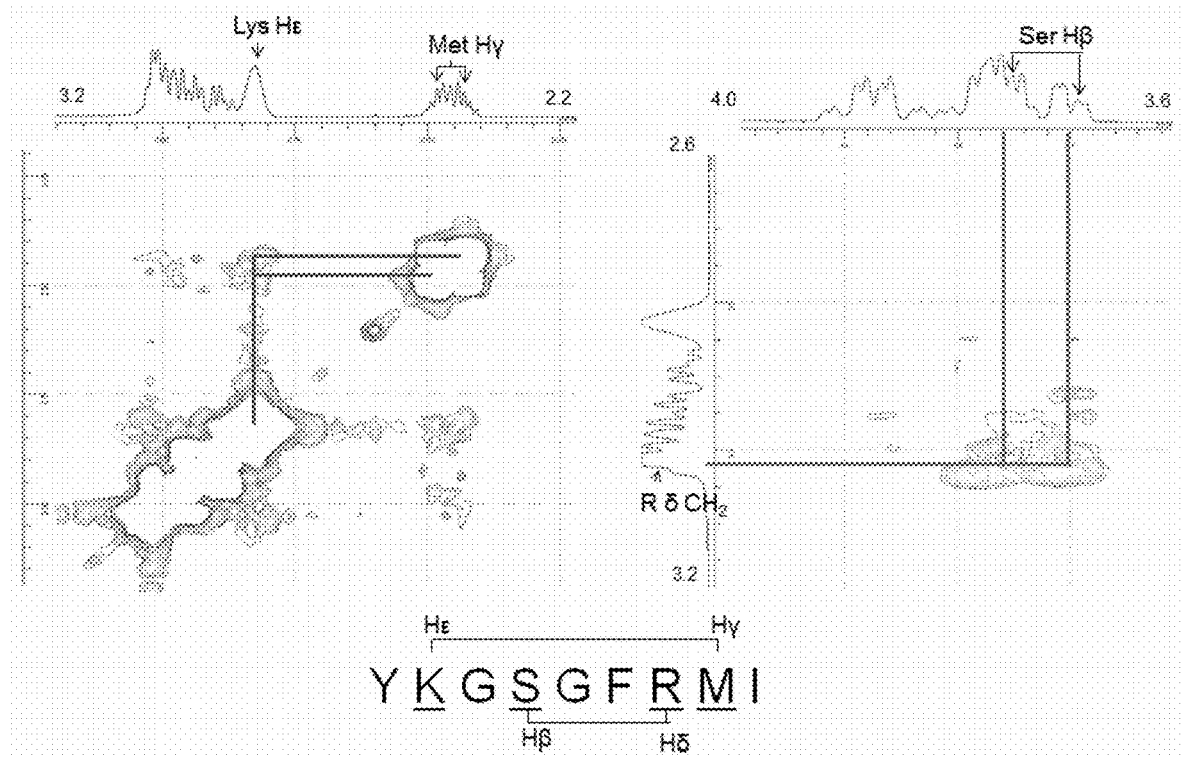
FIG. 41 shows the results of NMR analysis of the catalytic peptide.
Figure 42:
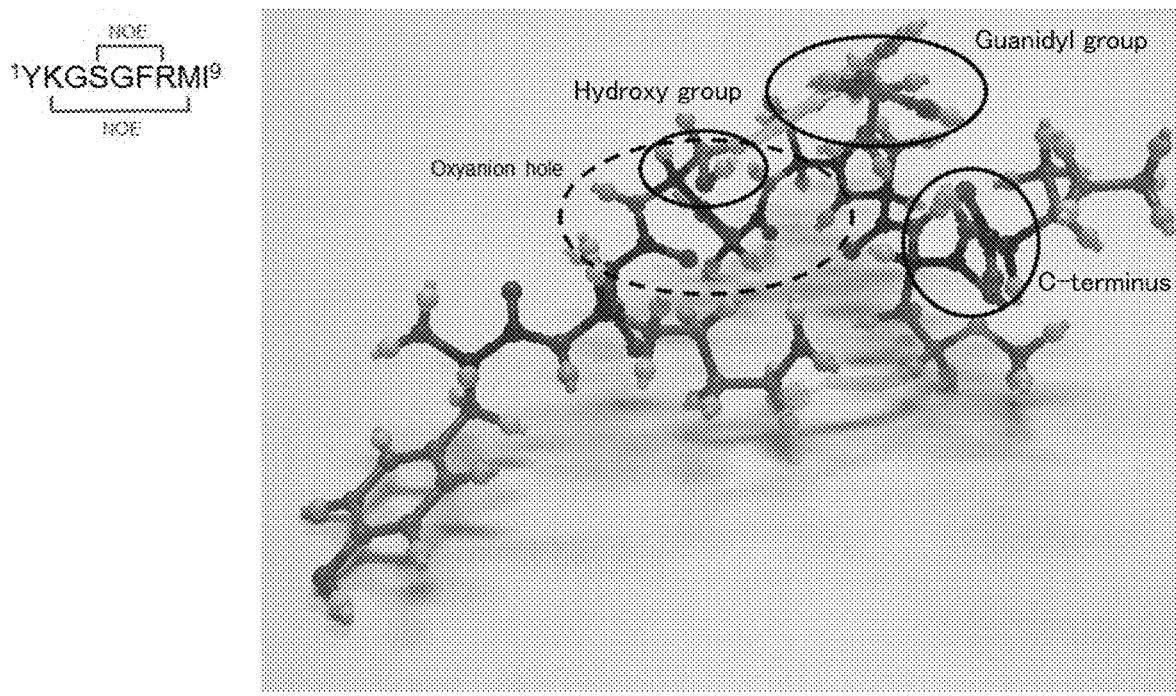
FIG. 42 is a schematic view showing the putative structure of the catalytic peptide.

JAL-TA9 was subjected to NMR. The result obtained is shown in FIG. 41. Also, the three-dimensional structure and active sites of JAL-TA9 are shown in FIG. 42. It is speculated that JAL-TA9 has a very compact serine protease-like three-dimensional structure with Lys Hε and Met Hγ, and also, Ser Hβ and Arg Hδ being at positions spatially close to each other. It is also speculated that, in JAL-TA9, two amino groups (Gly) form an oxyanion hole with a hydroxy group (Ser) at the center, and a basic amino acid, a hydroxy group, and a C-terminal carbonyl group, which are necessary for the serine protease-like activity, are present at positions sterically close to each other. It is considered that JAL-TA9 having such a low molecular weight enters into an oligomer of Aβ, and degrades Aβ from the inside owing to its hydrolysis activity. It is to be noted, however, that the present invention is not limited by this speculation.

Example 8

The present example examined whether JAL-TA9 degrades a Tau protein, which is one of causative substances of Alzheimer's disease.

(1) Activity

As a substrate, a Tau microtubule binding domain (MBD)-derived fragment (Tau MBD1-30) was used. The measurement of activity was performed in the same manner as in the item (1) in Example 1, except that a reaction solution having the following reaction solution composition 3 was used, the reaction solution was incubated at 37° C. for a predetermined time, and 10 µl of the reaction solution then was applied to HPLC. In the case of MS analysis, the MS analysis was performed after applying 20 µl of the reaction solution to HPLC and collecting an aliquot of the peak.

```
Tau MBD 1-30:
                                         (SEQ ID NO: 51)
GSKDNIKHVPGGGSVQIVYKPVDLSKVTSK
```

TABLE 10

(Reaction Solution Composition 3)

| | Added amount | Final concentration |
|---|---|---|
| 1 mmol/l JAL-TA9 | 20 µl | 0.2 mmol/l |
| 1 mmol/l substrate (10% DMSO) | 5 µl | 0.05 mmol/l |

TABLE 10-continued (Reaction Solution Composition 3)

| | Added amount | Final concentration |
|---|---|---|
| PBS | 10 µl | |
| 0.05% HSA | 5 µl | |
| Ultrapure water | 60 µl | |
| Total | 100 µl | |

Figure 43:
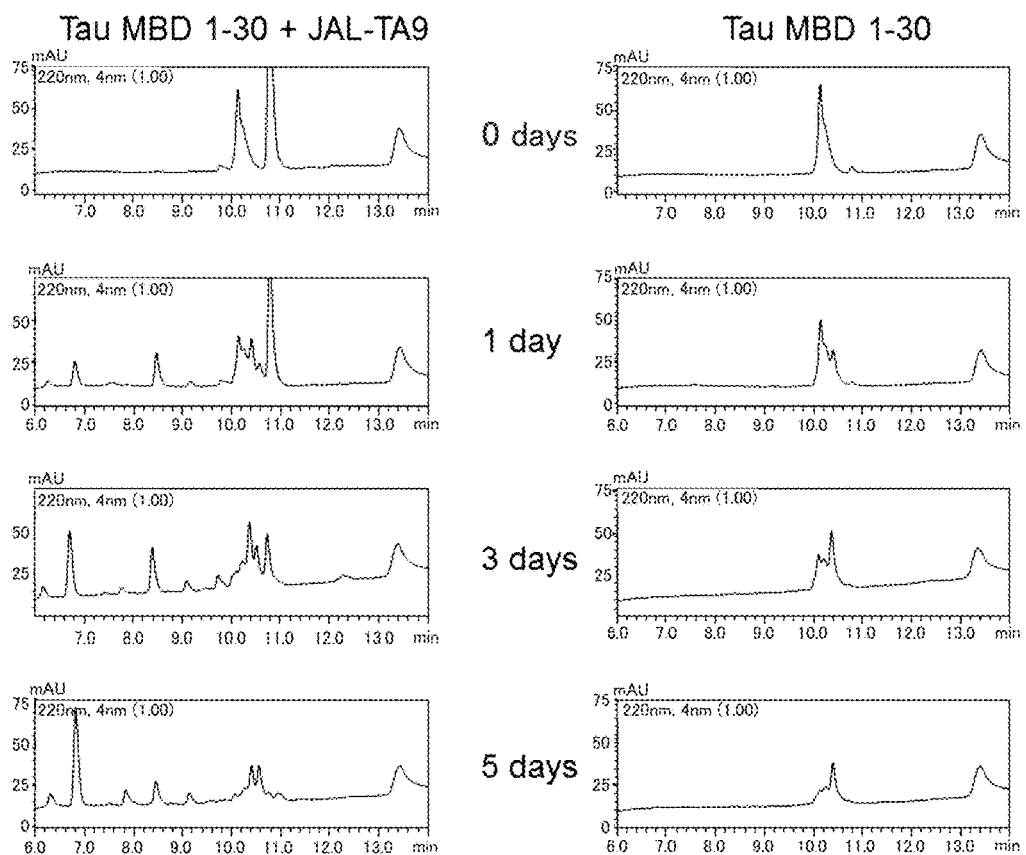
FIG. 43 shows chromatograms showing the hydrolysis activity of the catalytic peptide against Tau.

The results obtained are shown in FIG. 43. FIG. 43 shows the results of the HPLC analysis of the reaction solution. The chromatograms on the left show the results obtained after the reaction for 0 hours, and the chromatograms on the right show the results obtained after allowing the reaction to proceed overnight. As can be seen in FIG. 43, JAL-TA9 degraded Tau MBD 1-30. This demonstrates that JAL-TA9 has activity against Tau MBD 1-30.

(2) Identification of Cleavage Sites

Figure 45:
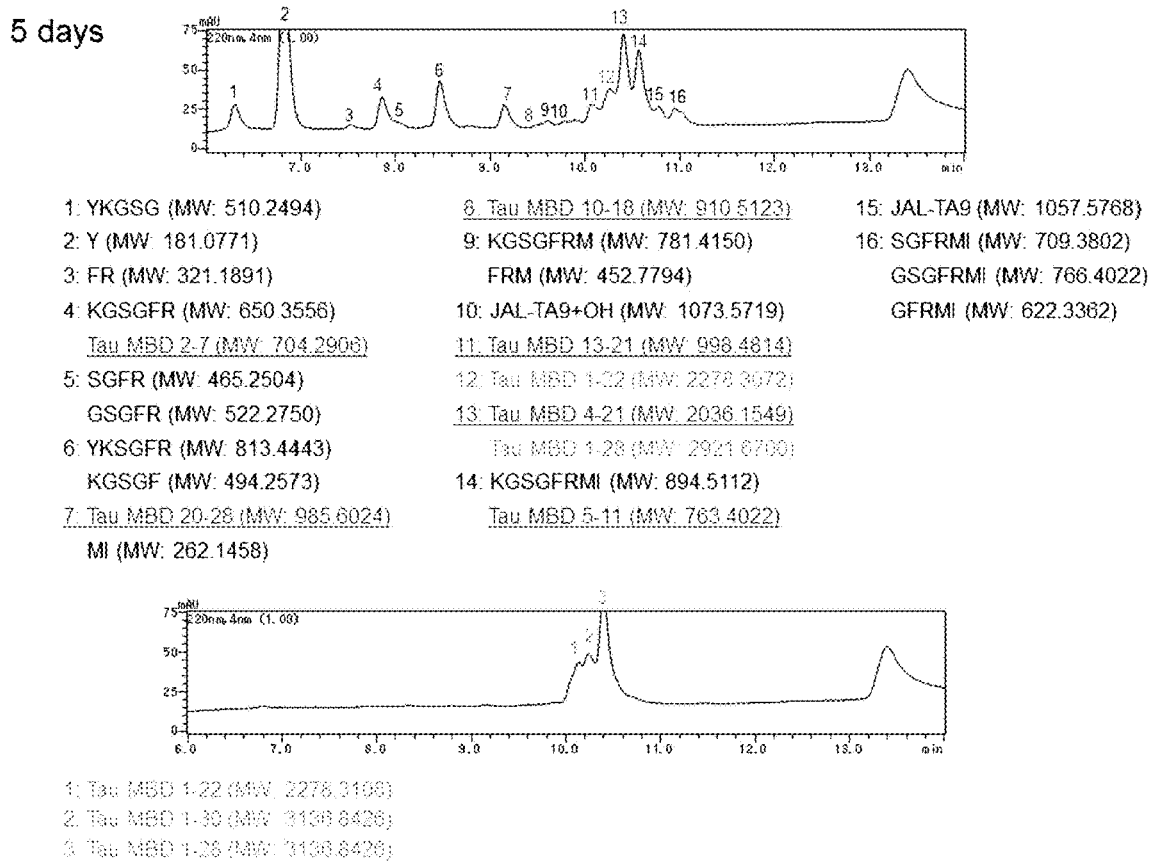
FIG. 45 shows chromatograms showing the hydrolysis activity of the catalytic peptide against Tau.

FIGS. 44 and 45 show the results of fragment identification by MS obtained after the reaction for 1 day and 5 days, and the sequences of fragments obtained by degradation. In each of FIGS. 44 and 45, the upper chromatogram shows the result obtained when JAL-TA9 was reacted with Tau MBD 1-30, and the lower chromatogram shows the result obtained when the reaction solution did not contain JAL-TA9.

As can be seen in the lower chromatogram in FIG. 44 (after the reaction for 1 day), the degradation of Tau MBD 1-30 was observed when JAL-TA9 was not added. As can be seen in the upper chromatogram in FIG. 44, by reacting JAL-TA9 with Tau MBD 1-30, not only the same fragments as those shown in the lower chromatogram, namely, degradation fragments of Tau MBD 1-30 (9, 11) and autodigestion fragments of JAL-TA9 (1 to 5, 7, 8, 12, 13), but also fragments of Tau MBD 1-30 resulting from the cleavage by JAL-TA9 (6 and 10 underlined in FIG. 44) were obtained. Further, as can be seen in FIG. 45 (after the reaction for 5 days), by reacting JAL-TA9 with Tau MBD 1-30, not only the same fragments as those shown in the lower chromatogram, namely, degradation fragments of Tau MBD 1-30 (12, 13) and autodigestion fragments of JAL-TA9 (1 to 6, 9, 10, 14 to 16), but also fragments of Tau MBD 1-30 resulting from the cleavage by JAL-TA9 (4, 7, 8, 11, 13, and 14 underlined in FIG. 45) were obtained.

Figure 46:
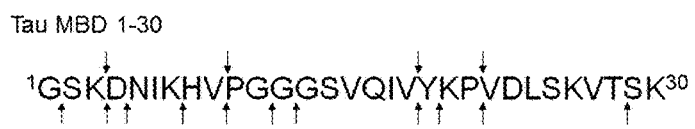
FIG. 46 shows cleavage sites in Tau by the catalytic peptide.

On the basis of these results, cleavage sites in Tau MBD 1-30 are shown in FIG. 46.

Example 9

A chimera peptide of JAL-TA9 was synthesized, and the activity of the chimera peptide against Aβ was examined.

(1) Aβ11-29

A chimera peptide was synthesized by binding an a-AC peptide as an Aβ binding site to the N-terminus of JAL-TA9. As a substrate, Aβ11-29, which is a fragment peptide of Aβ42, was used. The measurement of activity was performed in the same manner as in the item (1) in Example 1, except that a reaction solution having the following reaction solution composition was used, the reaction solution was incubated at 37° C. for a predetermined time, and 10 µl of the reaction solution then was applied to HPLC. In the case of MS analysis, the MS analysis was performed after applying 20 µl of the reaction solution after the reaction for 6 days to HPLC and collecting an aliquot of the peak.

```
Chimera peptide (Aβ binding site AAJAL-TA9)
                                          (SEQ ID NO: 52)
FVIFLDVKHFSPEDLTVK-AA-YKGSGFRMI
```

TABLE 11

(Reaction Solution Composition)

| | Added amount | Final concentration |
|---|---|---|
| 1 mmol/l chimera peptide (10% DMSO) | 20 µl | 0.2 mmol/l |
| 1 mmol/l substrate | 10 µl | 0.05 mmol/l |
| PBS | 10 µl | |
| 0.05% HSA | 50 µl | |
| Ultrapure water | 10 µl | |
| Total | 100 µl | |

Figure 47:
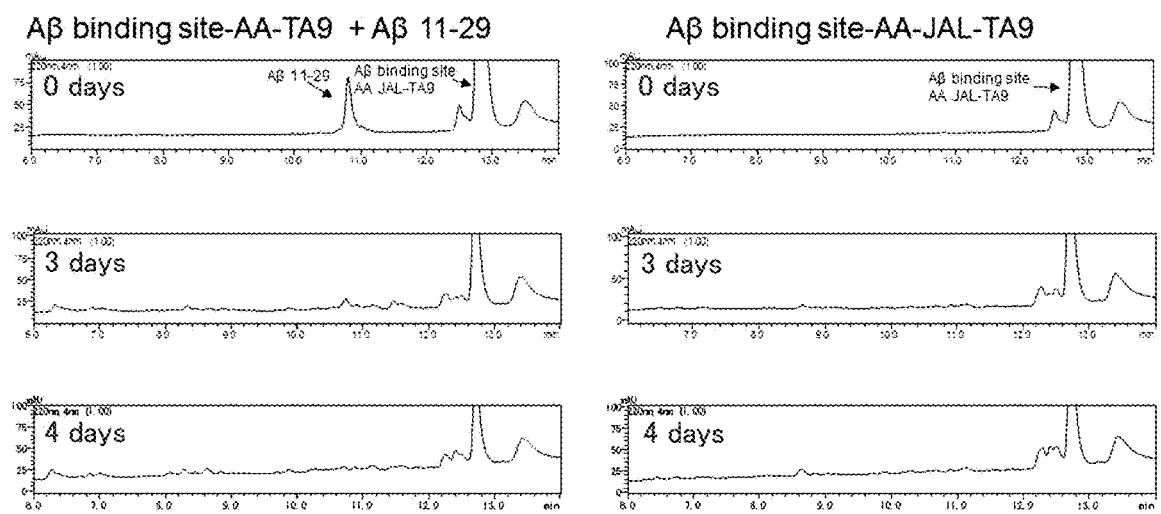
FIG. 47 shows chromatograms showing the hydrolysis activity of a catalytic peptide against Aβ.

The results obtained are shown in FIG. 47. FIG. 47 shows the results of the HPLC analysis of the reaction solution. The chromatograms on the left show the results obtained in the case where the substrate was added, and the chromatograms on the right show the results obtained in the case where the substrate was not added. As can be seen in FIG. 47, the chimera peptide degraded Aβ11-29. This demonstrates that the chimera peptide has activity.

Figure 48:
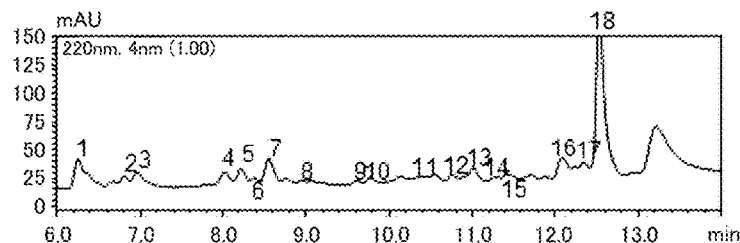
FIG. 48 shows a chromatogram showing the hydrolysis activity of the catalytic peptide against Aβ.

FIG. 48 shows the results of fragment identification by MS after the reaction for 6 days, and shows the sequences of fragments obtained by degradation.

(2) Aβ42

Aβ42 was used as a substrate. The measurement of activity was performed in the same manner as in the item (1) in Example 1, except that a reaction solution having the following reaction solution composition was used, the reaction solution was incubated at 37° C. for a predetermined time, and 10 µl of the reaction solution then was applied to HPLC. In the case of MS analysis, the MS analysis was performed after applying 20 µl of the reaction solution after the reaction for 7 days to HPLC and collecting an aliquot of the peak.

TABLE 12

(Reaction Solution Composition)

| | Added amount | Final concentration |
|---|---|---|
| 1 mmol/l chimera peptide (2.5% DMSO) | 20 µl | 0.2 mmol/l |
| 5 mmol/l substrate (50% DMSO) | 1 µl | 0.05 mmol/l |
| PBS | 10 µl | |
| 0.05% HSA | 50 µl | |
| Ultrapure water | 10 µl | |
| Total | 100 µl | |

Figure 49:
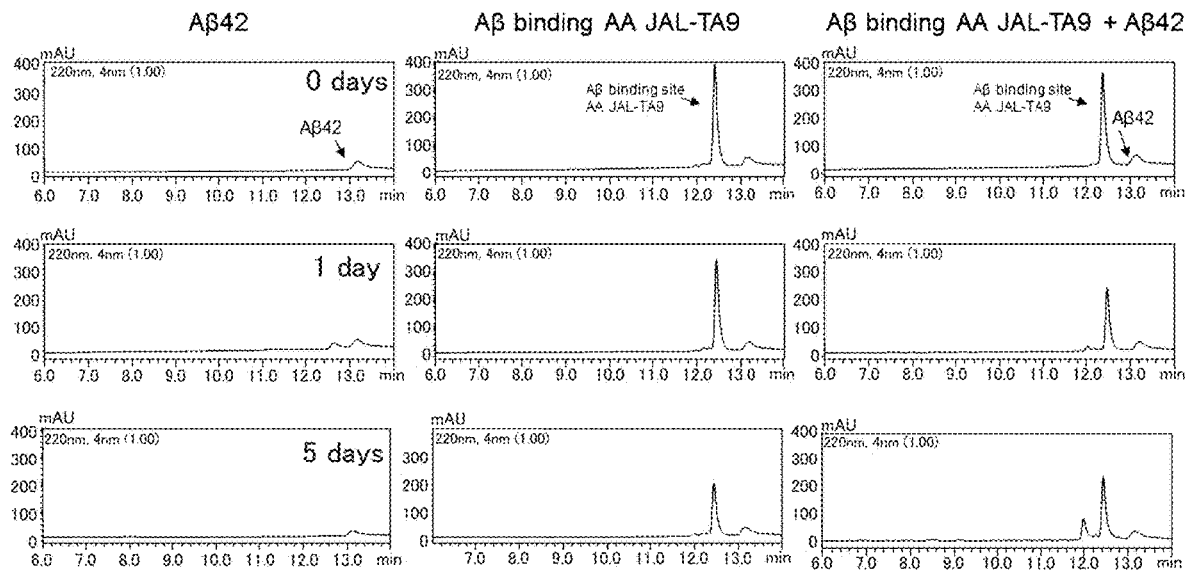
FIG. 49 shows chromatograms showing the hydrolysis activity of the catalytic peptide against Aβ.

The results obtained are shown in FIG. 49. FIG. 49 shows the results of the HPLC analysis of the reaction solution. The chromatograms on the left show the results obtained when the substrate was used alone, the chromatograms in the middle show the results obtained when the chimera peptide was used alone, and the chromatograms on the right show the results obtained when the substrate was reacted with the chimera peptide. As can be seen in FIG. 49, the chimera peptide degraded Aβ4211-29 from Day 1 after the start of the reaction. This demonstrates that the chimera peptide has activity.

FIGS. 50 and 51 show the results of fragment identification by MS after the reaction for 7 days, and show the sequences of fragments obtained by degradation. In FIG. 50, underlined sequences are fragments of Aβ42 resulting from the cleavage by the chimera peptide. FIG. 50 also shows cleavage sites in Aβ42 by the chimera peptide.

Example 10

The present example examined the hydrolysis activity of ANA-TA9, which is a mutant of a partial sequence of BTG3 (SEQ ID NO: 47:HWYPEKPSKGQAYRCIRV) in Box A. Hereinafter, the above-described BTG3 also is referred to as BTG/ANA. The compositions of reaction solutions used in the present example are shown in FIG. 52.

```
ANA-TA9:
                                          (SEQ ID NO: 53)
SKGQAYRMI
```

(1) Autodigestion

Figures 52, 53:
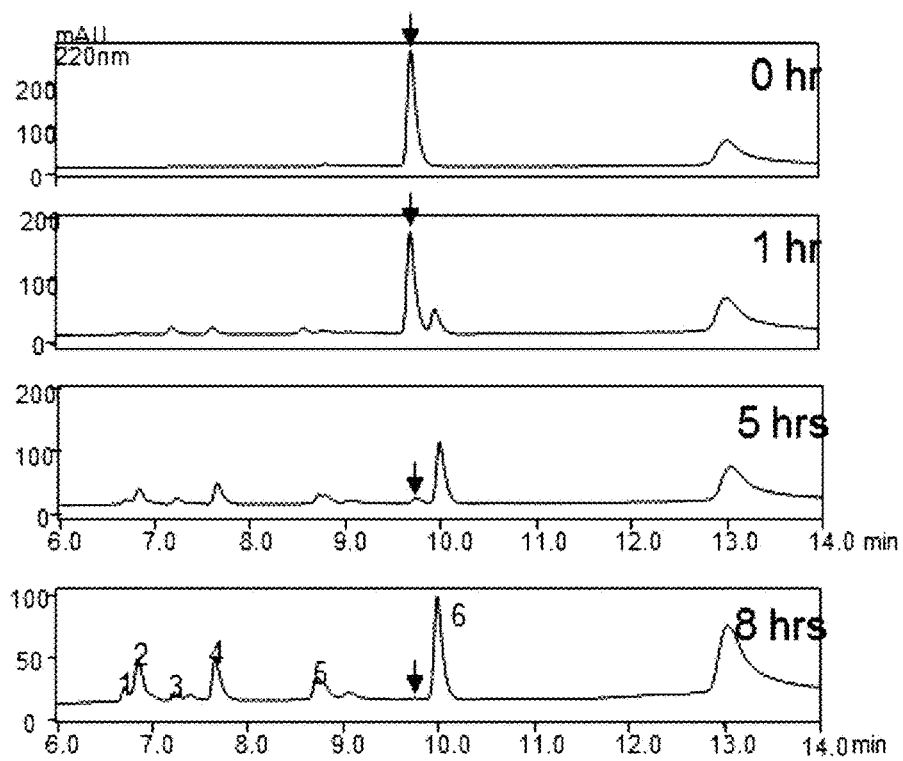
FIG. 52 shows the compositions of reaction solutions.
FIG. 53 shows chromatograms showing autodigestion of a catalytic peptide.

A reaction solution I shown in FIG. 52 was incubated at 37° C. for a predetermined time, and autodigestion of ANA-TA9 was examined by HPLC. The results obtained are shown in FIG. 53. As can be seen in FIG. 53, autodigestion of ANA-TA9 was observed. FIG. 53 also shows the sequences of fragments detected after the autodigestion.

(2) Cleavage of Aβ-Fs

Figure 54:
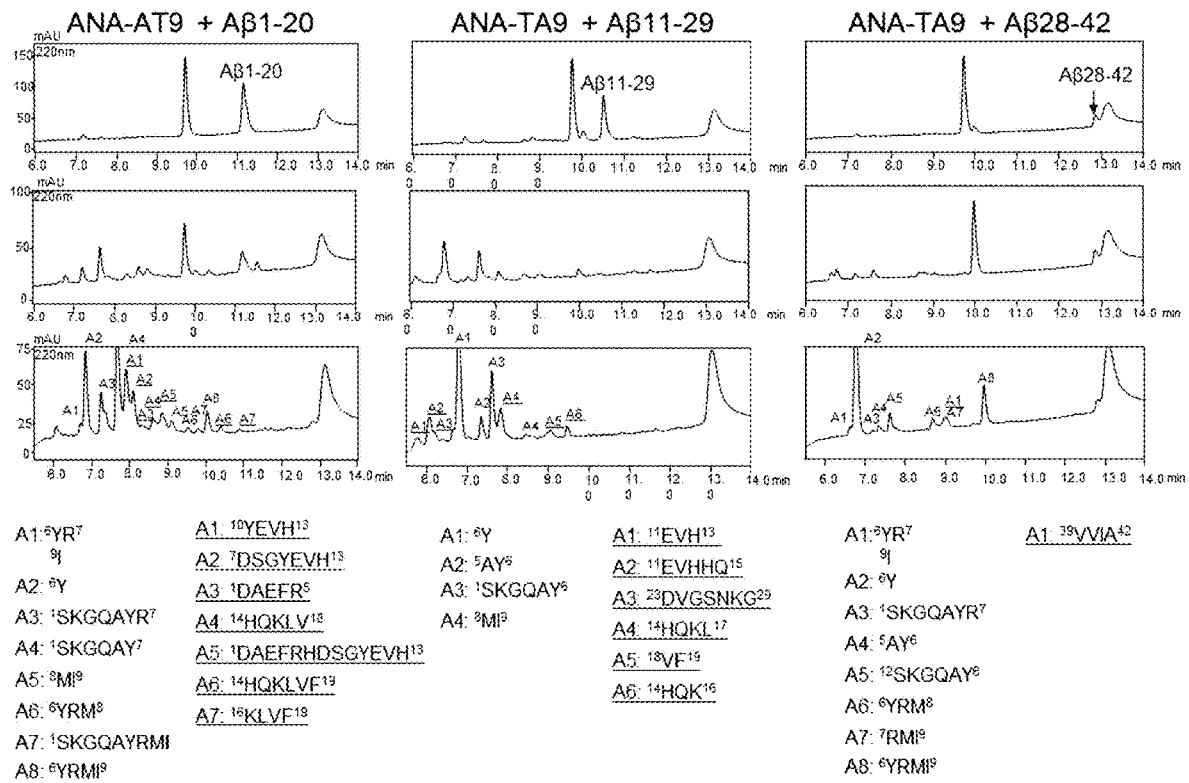
FIG. 54 shows chromatograms showing the hydrolysis activity of the catalytic peptide against Aβ.

The present experiment examined activity against Aβ-Fs in Example 7. As the reaction solution composition, a reaction solution II shown in FIG. 52 was used. The results obtained are shown in FIG. 54. In FIG. 54, the chromatograms on the first row show the results obtained after the reaction for 0 hours, the chromatograms on the second row show the results obtained after the reaction for 1 day, and the chromatograms on the third row show the results obtained after the reaction for 5 days. As can be seen in FIG. 54, ANA-TA9 could cleave all the Aβ-Fs. In FIG. 54, underlined sequences are fragments of Aβ-Fs resulting from the cleavage by ANA-TA9.

(3) Cleavage of Aβ42

Figure 55:
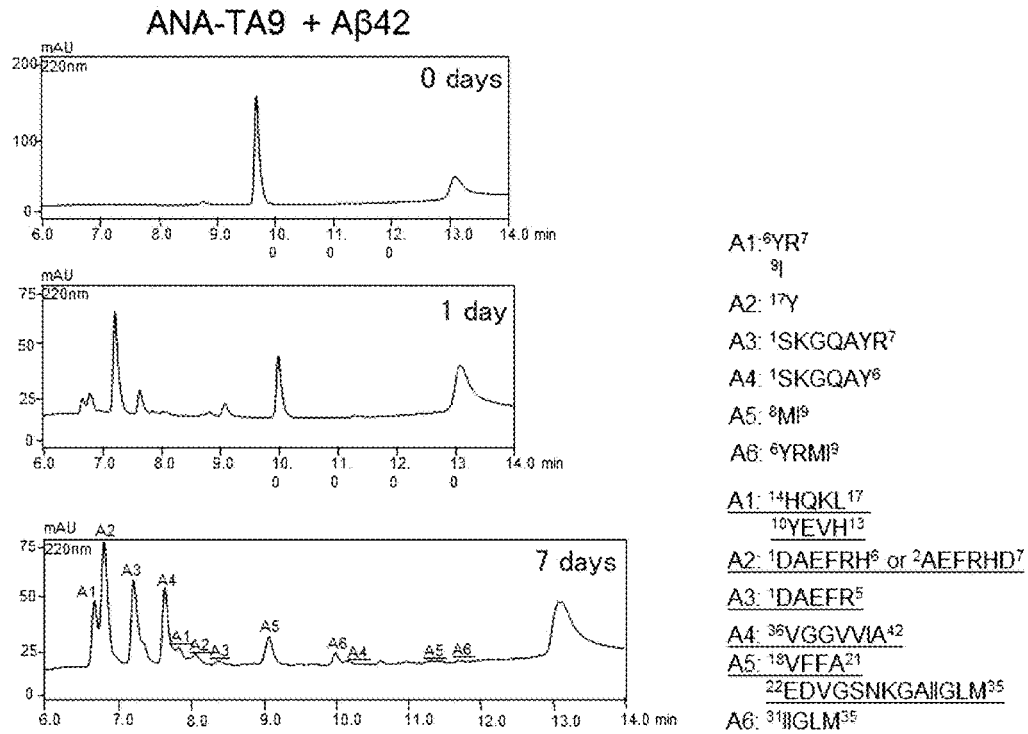
FIG. 55 shows chromatograms showing the hydrolysis activity of the catalytic peptide against Aβ.
Figure 56:
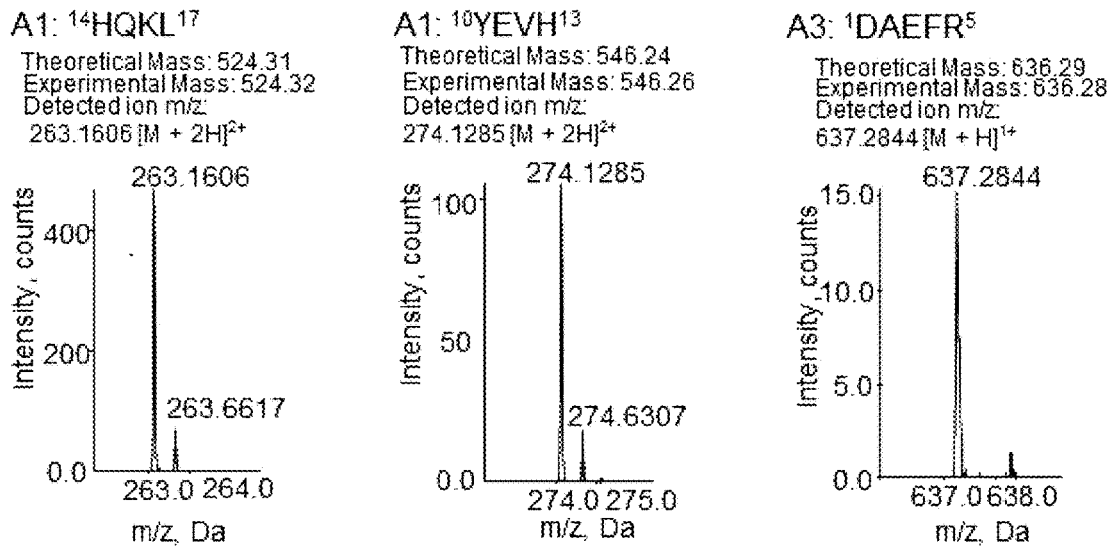
FIG. 56 shows chromatograms showing the hydrolysis activity of the catalytic peptide against Aβ.

The present experiment examined the activity against the authentic sample Aβ42 shown in Example 7. As the reaction solution composition, a reaction solution III shown in FIG. 52 was used. The results obtained are shown in FIGS. 55 and 56. As can be seen in FIGS. 55 and 56, ANA-TA9 could cleave Aβ42. In FIG. 55, underlined sequences are fragments of Aβ42 resulting from the cleavage by ANA-TA9.

(4) Influence of Protease Inhibitor

Figure 57:
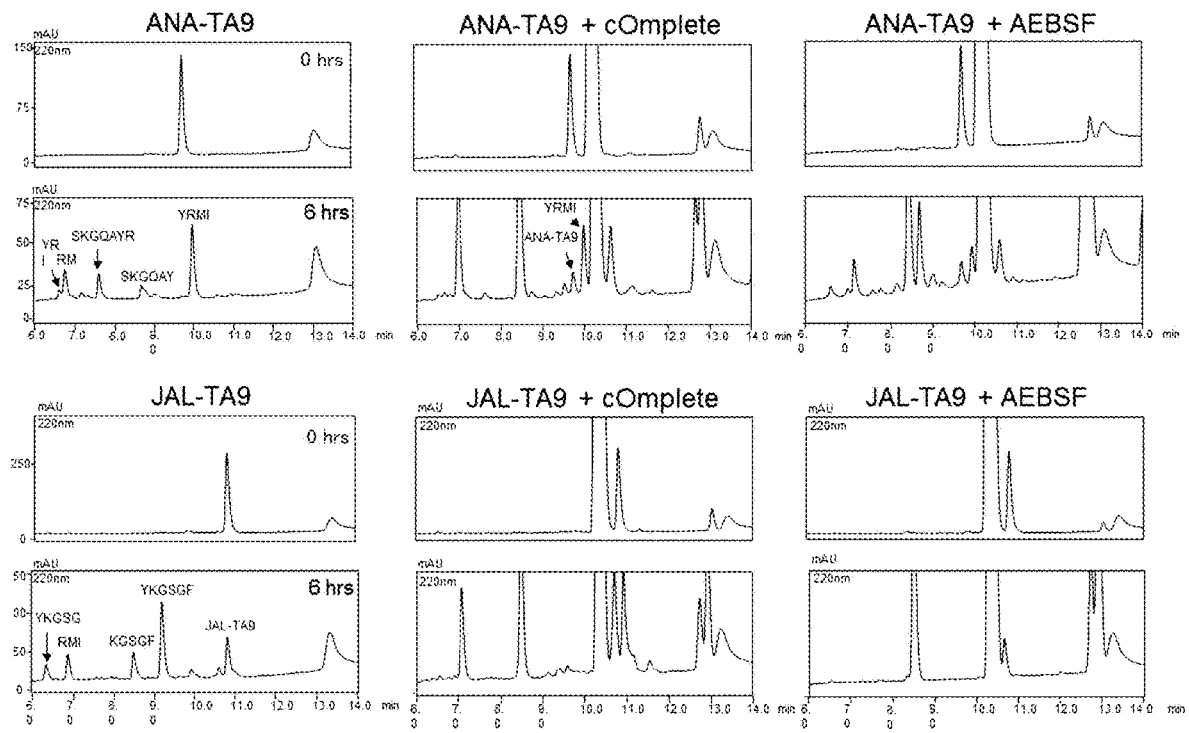
FIG. 57 shows chromatograms showing inhibition of autodigestion of the catalytic peptide by a protease inhibitor.

The influence of a protease inhibitor on autodigestion of ANA-TA9 was examined using a reaction solution IV shown in FIG. 57. FIG. 57 also shows the results obtained regarding JAL-TA9. In FIG. 57, regarding each reaction system, the upper chromatogram shows the result obtained after the reaction for 0 hours, and the lower chromatogram shows the results obtained after the reaction for 6 hours. As can be seen in FIG. 57, autodigestion of both ANA-TA9 and JAL-TA9 were inhibited by the protease inhibitor.

Example 11

The present example examined the hydrolysis activity of ANA-YA4 (also referred to as YRMI) that appears as a result of autodigestion of ANA-TA9.

ANA-SA4:
YRMI
(SEQ ID NO: 54)

(1) Cleavage of Aβ1-20

Figure 58:
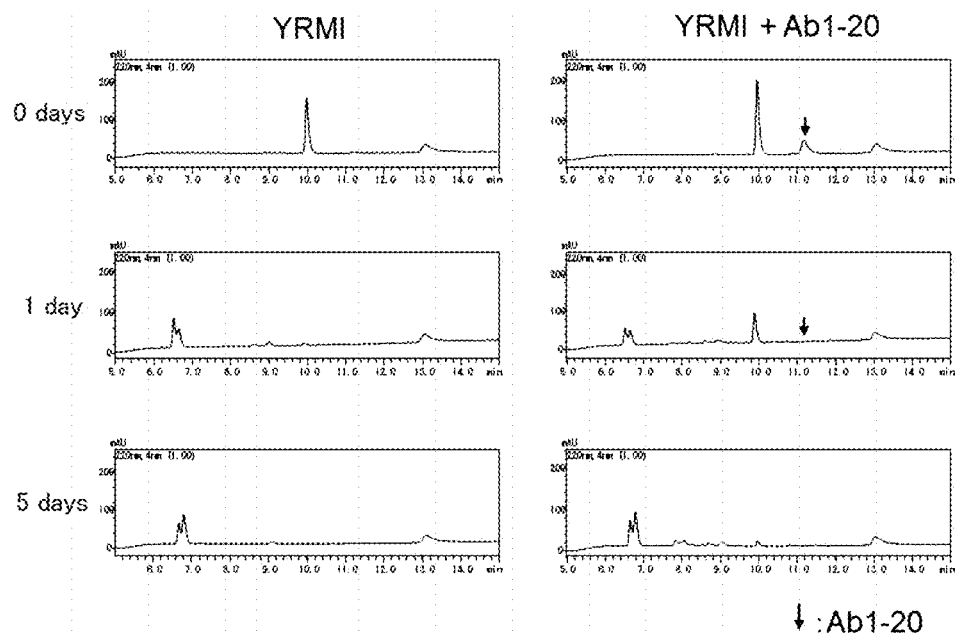
FIG. 58 shows chromatograms showing the hydrolysis activity of the catalytic peptide against Aβ.

A reaction solution V in FIG. 52 was incubated at 37° C. for a predetermined time, and autodigestion of ANA-YA4 (YRMI) and cleavage of Aβ1-20 by ANA-YA4 were examined. The results obtained are shown in FIG. 58. As can be seen in FIG. 58, ANA-SA4 digested itself and also degraded Aβ1-20.

Figure 59:
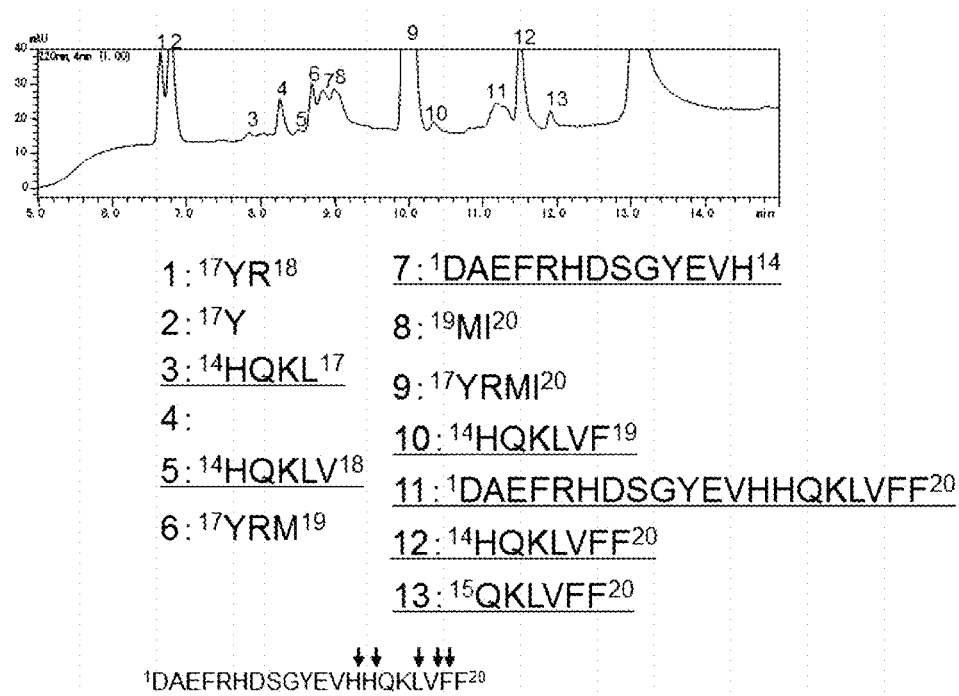
FIG. 59 shows a chromatogram showing the hydrolysis activity of a catalytic peptide against Aβ.

FIG. 59 shows the result of MS after the reaction for 1 day. In FIG. 59, the underlined sequences are fragments of Aβ1-20 resulting from the cleavage by ANA-YA4.

(2) Cleavage of Aβ11-29Aβ-F

Figure 60:
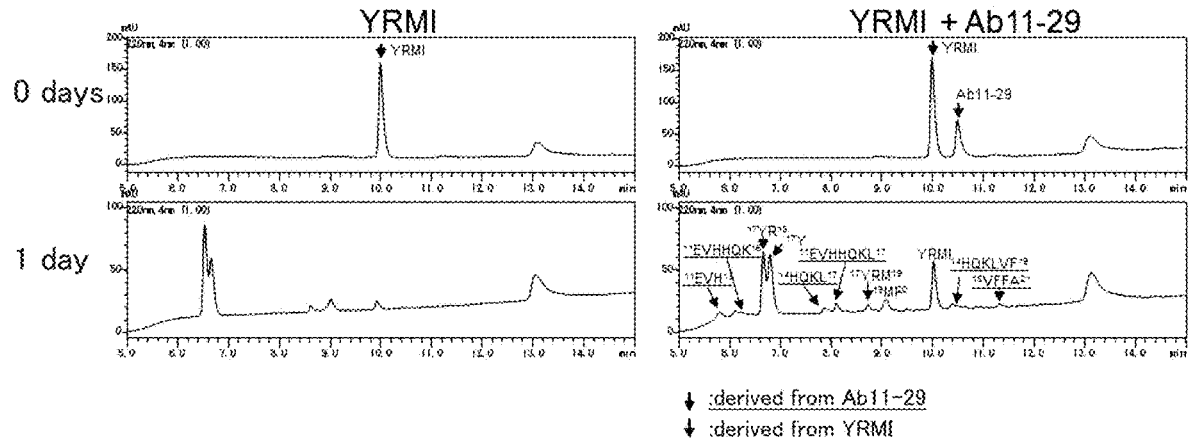
FIG. 60 shows chromatograms showing the hydrolysis activity of the catalytic peptide against Aβ.

The reaction solution V shown in FIG. 52 was incubated at 37° C. for a predetermined time, and autodigestion of ANA-YA4 (YRMI) and cleavage of Aβ11-29 were examined. The results obtained are shown in FIG. 60. As can be seen in FIG. 60, ANA-SA4 digested itself and also degraded Aβ11-29. In FIG. 60, the underlined sequences are fragments of Aβ11-29 resulting from the cleavage by ANA-YA4.

Figure 61:
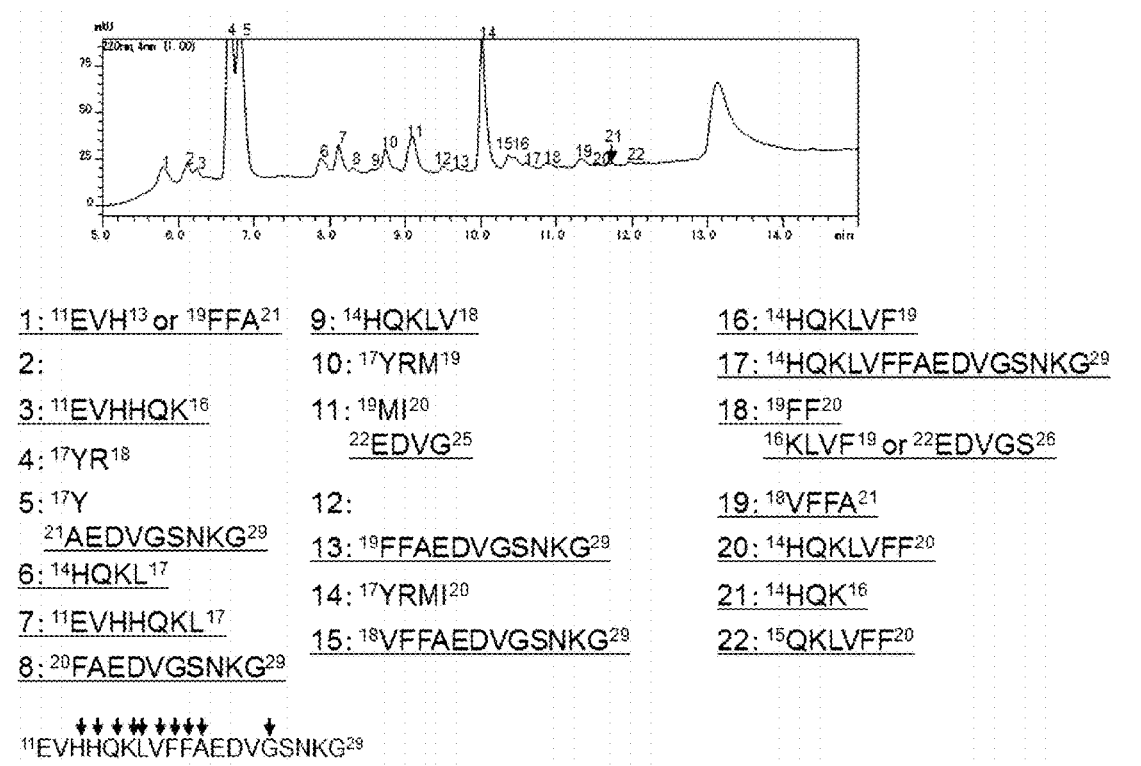
FIG. 61 shows a chromatogram showing the hydrolysis activity of the catalytic peptide against Aβ.

FIG. 61 shows the result of MS after the reaction for 1 day. In FIG. 61, the underlined sequences are fragments of Aβ11-29 resulting from the cleavage by ANA-YA4. FIG. 61 also shows cleavage sites in Aβ11-29 by ANA-YA4.

Example 12

The present example examined the hydrolysis activity of ANA-SA5 that appears as a result of autodigestion of ANA-TA9.

ANA-SA5:
SKGQA
(SEQ ID NO: 55)

Figure 62:
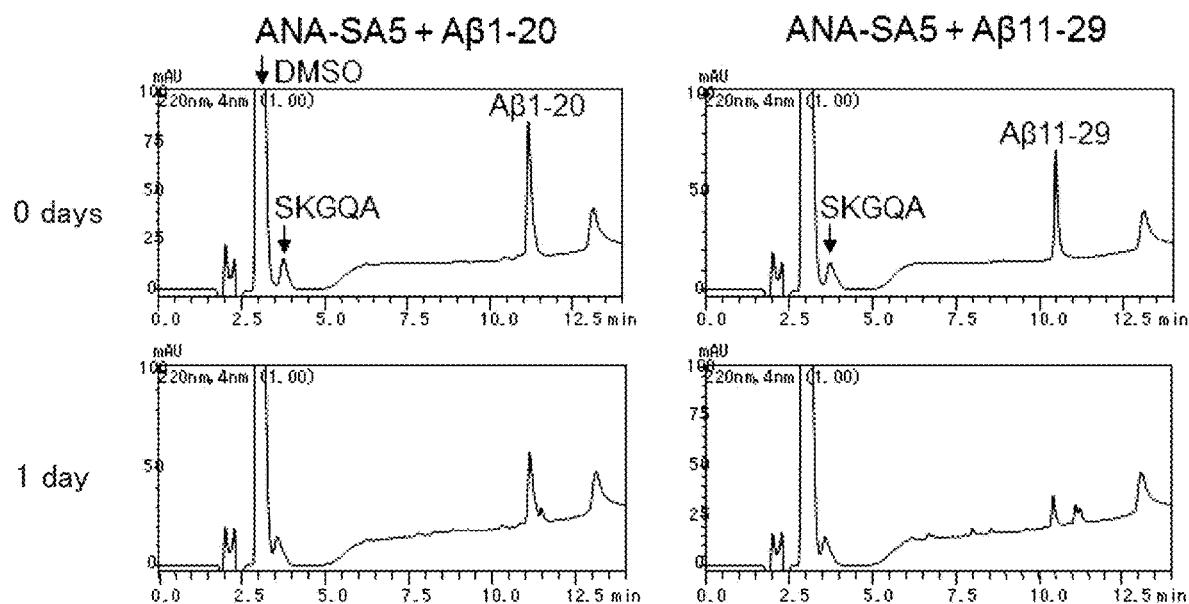
FIG. 62 shows chromatograms showing the hydrolysis activity of a catalytic peptide against Aβ.

A reaction solution VI shown in FIG. 52 was incubated at 37° C. for a predetermined time, and cleavage of Aβ1-20 and Aβ11-29 by ANA-SA5 was examined. The results obtained are shown in FIG. 62. As can be seen in FIG. 62, ANA-SA4 degraded Aβ1-20, whereby the peak was decreased to 49.6% after the reaction for 1 day and the peak almost disappeared after the reaction for 5 days. Then, as can be seen in FIG. 63, 12 types of fragments of Aβ1-20 were detected after the reaction for 5 days. Further, as can be seen in FIG. 62, ANA-SA4 degraded Aβ11-29, whereby the peak was decreased to 72% after the reaction for 1 day and the peak almost disappeared after the reaction for 5 days. Then, as can be seen in FIG. 64, after the reaction for 5 days, 13 types of fragments of Aβ11-29 were detected. FIGS. 63 and 64 also show cleavage sites in Aβ-Fs by ANA-SA5.

Example 13

αA-crystallin has chaperone-like activity and maintains the transparency of the lens. It has been reported that a peptide consisting of 71-88 residues of αA-crystallin inhibits aggregation of amyloid β and that this peptide itself aggregates to form an amyloid fibril. Thus, regarding JAL-TA9 in Example 7, degradation activity of αA-crystallin was examined.

As a substrate, a fragment peptide with the following sequence consisting of 71-88 residues of αA-crystallin (synthesized in Setsunan University) was used. The measurement of activity was performed in the same manner as in the item (1) in Example 1, except that a reaction solution having the following reaction solution composition was used, the reaction solution was incubated at 37° C. for a predetermined time, and 10 µl of the reaction solution then was applied to HPLC. In the case of MS analysis, the MS analysis was performed after applying 20 µl of the reaction solution to HPLC and collecting an aliquot of the peak.

αA-crystallin:
FVIFLDVKHFSPEDLTVK
(SEQ ID NO: 56)

TABLE 13

| (Reaction Solution Composition) | | |
|---|---|---|
| | Added amount | Final concentration |
| 1 mmol/l JAL-TA9 | 20 µl | 0.2 mmol/l |
| 1 mmol/l substrate (10% DMSO) | 5 µl | 0.05 mmol/l |
| PBS | 10 µl | |
| 0.5% HSA | 5 µl | |
| Ultrapure water | 60 µl | |
| Total | 100 µl | |

The results obtained are shown in FIG. 65. As can be seen in FIG. 65, JAL-TA9 digested itself and also could degrade αA-crystallin after the reaction for 1 day. Further, as can be seen in FIG. 66, fragments of αA-crystallin resulting from the cleavage by JAL-TA9 were detected. In FIG. 66, underlined sequences are fragments of αA-crystallin resulting from the cleavage by JAL-TA9. FIG. 65 also shows cleavage sites in αA-crystallin.

Example 14

JAL-TA9 is derived from the Box A domain of Tob1. Thus, the measurement of activity was performed on a peptide (Tob1 Box B 8-20: WIDPFEVSYQIGE) derived from the Box B domain (SEQ ID NO: 34) of Tob1. As substrates, the same Aβ1-20 and Aβ11-29 as used in Example 7 were used. The measurement of activity was performed in the same manner as in Example 7, except that a reaction solution having the following reaction solution composition was used.

TABLE 14

| (Reaction Solution Composition) | | |
|---|---|---|
| | Added amount | Final concentration |
| 1 mmol/l Tob1 Box B 8-20 | 20 µl | 0.2 mmol/l |
| 1 mmol/l substrate | 5 µl | 0.05 mmol/l |
| 10% DMSO | 5 µl | 0.5% |
| PBS | 10 µl | |
| 0.5% HSA | 5 µl | |
| Ultrapure water | 55 µl | |
| Total | 100 µl | |

(1) Activity Against Aβ-Fs

The results obtained are shown in FIG. 66. FIG. 66 shows the result of the HPLC analysis of the reaction solution. As can be seen in FIG. 66, similarly to the peptide derived from Box A, Tob1 Box B 8-20 degraded Aβ-Fs. This demonstrates that Tob1 Box B 8-20 has activity against Aβ-Fs.

(2) Identification of Cleavage Sites in Aβ-Fs

Figure 67:
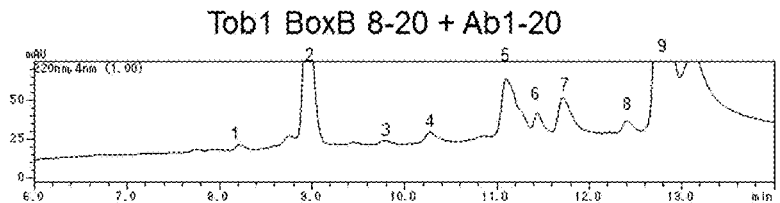
FIG. 67 shows a chromatogram showing the hydrolysis activity of the catalytic peptide against Aβ.
Figure 68:
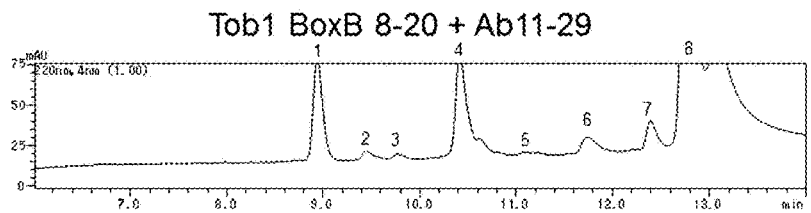
FIG. 68 shows a chromatogram showing the hydrolysis activity of the catalytic peptide against Aβ.

The results obtained are shown in FIGS. 67 and 68. FIGS. 67 and 68 show the results of fragment identification by MS, and show the sequences of fragments obtained by degradation. In each of FIGS. 67 and 68, underlined sequences are fragments derived from Aβ-F. As can be seen in FIGS. 67 and 68, both the Aβ-Fs were cleaved at a plurality of sites.

Example 15

The present example examined autodigestion and activity against Aβ-F of JAL 12-17 (YKGSGF) and JAL 12-16 (YKGSG). The measurement of activity was performed in the same manner as in Example 7, except that a reaction solution having the following reaction solution composition was used. As a substrate, the same Aβ11-29 as used in Example 7 was used. The autodigestion was examined by causing the reaction in the same manner, except that the substrate was not added.

TABLE 15

| (Reaction Solution Composition) | | |
|---|---|---|
| | Added amount | Final concentration |
| 1 mmol/l JAL | 20 μl | 0.2 mmol/l |
| 1 mmol/l substrate | 5 μl | 0.05 mmol/l |
| 10% DMSO | 5 μl | 0.5% |
| PBS | 10 μl | |
| 0.05% HSA | 50 μl | |
| Ultrapure water | 10 μl | |
| Total | 100 μl | |

Figure 69:
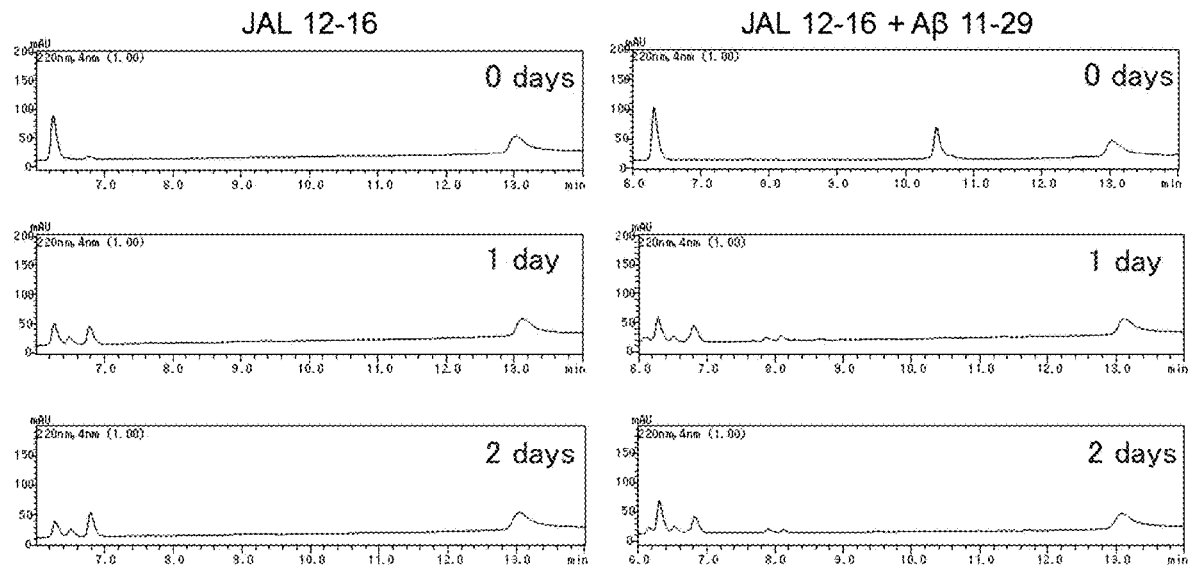
FIG. 69 shows chromatograms showing the hydrolysis activity of a catalytic peptide against Aβ.
Figure 70:
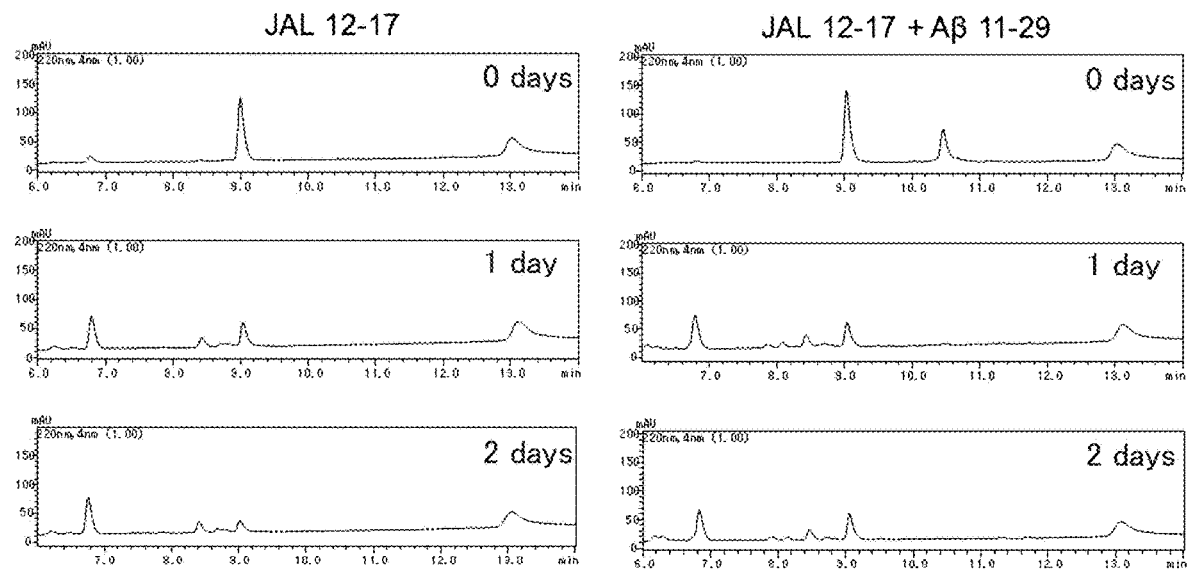
FIG. 70 shows chromatograms showing the hydrolysis activity of a catalytic peptide against Aβ.

The results obtained are shown in FIGS. 69 and 70. FIGS. 69 and 70 show the results of the HPLC analysis of the reaction solution. As can be seen in FIGS. 69 and 70, both JAL 12-17 and JAL 12-16 digested themselves and degraded Aβ-F.

FIG. 71 shows, as the result of fragment identification by MS after the reaction for 3 days, the sequences of fragments obtained by degradation. FIG. 71 shows the results obtained regarding the autodigestion, and FIG. 72 shows the results obtained regarding the degradation of Aβ-F. As can be seen in the upper chromatogram in FIG. 71, an increase in JAL 12-14 (P2) was observed when JAL 12-16 was used. Further, as can be seen in the lower chromatogram in FIG. 71, an increase in JAL 13-17 (P5) was observed when JAL 12-17 was used.

FIG. 72 shows, as the result of fragment identification by MS, the sequences of fragments obtained by degradation. In FIG. 72, underlined sequences are fragments derived from Aβ-F. As can be seen in FIG. 72, cleavage sites in Aβ-F by JAL 12-17 were the same as those by JAL 12-16.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

INDUSTRIAL APPLICABILITY

The catalytic peptide of the present invention can catalyze a hydrolysis reaction. Unlike enzyme proteins, the catalytic peptide of the present invention is a peptide having a low molecular weight. Thus, the catalytic peptide of the present invention is applicable to a hydrolysis reaction as a novel catalytic molecule different from the proteins.

[Sequence Listing]
TF15112WO_ST25.txt

The invention claimed is:

1. A catalytic peptide that catalyzes a hydrolysis reaction, wherein the catalytic peptide is selected from the group consisting of SEQ ID Nos: 2, 4-9, 11, 13, 16-17, 20, 22-31, 36-37, 40, 50, 53-55, 59-60;
wherein in SEQ ID NO: 27, Xaa is W, L, V, N, or D;
wherein in SEQ ID NO: 28, Xaa is K, V, Y, or M;
wherein in SEQ ID NO: 29, Xaa is T, E, or P,
wherein in SEQ ID NO: 30, Xaa is H, V, Y, Q, N, or G; and
wherein in SEQ ID NO: 31, Xaa is T, Q, V, K, or E.

2. The catalytic peptide according to claim 1, wherein the number of amino acid residues in the peptide is in a range from 5 to 22.

3. A catalytic peptide reagent comprising:
a catalytic molecule,
wherein the catalytic molecule is the catalytic peptide according to claim 1; and
a molecule that is different from the catalytic peptide.

4. The catalytic peptide reagent according to claim 3, wherein the molecule that is different from the catalytic peptide is linked to the catalytic peptide.

5. The catalytic peptide reagent according to claim 4, wherein
the molecule that is different from the catalytic peptide is a binding molecule that binds to a target.

6. The catalytic peptide reagent according to claim 5, wherein
the binding molecule is a protein or a peptide.

7. A method for degrading a protein or a peptide, the method comprising the step of:
treating a substrate with the catalytic peptide according to claim 1, wherein the substrate is a protein or a peptide.

* * * * *

UNITED STATES PATENT AND TRADEMARK OFFICE
CERTIFICATE OF CORRECTION

PATENT NO. : 10,995,119 B2
APPLICATION NO. : 16/067764
DATED : May 4, 2021
INVENTOR(S) : Akizawa et al.

Page 1 of 1

It is certified that error appears in the above-identified patent and that said Letters Patent is hereby corrected as shown below:

Column 52, Claim 7: delete:
"A method for degrading a protein or a peptide, the method comprising the step of: treating a substrate with the catalytic peptide according to claim 1, wherein the substrate is a protein or a peptide."

And insert:
--A method for degrading a protein or a peptide, the method comprising the step of: treating a substrate with the catalytic peptide according to claim 1, wherein the substrate is an amyloid beta protein or a fragment peptide thereof, a prion protein or a fragment peptide thereof, hMMP7 or a fragment peptide thereof, SOD1 or a fragment peptide thereof, a Tau protein or a fragment peptide thereof, or a crystallin or a fragment peptide thereof.--

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 60

<210> SEQ ID NO 1
<211> LENGTH: 18
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (3)..(3)
<223> OTHER INFORMATION: X is Y, F or H.
<220> FEATURE:
<221> NAME/KEY: MISC_FEATURE
<222> LOCATION: (4)..(4)
<223> OTHER INFORMATION: X is P or S.
<220> FEATURE:
<221> NAME/KEY: MISC_FEATURE
<222> LOCATION: (5)..(5)
<223> OTHER INFORMATION: X is E or D.
<220> FEATURE:
<221> NAME/KEY: MISC_FEATURE
<222> LOCATION: (6)..(6)
<223> OTHER INFORMATION: X is K or C.
<220> FEATURE:
<221> NAME/KEY: MISC_FEATURE
<222> LOCATION: (8)..(8)
<223> OTHER INFORMATION: X is Y, L, C or S.
<220> FEATURE:
<221> NAME/KEY: MISC_FEATURE
<222> LOCATION: (11)..(11)
<223> OTHER INFORMATION: X is S or Q.
```

```
<220> FEATURE:
<221> NAME/KEY: MISC_FEATURE
<222> LOCATION: (12)..(12)
<223> OTHER INFORMATION: X is G or A.
<220> FEATURE:
<221> NAME/KEY: MISC_FEATURE
<222> LOCATION: (13)..(13)
<223> OTHER INFORMATION: X is F or Y.
<220> FEATURE:
<221> NAME/KEY: MISC_FEATURE
<222> LOCATION: (16)..(16)
<223> OTHER INFORMATION: X is V or I.
<220> FEATURE:
<221> NAME/KEY: MISC_FEATURE
<222> LOCATION: (17)..(17)
<223> OTHER INFORMATION: X is H or R.
<220> FEATURE:
<221> NAME/KEY: MISC_FEATURE
<222> LOCATION: (18)..(18)
<223> OTHER INFORMATION: X is I or V.

<400> SEQUENCE: 1

His Trp Xaa Xaa Xaa Xaa Pro Xaa Lys Gly Xaa Xaa Xaa Arg Cys Xaa
1               5                   10                  15

Xaa Xaa

<210> SEQ ID NO 2
<211> LENGTH: 22
<212> TYPE: PRT
<213> ORGANISM: Artificial Sequence
<220> FEATURE:
<223> OTHER INFORMATION: polypeptide

<400> SEQUENCE: 2

Lys Tyr Glu Gly His Trp Tyr Pro Glu Lys Pro Tyr Lys Gly Ser Gly
1               5                   10                  15

Phe Arg Cys Ile His Ile
            20

<210> SEQ ID NO 3
<211> LENGTH: 18
<212> TYPE: PRT
<213> ORGANISM: Artificial Sequence
<220> FEATURE:
<223> OTHER INFORMATION: polypeptide

<400> SEQUENCE: 3

His Trp Tyr Pro Glu Lys Pro Tyr Lys Gly Ser Gly Phe Arg Cys Ile
1               5                   10                  15

His Ile

<210> SEQ ID NO 4
<211> LENGTH: 16
<212> TYPE: PRT
<213> ORGANISM: Artificial Sequence
<220> FEATURE:
<223> OTHER INFORMATION: polypeptide

<400> SEQUENCE: 4

Tyr Pro Glu Lys Pro Tyr Lys Gly Ser Gly Phe Arg Cys Ile His Ile
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: polypeptide
```

```
<400> SEQUENCE: 5

Tyr Pro Glu Lys Pro Leu Lys Gly Ser Gly Phe Arg Cys Val His Ile
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: polypeptide

<400> SEQUENCE: 6

Phe Pro Glu Lys Pro Cys Lys Gly Ser Gly Tyr Arg Cys Ile Arg Ile
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: polypeptide

<400> SEQUENCE: 7

Phe Pro Glu Lys Pro Ser Lys Gly Ser Gly Tyr Arg Cys Ile Arg Ile
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: polypeptide

<400> SEQUENCE: 8

Tyr Pro Glu Lys Pro Ser Lys Gly Gln Ala Tyr Arg Cys Ile Arg Val
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: polypeptide

<400> SEQUENCE: 9

His Ser Asp Cys Pro Ser Lys Gly Gln Ala Phe Arg Cys Ile Arg Ile
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: polypeptide

<400> SEQUENCE: 10

Tyr Glu Gly His Trp Tyr Pro Glu Lys Pro Tyr Lys Gly Ser Gly Phe
1               5                   10                  15

Arg

<210> SEQ ID NO 11
<211> LENGTH: 7
<212> TYPE: PRT
<213> ORGANISM: Artificial Sequence
<220> FEATURE:
```

```
<223> OTHER INFORMATION: polypeptide

<400> SEQUENCE: 11

Tyr Lys Gly Ser Gly Phe Arg
1               5

<210> SEQ ID NO 12
<211> LENGTH: 5
<212> TYPE: PRT
<213> ORGANISM: Artificial Sequence
<220> FEATURE:
<223> OTHER INFORMATION: polypeptide

<400> SEQUENCE: 12

Lys Gly Ser Gly Phe
1               5

<210> SEQ ID NO 13
<211> LENGTH: 5
<212> TYPE: PRT
<213> ORGANISM: Artificial Sequence
<220> FEATURE:
<223> OTHER INFORMATION: polypeptide

<400> SEQUENCE: 13

Gly Ser Gly Phe Arg
1               5

<210> SEQ ID NO 14
<211> LENGTH: 9
<212> TYPE: PRT
<213> ORGANISM: Artificial Sequence
<220> FEATURE:
<223> OTHER INFORMATION: polypeptide

<400> SEQUENCE: 14

Gly Ser Gly Phe Arg Cys Ile His Ile
1               5

<210> SEQ ID NO 15
<211> LENGTH: 7
<212> TYPE: PRT
<213> ORGANISM: Artificial Sequence
<220> FEATURE:
<223> OTHER INFORMATION: polypeptide

<400> SEQUENCE: 15

Lys Gly Ser Gly Phe Arg Met
1               5

<210> SEQ ID NO 16
<211> LENGTH: 22
<212> TYPE: PRT
<213> ORGANISM: Artificial Sequence
<220> FEATURE:
<223> OTHER INFORMATION: polypeptide

<400> SEQUENCE: 16

Lys Tyr Glu Gly His Trp Tyr Pro Glu Lys Pro Tyr Lys Gly Ser Gly
1               5                   10                  15

Phe Arg Met Ile His Ile
            20

<210> SEQ ID NO 17
<211> LENGTH: 16
<212> TYPE: PRT
```

```
<213> ORGANISM: Artificial Sequence
<220> FEATURE:
<223> OTHER INFORMATION: polypeptide

<400> SEQUENCE: 17

Tyr Pro Glu Lys Pro Tyr Lys Gly Ser Gly Phe Arg Met Ile His Ile
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: polypeptide

<400> SEQUENCE: 18

Tyr Pro Ala Lys Pro Tyr Lys Gly Ser Gly Phe Arg Met Ile His Ile
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: polypeptide

<400> SEQUENCE: 19

Tyr Trp Ala Lys Pro Tyr Lys Gly Ser Gly Phe Arg Met Ile His Ile
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: polypeptide

<400> SEQUENCE: 20

Ala Pro Glu Lys Pro Tyr Lys Gly Ser Gly Phe Arg Met Ile His Ala
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: polypeptide

<400> SEQUENCE: 21

Ala Pro Glu Ala Pro Tyr Lys Gly Ser Gly Phe Arg Met Ile His Ala
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: polypeptide

<400> SEQUENCE: 22

Glu Lys Pro Tyr Lys Gly Ser Gly Phe Arg Met Ile
1               5                   10

<210> SEQ ID NO 23
<211> LENGTH: 11
<212> TYPE: PRT
<213> ORGANISM: Artificial Sequence
```

```
<220> FEATURE:
<223> OTHER INFORMATION: polypeptide

<400> SEQUENCE: 23

Tyr Lys Gly Ser Gly Phe Arg Met Ile His Ala
1               5                   10

<210> SEQ ID NO 24
<211> LENGTH: 9
<212> TYPE: PRT
<213> ORGANISM: Artificial Sequence
<220> FEATURE:
<223> OTHER INFORMATION: polypeptide

<400> SEQUENCE: 24

Tyr Lys Gly Ser Gly Phe Arg Met Ile
1               5

<210> SEQ ID NO 25
<211> LENGTH: 9
<212> TYPE: PRT
<213> ORGANISM: Artificial Sequence
<220> FEATURE:
<223> OTHER INFORMATION: polypeptide

<400> SEQUENCE: 25

Ala Lys Gly Ser Gly Phe Arg Met Ile
1               5

<210> SEQ ID NO 26
<211> LENGTH: 7
<212> TYPE: PRT
<213> ORGANISM: Artificial Sequence
<220> FEATURE:
<223> OTHER INFORMATION: polypeptide

<400> SEQUENCE: 26

Tyr Lys Gly Ala Gly Phe Arg
1               5

<210> SEQ ID NO 27
<211> LENGTH: 5
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (1)..(1)
<223> OTHER INFORMATION: X is W, L, V, N or D.

<400> SEQUENCE: 27

Xaa Ser Gly Phe Arg
1               5

<210> SEQ ID NO 28
<211> LENGTH: 5
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (2)..(2)
<223> OTHER INFORMATION: X is K V T, Y or M.

<400> SEQUENCE: 28

Gly Xaa Gly Phe Arg
```

1               5

<210> SEQ ID NO 29
<211> LENGTH: 5
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (3)..(3)
<223> OTHER INFORMATION: X is T, E, P, W or K.

<400> SEQUENCE: 29

Gly Ser Xaa Phe Arg
1               5

<210> SEQ ID NO 30
<211> LENGTH: 5
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (4)..(4)
<223> OTHER INFORMATION: X is H, V, W, Y, R, L, P, M, E, A, D, Q, N, K
      or G.

<400> SEQUENCE: 30

Gly Ser Gly Xaa Arg
1               5

<210> SEQ ID NO 31
<211> LENGTH: 5
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (5)..(5)
<223> OTHER INFORMATION: X is T, Q, V, K or E.

<400> SEQUENCE: 31

Gly Ser Gly Phe Xaa
1               5

<210> SEQ ID NO 32
<211> LENGTH: 20
<212> TYPE: PRT
<213> ORGANISM: Artificial Sequence
<220> FEATURE:
<223> OTHER INFORMATION: polypeptide
<220> FEATURE:
<221> NAME/KEY: MISC_FEATURE
<222> LOCATION: (1)..(1)
<223> OTHER INFORMATION: X is V or L.
<220> FEATURE:
<221> NAME/KEY: MISC_FEATURE
<222> LOCATION: (3)..(3)
<223> OTHER INFORMATION: X is Q, E, S or K.
<220> FEATURE:
<221> NAME/KEY: MISC_FEATURE
<222> LOCATION: (4)..(4)
<223> OTHER INFORMATION: X is D or E.
<220> FEATURE:
<221> NAME/KEY: MISC_FEATURE
<222> LOCATION: (5)..(5)
<223> OTHER INFORMATION: X is L or M.
<220> FEATURE:
<221> NAME/KEY: MISC_FEATURE
<222> LOCATION: (6)..(6)
<223> OTHER INFORMATION: X is S or T.
<220> FEATURE:
<221> NAME/KEY: MISC_FEATURE
<222> LOCATION: (7)..(7)
<223> OTHER INFORMATION: X is V, L or I.
<220> FEATURE:
<221> NAME/KEY: MISC_FEATURE
<222> LOCATION: (9)..(9)
<223> OTHER INFORMATION: X is V or I.
<220> FEATURE:
<221> NAME/KEY: MISC_FEATURE
<222> LOCATION: (12)..(12)
<223> OTHER INFORMATION: X is F, Y or C.
<220> FEATURE:
<221> NAME/KEY: MISC_FEATURE
<222> LOCATION: (13)..(13)
<223> OTHER INFORMATION: X is E or R.
<220> FEATURE:
<221> NAME/KEY: MISC_FEATURE
<222> LOCATION: (15)..(15)
<223> OTHER INFORMATION: X is S or C.
<220> FEATURE:
<221> NAME/KEY: MISC_FEATURE
<222> LOCATION: (16)..(16)
<223> OTHER INFORMATION: X is Y or C.
<220> FEATURE:
<221> NAME/KEY: MISC_FEATURE
<222> LOCATION: (17)..(17)
<223> OTHER INFORMATION: X is Q or R.
<220> FEATURE:
<221> NAME/KEY: MISC_FEATURE
<222> LOCATION: (18)..(18)
<223> OTHER INFORMATION: X is I or Y.

<400> SEQUENCE: 32

Xaa Pro Xaa Xaa Xaa Xaa Xaa Trp Xaa Asp Pro Xaa Xaa Val Xaa Xaa
1               5                   10                  15

Xaa Xaa Gly Glu
            20

<210> SEQ ID NO 33
<211> LENGTH: 20
<212> TYPE: PRT
<213> ORGANISM: Artificial Sequence
<220> FEATURE:
<223> OTHER INFORMATION: polypeptide

<400> SEQUENCE: 33

Leu Pro Ser Glu Leu Thr Leu Trp Val Asp Pro Tyr Glu Val Ser Tyr
1               5                   10                  15

Arg Ile Gly Glu
            20

<210> SEQ ID NO 34
<211> LENGTH: 20
<212> TYPE: PRT
<213> ORGANISM: Artificial Sequence
<220> FEATURE:
<223> OTHER INFORMATION: polypeptide

<400> SEQUENCE: 34

Leu Pro Gln Asp Leu Ser Val Trp Ile Asp Pro Phe Glu Val Ser Tyr
1               5                   10                  15

Gln Ile Gly Glu
            20

<210> SEQ ID NO 35
<211> LENGTH: 20
<212> TYPE: PRT

```
<213> ORGANISM: Artificial Sequence
<220> FEATURE:
<223> OTHER INFORMATION: polypeptide

<400> SEQUENCE: 35

Leu Pro Lys Glu Leu Thr Leu Trp Val Asp Pro Cys Arg Val Cys Cys
1               5                   10                  15

Arg Tyr Gly Glu
            20

<210> SEQ ID NO 36
<211> LENGTH: 13
<212> TYPE: PRT
<213> ORGANISM: Artificial Sequence
<220> FEATURE:
<223> OTHER INFORMATION: polypeptide

<400> SEQUENCE: 36

Trp Val Asp Pro Tyr Glu Val Ser Tyr Arg Ile Gly Glu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: polypeptide

<400> SEQUENCE: 37

Trp Ile Asp Pro Phe Glu Val Ser Tyr Gln Ile Gly Glu
1               5                   10

<210> SEQ ID NO 38
<211> LENGTH: 13
<212> TYPE: PRT
<213> ORGANISM: Artificial Sequence
<220> FEATURE:
<223> OTHER INFORMATION: polypeptide

<400> SEQUENCE: 38

Trp Asn Asp Pro Cys Arg Val Cys Cys Arg Tyr Gly Glu
1               5                   10

<210> SEQ ID NO 39
<211> LENGTH: 24
<212> TYPE: PRT
<213> ORGANISM: Artificial Sequence
<220> FEATURE:
<223> OTHER INFORMATION: polypeptide

<400> SEQUENCE: 39

Ser Asn Lys Val Ala Arg Thr Ser Pro Ile Asn Leu Gly Leu Asn Val
1               5                   10                  15

Asn Asp Leu Leu Lys Gln Lys Ala
            20

<210> SEQ ID NO 40
<211> LENGTH: 16
<212> TYPE: PRT
<213> ORGANISM: Artificial Sequence
<220> FEATURE:
<223> OTHER INFORMATION: polypeptide

<400> SEQUENCE: 40

Ala Ile Ser Ser Ser Met His Ser Leu Tyr Gly Leu Gly Leu Gly Ser
1               5                   10                  15
```

<210> SEQ ID NO 41
<211> LENGTH: 14
<212> TYPE: PRT
<213> ORGANISM: Artificial Sequence
<220> FEATURE:
<223> OTHER INFORMATION: polypeptide

<400> SEQUENCE: 41

Asp Arg Asn His Trp Ile Asn Pro His Met Leu Ala Pro His
1               5                   10

<210> SEQ ID NO 42
<211> LENGTH: 14
<212> TYPE: PRT
<213> ORGANISM: Artificial Sequence
<220> FEATURE:
<223> OTHER INFORMATION: polypeptide

<400> SEQUENCE: 42

Asp Arg Asn His Trp Ile Asn Ala His Met Leu Ala Pro His
1               5                   10

<210> SEQ ID NO 43
<211> LENGTH: 14
<212> TYPE: PRT
<213> ORGANISM: Artificial Sequence
<220> FEATURE:
<223> OTHER INFORMATION: polypeptide

<400> SEQUENCE: 43

Asp Arg Asn His Trp Ile Asn Ala His Met Leu Ala Ala His
1               5                   10

<210> SEQ ID NO 44
<211> LENGTH: 18
<212> TYPE: PRT
<213> ORGANISM: Artificial Sequence
<220> FEATURE:
<223> OTHER INFORMATION: polypeptide

<400> SEQUENCE: 44

His Trp Tyr Pro Glu Lys Pro Leu Lys Gly Ser Gly Phe Arg Cys Val
1               5                   10                  15

His Ile

<210> SEQ ID NO 45
<211> LENGTH: 18
<212> TYPE: PRT
<213> ORGANISM: Artificial Sequence
<220> FEATURE:
<223> OTHER INFORMATION: polypeptide

<400> SEQUENCE: 45

His Trp Phe Pro Glu Lys Pro Cys Lys Gly Ser Gly Tyr Arg Cys Ile
1               5                   10                  15

Arg Ile

<210> SEQ ID NO 46
<211> LENGTH: 18
<212> TYPE: PRT
<213> ORGANISM: Artificial Sequence
<220> FEATURE:
<223> OTHER INFORMATION: polypeptide

<400> SEQUENCE: 46

```
His Trp Phe Pro Glu Lys Pro Ser Lys Gly Ser Gly Tyr Arg Cys Ile
1               5                   10                  15

Arg Ile
```

<210> SEQ ID NO 47
<211> LENGTH: 18
<212> TYPE: PRT
<213> ORGANISM: Artificial Sequence
<220> FEATURE:
<223> OTHER INFORMATION: polypeptide

<400> SEQUENCE: 47

```
His Trp Tyr Pro Glu Lys Pro Ser Lys Gly Gln Ala Tyr Arg Cys Ile
1               5                   10                  15

Arg Val
```

<210> SEQ ID NO 48
<211> LENGTH: 18
<212> TYPE: PRT
<213> ORGANISM: Artificial Sequence
<220> FEATURE:
<223> OTHER INFORMATION: polypeptide

<400> SEQUENCE: 48

```
His Trp His Ser Asp Cys Pro Ser Lys Gly Gln Ala Phe Arg Cys Ile
1               5                   10                  15

Arg Ile
```

<210> SEQ ID NO 49
<211> LENGTH: 42
<212> TYPE: PRT
<213> ORGANISM: Artificial Sequence
<220> FEATURE:
<223> OTHER INFORMATION: polypeptide

<400> SEQUENCE: 49

```
Met Arg Leu Thr Val Leu Cys Ala Val Cys Leu Leu Pro Gly Ser Leu
1               5                   10                  15

Ala Leu Pro Leu Pro Gln Glu Ala Gly Gly Met Ser Glu Leu Gln Trp
            20                  25                  30

Glu Gln Ala Gln Asp Tyr Leu Lys Arg Phe
        35                  40
```

<210> SEQ ID NO 50
<211> LENGTH: 10
<212> TYPE: PRT
<213> ORGANISM: Artificial Sequence
<220> FEATURE:
<223> OTHER INFORMATION: polypeptide

<400> SEQUENCE: 50

```
Pro Tyr Lys Gly Ser Gly Phe Arg Met Ile
1               5                   10
```

<210> SEQ ID NO 51
<211> LENGTH: 30
<212> TYPE: PRT
<213> ORGANISM: Artificial Sequence
<220> FEATURE:
<223> OTHER INFORMATION: polypeptide

<400> SEQUENCE: 51

```
Gly Ser Lys Asp Asn Ile Lys His Val Pro Gly Gly Gly Ser Val Gln
```

```
1               5                   10                  15
Ile Val Tyr Lys Pro Val Asp Leu Ser Lys Val Thr Ser Lys
            20                  25                  30
```

<210> SEQ ID NO 52
<211> LENGTH: 29
<212> TYPE: PRT
<213> ORGANISM: Artificial Sequence
<220> FEATURE:
<223> OTHER INFORMATION: polypeptide

<400> SEQUENCE: 52

```
Phe Val Ile Phe Leu Asp Val Lys His Phe Ser Pro Glu Asp Leu Thr
1               5                   10                  15

Val Lys Ala Ala Tyr Lys Gly Ser Gly Phe Arg Met Ile
            20                  25
```

<210> SEQ ID NO 53
<211> LENGTH: 9
<212> TYPE: PRT
<213> ORGANISM: Artificial Sequence
<220> FEATURE:
<223> OTHER INFORMATION: polypeptide

<400> SEQUENCE: 53

```
Ser Lys Gly Gln Ala Tyr Arg Met Ile
1               5
```

<210> SEQ ID NO 54
<211> LENGTH: 4
<212> TYPE: PRT
<213> ORGANISM: Artificial Sequence
<220> FEATURE:
<223> OTHER INFORMATION: polypeptide

<400> SEQUENCE: 54

```
Tyr Arg Met Ile
1
```

<210> SEQ ID NO 55
<211> LENGTH: 5
<212> TYPE: PRT
<213> ORGANISM: Artificial Sequence
<220> FEATURE:
<223> OTHER INFORMATION: polypeptide

<400> SEQUENCE: 55

```
Ser Lys Gly Gln Ala
1               5
```

<210> SEQ ID NO 56
<211> LENGTH: 18
<212> TYPE: PRT
<213> ORGANISM: Artificial Sequence
<220> FEATURE:
<223> OTHER INFORMATION: polypeptide

<400> SEQUENCE: 56

```
Phe Val Ile Phe Leu Asp Val Lys His Phe Ser Pro Glu Asp Leu Thr
1               5                   10                  15

Val Lys
```

<210> SEQ ID NO 57

<400> SEQUENCE: 57

000

<210> SEQ ID NO 58

<400> SEQUENCE: 58

000

<210> SEQ ID NO 59
<211> LENGTH: 6
<212> TYPE: PRT
<213> ORGANISM: Artificial Sequence
<220> FEATURE:
<223> OTHER INFORMATION: polypeptide

<400> SEQUENCE: 59

Tyr Lys Gly Ser Gly Phe
1               5

<210> SEQ ID NO 60
<211> LENGTH: 5
<212> TYPE: PRT
<213> ORGANISM: Artificial Sequence
<220> FEATURE:
<223> OTHER INFORMATION: polypeptide

<400> SEQUENCE: 60

Tyr Lys Gly Ser Gly
1               5